(12) United States Patent
Ho et al.

(10) Patent No.: US 9,085,808 B2
(45) Date of Patent: Jul. 21, 2015

(54) MATERIALS AND METHOD FOR DETECTING CYTOMEGALOVIRUS (CMV)

(75) Inventors: Shiaolan Y. Ho, Wilmette, IL (US); Catherine P. Barry, Deerfield, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 0 days.

(21) Appl. No.: 13/348,622

(22) Filed: Jan. 11, 2012

(65) Prior Publication Data
US 2013/0183657 A1 Jul. 18, 2013

Related U.S. Application Data

(60) Provisional application No. 61/432,012, filed on Jan. 12, 2011.

(51) Int. Cl.
*C12Q 1/68* (2006.01)
*C12Q 1/70* (2006.01)

(52) U.S. Cl.
CPC .............. *C12Q 1/705* (2013.01); *C12Q 1/6851* (2013.01); *C12Q 2600/16* (2013.01)

(58) Field of Classification Search
None
See application file for complete search history.

(56) References Cited

U.S. PATENT DOCUMENTS

| 5,627,030 A | 5/1997 | Pandian et al. |
| 6,306,602 B1 | 10/2001 | Sillekens et al. |
| 7,407,744 B2 * | 8/2008 | Liu et al. ........................... 435/5 |
| 2005/0227257 A1 | 10/2005 | Abravaya et al. |
| 2009/0263800 A1 | 10/2009 | Wohlgemuth et al. |

FOREIGN PATENT DOCUMENTS

| CA | 2281793 C | 9/2009 |
| CA | 2172142 C | 1/2010 |
| EP | 1013776 A1 | 6/2000 |
| EP | 0729518 B1 | 11/2001 |
| EP | 0973948 B1 | 1/2008 |
| WO | 9313227 A1 | 7/1993 |

OTHER PUBLICATIONS

NCBI Accession No. GC514762 (Aug. 18, 2008).*
Dunn et al. (Functional profiling of a human cytomegalovirus genome, PNAS, col. 100, No. 24, 14223-14228, Nov. 25, 2003).*
Fryer et al. (Collaborative Study to Evaluate the Proposed 1st WHO International Standard for Human Cytomegalovirus (HCMV) for Nucleic Acid Amplification (NAT)-Based Assays, attached, Oct. 18, 2010).*
Chamber et al. (DNA Microarrays of the Complex Human Cytomegalovirus Genome: Profiling Kinetic Class with Drug Sensitivity of Viral Gene Expression, Journal of Virology, vol. 73, No. 7, p. 5757-5766, Jul. 1999).*
Najioullah et al. (Development of a real-time PCR procedure including an internal control for the measurement of HCMV viral load, Journal of Virological Methods, 92;55-64, 2001).*
Mackay et al. (Real-time PCR in virology, Nucleic Acids Research, vol. 30, No. 6, 1292-1305, 2002).*
Nolan et al. (Quantification of mRNA using real-time RT-PCR, Nature Protocols, vol. 1, No. 3, Nov. 9, 2006).*
Untergasser et al. (Primer3Plus, an enhanced web interface to Primer3, Nucleic Acids Research, 2007, vol. 35, 2007).*
Rozen et al. (Primer3 on the WWW for General Users and for Biologist Programmers, in Methods in Molecular Biology, vol. 132: Bioinformatics Methods and Protocols, 2000).*
Buck et al. ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Haynes et al. (NIST Candidate Standard Reference Material (SRM): Cytomegalovirus DNA, Poster, attached, Nov. 18, 2010).*
Loveland et al. (Amino-Conserved Domain Critical to Virus Production, Journal of Virology, Jan. 2007, p. 620-628).*
BLAST of instant seq id No. 16 (attached, accessed May 14, 2014).*
BLAST of Chamber UL80 probe (attached, accessed May 14, 2014).*
BLAST of Liu 546 down2C (attached, accessed May 14, 2014).*
BLAST of Liu 546 up2C (attached, accessed May 14, 2014).*
NCBI Accession No. NC006273 2 (attached, accessed May 14, 2014).*
Abbott RealTime 02_CMV IDE Section 2.0, Report of Prior Investigations, Dec. 2012.
Abbott RealTime CMV, In Vitro Test, Ref 5N23, 51-608107/R3.
Allen R.D., et al., "Nonradioactive PCR-enzyme-linked Immunosorbent Assay Method for Detection of Human Cytomegalovirus DNA," Journal of Clinical Microbiology, 1995, vol. 33 (3), pp. 725-728.
Allice T., et al., "Evaluation of a Novel Real-time PCR System for Cytomegalovirus DNA Quantitation on Whole Blood and Correlation with pp65-antigen Test in Guiding Pre-emptive Antiviral Treatment," Journal of Virological Methods, 2008, vol. 148 (1-2), pp. 9-16.
Bates M., et al., "High Human Cytomegalovirus Loads and Diverse Linked Variable Genotypes in both HIV-1 Infected and Exposed, but Uninfected, Children in Africa," Virology, 2008, vol. 382 (1), pp. 28-36.
Bitsch A., et al., "Cytomegalovirus Transcripts in Peripheral Blood Leukocytes of Actively Infected Transplant Patients Detected by Reverse Transcription-polymerase Chain Reaction," Journal of Infectious Diseases, 1993, vol. 167 (3), pp. 740-743.
Boeckh M., et al., "Optimization of Quantitative Detection of Cytomegalovirus DNA in Plasma by Real-time PCR," Journal of Clinical Microbiology, 2004, vol. 42 (3), pp. 1142-1148.

(Continued)

*Primary Examiner* — Christopher M Babic
*Assistant Examiner* — Aaron Priest
(74) *Attorney, Agent, or Firm* — Lisa V. Mueller; Michael Best & Friedrich LLP

(57) ABSTRACT

Methods and kits for amplifying cytomegalovirus (CMV) nucleic acid sequences in a sample comprising pairs of primers for amplification of UL34 and UL80.5 nucleic acid sequences or one or more reagents.

6 Claims, 8 Drawing Sheets

(56) References Cited

OTHER PUBLICATIONS

Caliendo A.M., et al., "Comparison of Quantitative Cytomegalovirus (CMV) PCR in Plasma and CMV Antigenemia Assay: Clinical Utility of the Prototype Amplicor CMV Monitor Test in Transplant Recipients," Journal of Clinical Microbiology, 2000, vol. 38 (6), pp. 2122-2127.

Chambers J., et al., "DNA Microarrays of the Complex Human Cytomegalovirus Genome: Profiling Kinetic Class with Drug Sensitivity of Viral Gene Expression," Journal of Virology, 1999, vol. 73 (7), pp. 5757-5766.

Choi S.M., et al., "Comparison of Quantitative Cytomegalovirus Real-time PCR in Whole Blood and pp65 Antigenemia Assay: Clinical Utility of CMV Real-time PCR in Hematopoietic Stem Cell Transplant Recipients," Journal of Korean Medical Science, 2009, vol. 24 (4), pp. 571-578.

Chou S., "Cytomegalovirus Infection," Current Opinion in Infectious Diseases, 1992, vol. 5, pp. 427-432.

Chou S., "Effect of Interstrain Variation on Diagnostic DNA Amplification of the Cytomegalovirus Major Immediate-early Gene Region," Journal of Clinical Microbiology, 1992, vol. 30 (9), pp. 2307-2310.

De La Cruz-Vicente F., et al., "Clinical Utility of Real-time Polymerase Chain Reaction to Quantify Cytomegalovirus Replication in Allogeneic Stem Cell Transplant Recipients with Different Prevention Strategies," Transplantation Proceedings, 2010, vol. 42 (8), pp. 3228-3229.

De La Cruz-Vicente F., et al., "Differences in Cytomegalovirus Replication Quantified Using Quantitative Polymerase Chain Reaction and Antigenemia after Allogeneic Stem Cell Transplantation," Transplantation Proceedings, 2010, vol. 42 (8), pp. 3230-3231.

Delgado R., et al., "Low Predictive Value of Polymerase Chain Reaction for Diagnosis of Cytomegalovirus Disease in Liver Transplant Recipients," Journal of Clinical Microbiology, 1992, vol. 30 (7), pp. 1876-1878.

Distefano A.L., et al., "Human Cytomegalovirus: Detection of Congenital and Perinatal Infection in Argentina," BMC Pediatrics, 2004, vol. 4, pp. 11.

Dolan A., et al., "Genetic Content of Wild-type Human Cytomegalovirus," Journal of General Virology, 2004, vol. 85 (Pt 5), pp. 1301-1312.

Drew W.L., "Cytomegalovirus Infection in Patients with AIDS," Clinical Infectious Diseases, 1992, vol. 14, pp. 608-615.

Drew W.L., "Cytomegalovirus infection in patients with AIDS," Journal of Infectious Diseases, 1988, vol. 158 (2), pp. 449-456.

Ducroux A., et al., "Evaluation of New Commercial Real-time PCR Quantification Assay for Prenatal Diagnosis of Cytomegalovirus Congenital Infection," Journal of Clinical Microbiology, 2008, vol. 46 (6), pp. 2078-2080.

Dunn W., et al., "Functional Profiling of a Human Cytomegalovirus Genome," Proceedings of the National Academy of Sciences, 2003, vol. 100 (24), pp. 14223-14228.

Dunn W., Functional Profiling of a Human Cytomegalovirus Genome, Online Supporting Material, Nov. 25, 2003, 3 pages.

Einsele H., et al., "Polymerase Chain Reaction Monitoring Reduces the Incidence of Cytomegalovirus Disease and the Duration and Side Effects of Antiviral Therapy After Bone Marrow Transplantation," Blood, 1995, vol. 86 (7), pp. 2815-2820.

Emery V.C., et al., "Application of Viral-load Kinetics to Identify Patients Who Develop Cytomegalovirus Disease After Transplantation," Lancet, 2000, vol. 355 (9220), pp. 2032-2036.

Fryer J.F., et al., "Collaborative Study to Evaluate the Proposed 1st WHO International Standard for Human Cytomegalovirus (HCMV) for Nucleic Acid Amplification (NAT)-Based Assays," World Health Organization, 2010, vol. 1, 40 pages.

Fukushima E., et al., "Identification of a Highly Conserved Region in the Human Cytomegalovirus Glycoprotein H Gene and Design of Molecular Diagnostic Methods Targeting the Region," Journal of Virological Methods, 2008, vol. 151 (1), pp. 55-60.

Gault E., et al., "Quantification of Human Cytomegalovirus DNA by Real-time PCR," Journal of Clinical Microbiology, 2001, vol. 39 (2), pp. 772-775.

Gerna G., et al., "Comparison of Different Immunostaining Techniques and Monoclonal Antibodies to the Lower Matrix Phosphoprotein (pp65) for Optimal Quantitation of Human Cytomegalovirus Antigen," Journal of Clinical Microbiology, 1992, vol. 30 (5), pp. 1232-1237.

Gerna G., et al., "Monitoring of Human Cytomegalovirus Infections and Ganciclovir Treatment in Heart Transplant Recipients by Determination of Viremia, Antigenemia, and DNAemia," Journal of Infectious Diseases, 1991, vol. 164 (3), pp. 488-498.

Gerna G., et al., "Validation of a DNAemia Cutoff for Preemptive Therapy of Cytomegalovirus Infection in Adult Hematopoietic Stem Cell Transplant Recipients," Bone Marrow Transplantation, 2008, vol. 41 (10), pp. 873-879.

Gibson W., "Structure and Formation of the Cytomegalovirus Virion," Current Topics in Microbiology and Immunology, 2008, vol. 325, pp. 187-204.

Gimeno C., et al., "Quantification of DNA in Plasma by an Automated Real-time PCR Assay (Cytomegalovirus PCR Kit) for Surveillance of Active Cytomegalovirus Infection and Guidance of Preemptive Therapy for Allogeneic Hematopoietic Stem Cell Transplant Recipients," Journal of Clinical Microbiology, 2008, vol. 46 (10), pp. 3311-3318.

Gokahmetoglu S., et al., "Comparison of Real-Time, and Qualitative Polymerase Chain Reaction Assays in Detection of Cytomegalovirus DNA in Clinical Specimens," Saudi Medical Journal, 2007, vol. 28 (11), pp. 1658-1661. Abstract.

Gouarin; S. et al., "Multicentric Evaluation of a New Commercial Cytomegalovirus Real-Time PCR Quantitation Assay", 2007, 146 (1-2), 147-154.

Habbal W., et al., "Comparative Evaluation of Published Cytomegalovirus Primers for Rapid Real-time PCR: Which are the Most Sensitive?," Journal of Medical Microbiology, 2009, vol. 58 (Pt 7), pp. 878-883.

Hanson K.E., et al., "Comparison of the Digene Hybrid Capture System Cytomegalovirus (CMV) DNA (version 2.0), Roche CMV UL54 Analyte-specific Reagent, and QIAGEN RealArt CMV LightCycler PCR Reagent Tests Using AcroMetrix OptiQuant CMV DNA Quantification Panels and Specimens from Allogeneic-stem-cell Transplant Recipients," Journal of Clinical Microbiology, 2007, vol. 45 (6), pp. 1972-1973.

Harrington S.M., et al., "The Effect of Quantification Standards Used in Real-time CMV PCR Assays on Guidelines for Initiation of Therapy in Allogeneic Stem Cell Transplant Patients," Bone Marrow Transplantation, 2007, vol. 39 (4), pp. 237-238.

Herrmann B., et al., "Comparison of a Duplex Quantitative Real-time PCR Assay and the COBAS Amplicor CMV Monitor Test for Detection of Cytomegalovirus," Journal of Clinical Microbiology, 2004, vol. 42 (5), pp. 1909-1914.

Hong K.M., et al., "Quantitative Real-time PCR with Automated Sample Preparation for Diagnosis and Monitoring of Cytomegalovirus Infection in Bone Marrow Transplant Patients," Clinical Chemistry, 2004, vol. 50 (5), pp. 846-856.

Humar A., et al., "American Society of Transplantation Recommendations for Screening, Monitoring and Reporting of Infectious Complications in Immunosuppression Trials in Recipients of Organ Transplantation," American Society of Transplantation, 2006, vol. 6 (2), pp. 262-274.

International Search Report for Application No. PCT/US2012/020997, mailed on May 15, 2012, 7 pages.

Jahn G., et al., "Diagnostics of Persistent Viruses: Human Cytomegalovirus as an Example," Intervirology, 1993, vol. 35 (1-4), pp. 60-72.

Kalpoe J.S., et al., "Validation of Clinical Application of Cytomegalovirus Plasma DNA Load Measurement and Definition of Treatment Criteria by Analysis of Correlation to Antigen Detection," Journal of Clinical Microbiology, 2004, vol. 42 (4), pp. 1498-1504.

Kearns A.M., et al., "LightCycler-based Quantitative PCR for Detection of Cytomegalovirus in Blood, Urine, and Respiratory Samples," Journal of Clinical Microbiology, 2001, vol. 39 (6), pp. 2364-2365.

(56) References Cited

OTHER PUBLICATIONS

Koidl C., et al., "Detection of CMV DNA: Is EDTA Whole Blood Superior to EDTA Plasma?," Journal of Virological Methods, 2008, vol. 154 (1-2), pp. 210-212.

Kotenko S.V., et al., "Human Cytomegalovirus Harbors its Own Unique IL-10 Homolog (cmvIL-10)," Proceedings of the National Academy of Sciences, 2000, vol. 97 (4), pp. 1695-1700.

Kotton C.N., et al., "International Consensus Guidelines on the Management of Cytomegalovirus in Solid Organ Transplantation," Transplantation, 2010, vol. 89 (7), pp. 779-795.

Lengerke C., et al., "Evaluation of the COBAS Amplicor HCMV Monitor for Early Detection and Monitoring of Human Cytomegalovirus Infection After Allogeneic Stem Cell Transplantation," Bone Marrow Transplantation, 2006, vol. 38 (1), pp. 53-60.

Leruez-Ville M., et al., "Exon 4 of the Human Cytomegalovirus (CMV) Major Immediate-early Gene as a Target for CMV Real-time PCR," Journal of Clinical Microbiology, 2008, vol. 46 (4), pp. 1571-1572.

Lilleri D., et al., "Clinically-based Determination of Safe DNAemia Cutoff Levels for Preemptive Therapy or Human Cytomegalovirus Infections in Solid Organ and Hematopoietic Stem Cell Transplant Recipients," Journal of Medical Virology, 2004, vol. 73 (3), pp. 412-418.

Lilleri D., et al., "Use of a DNAemia Cut-off for Monitoring Human Cytomegalovirus Infection Reduces the Number of Preemptively Treated Children and Young Adults Receiving Hematopoietic Stem-cell Transplantation Compared with Qualitative pp65 Antigenemia," Blood, 2007, vol. 110 (7), pp. 2757-2760.

Limaye A.P., et al., "Cytomegalovirus (CMV) DNA Load in Plasma for the Diagnosis of CMV Disease before Engraftment in Hematopoietic Stem-cell Transplant Recipients," Journal of Infectious Diseases, 2001, vol. 183 (3), pp. 377-382.

Limaye A.P., et al., "Cytomegalovirus Reactivation in Critically ill Immunocompetent Patients," Journal of the American Medical Association, 2008, vol. 300 (4), pp. 413-422.

Loh H.S., et al., "Development of a Quantitative Real-time RT-PCR for Kinetic Analysis of Immediate-early Transcripts of Rat Cytomegalovirus," Acta Virologica, 2009, vol. 53 (4), pp. 261-269.

Madhavan H.N., et al., "Development and Application of a Novel Multiplex Polymerase Chain Reaction for Semi-quantitation of Human Cytomegalovirus in Clinical Specimens," Journal of Virological Methods, 2007, vol. 141 (2), pp. 166-172.

Marque-Juillet S., et al., "Evaluation of Cytomegalovirus Quantification in Blood by the R-gene Real-time PCR Test," Pathologie Biologie, 2010, vol. 58 (2), pp. 162-165.

Matsui Y., et al., "CMV Quantitative PCR in the Diagnosis of CMV-associated AGML in an Immunocompetent Host," Internal Medicine, 2010, vol. 49 (12), pp. 1265-1267.

Mendez J.C., et al., "Evaluation of PCR Primers for Early Diagnosis of Cytomegalovirus Infection Following Liver Transplantation," Journal of Clinical Microbiology, 1998, vol. 36 (2), pp. 526-530.

Meyer T., et al., "Identification of Active Cytomegalovirus Infection by Analysis of Immediate-Early, Early and Late Transcripts in Peripheral Blood Cells of Immunodeficient Patients," Molecular and Cellular Probes, 1994, vol. 8 (4), pp. 261-271.

Meyers J.D., et al., "Risk Factors for Cytomegalovirus Infection after Human Marrow Transplantation," Journal of Infectious Diseases, 1986, vol. 153 (3), pp. 478-488.

Michelin B.D., et al., "Detection of Cytomegalovirus (CMV) DNA in EDTA Whole-Blood Samples: Evaluation of the Quantitative Artus CMV Light Cycler PCR Kit in Conjunction with Automated Sample Preparation," Journal of Clinical Microbiology, 2008, vol. 46 (4), pp. 1241-1245.

Mori T., et al., "Dose-adjusted Preemptive Therapy for Cytomegalovirus Disease based on Real-time Polymerase Chain Reaction after Allogeneic Hematopoietic Stem Cell Transplantation," Bone Marrow Transplantation, 2002, vol. 29 (9), pp. 777-782.

Mullier F., et al., "Definition of Clinical Threshold for CMV Real-Time PCR after Comparison with PP65 Antigenaemia and Clinical Data," Acta Clinica Belgica, 2009, vol. 64 (6), pp. 477-482.

Naumnik B., et al., "Comparison of Serology Assays and Polymerase Chain Reaction for the Monitoring of Active Cytomegalovirus Infection in Renal Transplant Recipients," Transplantation Proceedings, 2007, vol. 39 (9), pp. 2748-2750.

Pang X., et al., "Concurrent Genotyping and Quantitation of Cytomegalovirus gB Genotypes in Solid-organ-transplant Recipients by Use of a Real-time PCR Assay," Journal of Clinical Microbiology, 2008, vol. 46 (12), pp. 4004-4010.

Piiparinen H., et al., "Comparison of Two Quantitative CMV PCR Tests, Cobas Amplicor CMV Monitor and TaqMan Assay, and pp65-antigenemia Assay in the Determination of Viral Loads from Peripheral Blood of Organ Transplant Patients," Journal of Clinical Virology, 2004, vol. 30 (3), pp. 258-266.

Pumannova M., et al., "Comparison of Quantitative Competitive Polymerase Chain Reaction-enzyme-linked Immunosorbent Assay with LightCycler-based Polymerase Chain Reaction for Measuring Cytomegalovirus DNA in Patients after Hematopoietic Stem Cell Transplantation," Diagnostic Microbiology and Infectious Disease, 2006, vol. 54 (2), pp. 115-120.

Raggam R.B., et al., "Rapid Quantitation of Cytomegalovirus DNA in Whole Blood by a New Molecular Assay based on Automated Sample Preparation and Real-time PCR," Medical Microbiology and Immunology, 2010, vol. 199 (4), pp. 311-316.

Razonable R.R., et al., "Role of the Laboratory in Diagnosis and Management of Cytomegalovirus Infection in Hematopoietic Stem Cell and Solid-organ Transplant Recipients," Journal of Clinical Microbiology, 2002, vol. 40 (3), pp. 746-752.

Ruell J., et al., "Active CMV Disease does not Always Correlate with Viral Load Detection," Bone Marrow Transplantation, 2007, vol. 40 (1), pp. 55-61.

Sanghavi S.K., et al., "Relationship of Cytomegalovirus Load Assessed by Real-time PCR to pp65 Antigenemia in Organ Transplant Recipients," Journal of Clinical Virology, 2008, vol. 42 (4), pp. 335-342.

Schmidt G.M., et al., "A Randomized, Controlled Trial of Prophylactic Ganciclovir for Cytomegalovirus Pulmonary Infection in Recipients of Allogeneic Bone Marrow Transplants," New England Journal of Medicine, 1991, vol. 324 (15), pp. 1005-1011.

Schnepf N., et al., "Rapid Determination of Antiviral Drug Susceptibility of Human Cytomegalovirus by Real-time PCR," Antiviral Research, 2009, vol. 81 (1), pp. 64-67.

Storch G.A., et al., "Comparison of PCR and pp65 Antigenemia Assay with Quantitative Shell Vial Culture for Detection of Cytomegalovirus in Blood Leukocytes from Solid-organ Transplant Recipients," Journal of Clinical Microbiology, 1994, vol. 32 (4), pp. 997-1003.

Tanaka Y., et al., "Monitoring Cytomegalovirus Infection by Antigenemia Assay and Two Distinct Plasma Real-time PCR Methods after Hematopoietic Stem Cell Transplantation," Bone Marrow Transplantation, 2002, vol. 30 (5), pp. 315-319.

Thorne L.B., et al., "Analytic Validation of a Quantitative Real-time PCR Assay to Measure CMV Viral Load in Whole Blood," Diagnostic Molecular Pathology, 2007, vol. 16 (2), pp. 73-80.

Van Doornum G.J., et al., "Diagnosing Herpesvirus Infections by Real-time Amplification and Rapid Culture," Journal of Clinical Microbiology, 2003, vol. 41 (2), pp. 576-580.

Verkruyse L.A., et al., "Once Daily Ganciclovir as Initial Pre-emptive Therapy Delayed until Threshold CMV Load > or =10000 Copies/ml: A Safe and Effective Strategy for Allogeneic Stem Cell Transplant Patients," Bone Marrow Transplantation, 2006, vol. 37 (1), pp. 51-56.

Weinberg A., et al., "Evaluation of a Commercial PCR Kit for Diagnosis of Cytomegalovirus Infection of the Central Nervous System," Journal of Clinical Microbiology, 1998, vol. 36 (11), pp. 3382-3384.

Wolff D.J., et al., "Multi-Site PCR-based CMV Viral Load Assessment-assays Demonstrate Linearity and Precision, but Lack Numeric Standardization: A Report of the Association for Molecular Pathology," Journal of Molecular Diagnostics, 2009, vol. 11 (2), pp. 87-92.

Xue W., et al., "Methodology for Monitoring Cytomegalovirus Infection after Renal Transplantation," Clinical Chemistry and Laboratory Medicine, 2009, vol. 47 (2), pp. 177-181.

Zipeto D., et al., "Development and Clinical Significance of a Diagnostic Assay Based on the Polymerase Chain Reaction for Detection of Human Cytomegalovirus DNA in Blood Samples from Immunocompromised Patients," Journal of Clinical Microbiology, 1992, vol. 30 (2), pp. 527-530.

Zweygberg Wirgart B., et al., "Sequence Variation within Three Important Cytomegalovirus Gene Regions in Isolates from Four Different Patient Populations," Journal of Clinical Microbiology, 1998, vol. 36 (12), pp. 3662-3669.

\* cited by examiner

MATERIALS AND METHOD FOR DETECTING CYTOMEGALOVIRUS (CMV)

CROSS REFERENCE TO RELATED APPLICATIONS

This claims priority to U.S. Provisional Application No. 61/432,012, filed on Jan. 12, 2011, the content of which is incorporated herein by reference in its entirety.

TECHNICAL FIELD

The present disclosure relates to the detection of CMV in a biological sample, in particular plasma and whole blood, by a nucleic acid-based method, such as nucleic acid amplification, in particular real-time polymerase chain reaction (real-time PCR), and materials, such as primers, probes and kits, for use in such methods.

BACKGROUND

CMV is a ubiquitous Herpes-type virus having a linear, double-stranded DNA genome of about 236,000 kbp (Gibson, "Structure and Formation of the Cytomegalovirus Virion," *Human Cytomegalovirus*, Curr. Topics in Microbiol. Immunol. 325: 187-204, Shenk and Stinski, eds., Springer-Verlag Berlin Heidelberg (2008)). The CMV genome is organized as two regions of unique sequences, unique long (UL) and unique short (US) (Kotenko et al., PNAS USA 97(4): 1695-1700 (Feb. 15, 2000)). The UL region is flanked by a set of inverted repeats, terminal repeat long (TRL) and internal repeat long (IRL; inverted repeat of TRL), and the US region is flanked by another set of inverted repeats, internal repeat short (IRS; inverted repeat of TRS) and TRS (terminal repeat short) (Kotenko et al. (2000), supra; see, also, Dunn et al., PNAS 100(24): 14223-14228 (Nov. 25, 2003)).

CMV infects 40-80% of humans before puberty. CMV becomes latent after primary infection, which often is asymptomatic. Even recurrent infection is asymptomatic in most cases or leads to only mild disease in an immunocompetent host. However, in congenitally infected infants and immunocompromised patients, such as allograft recipients (Meyers et al., J. Infect. Dis. 153: 478-488 (1986)) or autoimmune deficiency syndrome (AIDS) patients (Drew, J. Infect. Dis. 158: 449-456 (1988); and Drew, Clin. Infect. Dis. 14: 608-615 (1992)), CMV can cause severe and sometimes life-threatening diseases, including retinitis, gastrointestinal disorders (see, e.g., acute gastric mucosal lesion (AGML) as reported by Matsui et al., Internal Medicine 49: 1265-1267 (2010)), and encephalitis (Drew (1992), supra). Half of allogeneic stem cell recipients develop CMV infection in the first 100 days after transplantation (de la Cruz-Vicente et al., Transplant Proc. 42(8): 3230-3231 (October 2010)). CMV end-organ disease is a serious, frequent complication of allogeneic stem cell transplantation (de la Cruz-Vicente et al., Transplant Proc. 42(8): 3228-3229 (October 2010)).

Early administration of antiviral drugs (e.g., ganciclovir and foscarnet) can have significant beneficial effects on the prognosis of a patient (Jahn et al., Intervirology 35: 60-72 (1993); Schmidt et al., N. Engl. J. Med. 324: 1005-1011 (1991)). Since clinically effective antiviral therapy is available, early and sensitive diagnosis is significantly important.

Various methods have been used to assay CMV. Anti-CMV antibodies, in particular IgM antibodies, can be used as a marker for CMV infection. However, the detection of anti-CMV antibodies has limited value in the discrimination of latent and active infection. Naumnik et al. (Transplant Proc. 39(9): 2748-2750 (November 2007)) have reported that detection of CMV-IgM antibodies by various immunoassays is not sensitive enough for diagnosis and cannot be used for monitoring during the active period in renal transplant recipients.

Most currently employed viral detection methods do not unambiguously allow for prediction of whether a given infection will become symptomatic. Serological methods are indirect and often lack sensitivity. While viral culture is a more direct diagnostic parameter for CMV viremia, such as viral culture from blood cells, the method is technically difficult and does not enable rapid diagnosis. Moreover, viral culture does not necessarily correspond to CMV disease. Isolation of virus from peripheral leukocytes may not predict clinical symptoms in some immunosuppressed patients (Delgado et al., J. Clin. Microbiol. 30: 1876-1878 (1992)). Similarly, urinary or pharyngeal shedding of the virus frequently occurs without clinical symptoms and organ involvement. Amplification of CMV DNA in peripheral leukocytes using PCR can occasionally detect CMV DNA, such as latent viral genomes, in peripheral leukocytes without CMV-related diseases (Jahn et al. (1993), supra; Zipeto et al., J. Clin. Microbiol. 30: 527-530 (1992); and Delgado et al. (1992), supra). The antigenemia assay has been frequently used for the early diagnosis of acute symptomatic CMV infection.

The antigenemia assay involves the detection of the structural protein pp 65 using specific antibodies (Storch et al., J. Clin. Microbiol. 32: 997-1003 (1994); Gerna et al., J. Infect. Dis. 164: 488-498 (1991); and Gerna et al., J. Clin. Microbiol. 30: 1232-1237 (1992)). However, the number of pp 65-positive cells may be very low early in infection, and the stability of the pp 65 protein appears to be limited (Chou et al., Curr. Opin. Infect. Dis. 5: 427-432 (1991)). In addition, the antigenemia assay requires immediate sample processing and suffers from non-standardization of sample processing between laboratories, inaccurate reflection of the viral load in the blood compartment, occasional negative results in the presence of CMV disease, a time-consuming and laborious procedure, an inability to be automated, a lack of feasibility during periods of neutropenia, and a lack of objectivity of quantification (Choi et al. (2009), supra; Gimeno et al., J. Clin. Microbiol. 46(1): 3311-3318 (October 2008; epub Aug. 27, 2008)).

Since viral replication requires transcription, the presence of CMV mRNA as a marker of active CMV infection has been investigated (Bitsch et al., J. Infect. Dis. 167: 740-743 (1993)). RNA amplification has been used (Bitsch et al. (1993), supra; Meyer et al., Mol. Cell. Probes 8: 261-271 (1994); and Gerna et al. (1992), supra). Sillekens et al. (U.S. Pat. No. 6,306,602 B1, EP 0 729 518 B1, EP 0 973 948 B1, CA 2 172 142, and CA 2 281 793) discloses that the detection of a certain late mRNA, namely the matrix tegument protein pp 67 encoding gene sequence (UL65), which is expressed during the late phase of CMV infection, is related to the appearance of clinical symptoms of CMV disease. Analysis of immediate-early 1 (IE1) and immediate-early 2 (IE2) transcripts (Loh et al., Acta Virol. 53(4): 261-269 (2009)) and R-gene transcripts (CMV R-gene™ kit (Argene, Inc., Shirley, N.Y.); Marque-Juillet et al., Pathol. Biol. (Paris) 58(2): 162-165 (April 2010; epub 10.24.09)) also have been described. The CMV HHV6,7,8 R-gene™ kit of Argene, Inc. (Shirley, N.Y.), reportedly enables the detection of ppUL83 transcripts for CMV, along with U57 transcripts for HHV-6, U42 transcripts for HHV-7, and ORF26 transcripts for HHV-8 (see, also, Raggam et al., Med. Microbiol. Immunol. 199(4): 311-316 (November 2010; epub 6.18.10). A PCR-ELISA method employing primers for glycoprotein H (gH5) has been described by Allen et al., J. Clin. Microbiol. 33(3): 725-728 (March 1995)).

While real-time PCR is widely considered to be an efficient and highly sensitive technique for the evaluation of CMV DNA kinetics (Hong et al., Clin. Chem. 50: 846-856 (2004); Kearns et al., J. Clin. Microbiol. 39: 2364-2365 (2001); Piiparinen et al., J. Clin. Virol. 30: 258-266 (2004); and van Doornum et al., J. Clin. Microbiol. 41: 576-580 (2003)), the sensitivity and reliability of CMV DNA detection is greatly dependent on target sequence and primer selection, since there is sequence variation among strains of CMV throughout the genome (see, e.g., Caliendo et al., J. Clin. Microbiol. 38: 2122-2127 (2000); and Gault et al., J. Clin. Microbiol. 39: 772-775 (2001)). Chou (J. Clin. Microbiol. 30(9): 2307-2310 (September 1992)) compared the immediate-early region exon 4 sequence of six clinical CMV strains with two laboratory strains and found 8.1% inter-strain variation at the peptide level and 18% inter-strain variation at the nucleotide level in 407 codons in exon 4. The variation reportedly occurred sporadically throughout the exon without apparent strain grouping. Chou et al. also reported that some of the published oligonucleotide primers proposed for amplification of exon 4 sequences in the diagnostic detection of CMV by PCR showed sequence mismatches with the examined strains. Such mismatch reportedly reduced amplification sensitivity by up to 100-fold.

Numerous CMV gene targets have been used for PCR amplification and quantitation. Examples include the HindIII X region (Wolff et al., J. Molec. Diag. 11(2): 87-92 (2009)), UL 117 (Wolff et al. (2009), supra), UL123 (Wolff et al. (2009, supra); Ducroux et al., J. Clin. Microbiol. 46(6): 2078-2080 (2008); and Gimeno et al., J. Clin. Micro. 46(10): 3311-3318 (2008)), UL125 (Boeckh et al., J. Clin Micro. 42(3): 1142-1148 (2004)), UL126 (Boeckh et al. (2004), supra), UL54 (Wolff et al. (2009), supra; Fukushima et al., J. Virol. Meth. 151: 55-60 (2008); Sanghavi et al., J. Clin. Virol. 42: 335-342 (2008); and Hantz et al., Antiviral Res. 81: 64-67 (2009)), UL55 (Wolff et al. (2009), supra; Fukushima et al. (2008), supra; Bourne et al., Virol. 382: 28-36 (2008); and Pang et al., J. Clin. Micro. 46(12): 4004-4010 (2008)), UL55/UL123 (Boeckh et al. (2004), supra; and Limaye et al., JAMA 300(4): 413-422 (2008)), UL73 (Bourne et al. (2008), supra), UL74 (Bourne et al. (2008), supra), UL75 (Fukushima et al. (2008), supra), UL83 (Wolff et al. (2009), supra; Ducroux et al. (2008), supra; and Fukushima et al. (2008), supra), and US17 (Sanghavi et al. (2008), supra).

Habbal et al. (J. Med. Microbiol. 58: 878-883 (2009)) describe the comparative sensitivity of published primers for single-round, real-time PCR assay of CMV. Three primer sets located in the glycoprotein B (UL55) gene region were found to be the most sensitive in the analysis of CMV strain AD169; however, two of the three primer sets showed a considerable number of mismatches with clinical isolates in a BLAST search. Two other pairs of primers from the lower matrix phosphoprotein (UL83) gene and the DNA polymerase (UL54) gene showed reasonable sensitivity and no mismatches with clinical isolates. Further testing indicated that the UL55 primer set, which did not show a considerable number of mismatches with clinical isolates by BLAST searching, and the UL54 primer set were the most sensitive. Additionally, the analytical sensitivity of the PCR inversely correlated with the size of the PCR product. Habbal et al. suggest a primer pair for the UL55 gene as a candidate for a standardized PCR for CMV.

Mendez et al. (J. Clin. Microbiol. 36(2): 526-530 (February 1998)) evaluated PCR primers for early diagnosis of CMV infection following liver transplantation. Peripheral blood leukocytes (PBLs) and serum were assayed. Primer pairs directed to the HindIII-X fragment region of CMV reportedly detected target DNA with 94% sensitivity, compared to 87% sensitivity with primer pairs directed to an EcoRI fragment D, 32% sensitivity with primer pairs directed to the immediate-early antigen 1 (IEA1) gene, and 20% sensitivity with primer pairs directed to the major immediate-early (MIE) gene. The sensitivity of the primers for amplifying CMV DNA associated with symptomatic infection reportedly ranged from 100% (HindIII-X) to 20% (MIE); specificity reportedly was inversely related to sensitivity (45% for HindIII-X and 91% for MIE). CMV DNA from PBLs reportedly was a more sensitive target for HindIII-X and EcoRI-D primer sets. Overall, primers directed to the HindIII-X fragment region were found to be optimal for early detection of CMV DNA in PBLs and sera from symptomatic liver transplant recipients.

Boeckh et al. (J. Clin. Microbiol. 42(3): 1142-1148 (March 2004)) compared PCR assay of plasma using three different primer sets (UL125 alone, UL126 alone, and UL55/UL123-exon 4) with pp 65 antigenemia assay and blood culture. Boeckh et al. reported that plasma PCR detected CMV more frequently in blood specimens that either the antigenemia assay or blood cultures. The PCR assay employing UL55/UL123-exon 4 primers reportedly performed better than the PCR assay employing primers for either UL125 or UL126 with regard to sensitivity, specificity and predictive value when compared to the antigenemia assay.

Gimeno et al. (J. Clin. Microbiol. 46(10): 3311-3318 (October 2008; epub 8.27.08) compared an automated real-time PCR assay (Cytomegalovirus PCR Kit, Abbott Molecular, Inc., Des Plaines, Ill.) with the antigenemia assay in the surveillance of active CMV infection in 42 allogeneic hematopoietic stem cell transplantation recipients. Gimeno et al. found that the real-time PCR assay allowed an earlier diagnosis of CMV from the blood. Analysis of the kinetics of DNAemia levels at a median of seven days post-treatment reportedly allowed the prediction of the response to CMV therapy. The PCR assay reportedly tested positive before the onset of symptoms and during the disease period for two patients that developed CMV colitis.

The use of three different primer sets (IE, LA, and gB) in PCR assay of viral isolates and the use of gB primers in PCR assay of urine and dried blood spots (DBS) on Guthrie Cards also has been assessed (Distefano et al., BMC Pediatr. 4: 11 (June 2004)). Primers directed to the gB fragment region reportedly were the best choice for the PCR detection of CMV DNA in positive isolates.

The AMPLICOR CMV PCR test (Roche Molecular Systems, Inc., Branchburg, N.J.) employs primers that target a region of the polymerase gene (UL54). The test reportedly is specific and sensitive and has a limit of detection adequate to detect CMV in cerebrospinal fluid (CSF) of 95% of patients with neurological CMV disease (Weinberg et al., J. Clin. Microbiol. 36(11): 3382-3384 (November 1998)).

The region of the polymerase gene has been suggested to be a better choice than the major immediate early (MIE) region for primer selection (Wirgart et al., J. Clin. Microbiol. 36(12): 3662-3669 (December 1998); see, also, Thorne et al., Diagn. Mol. Pathol. 16(2): 73-80 (June 2007)). However, Leruez-VIIIe et al. (J. Clin. Microbiol. 46(4): 1571-1572 (April 2008)) have reported that real-time PCR employing primers directed to a strictly conserved sequence in exon 4 of MIE was much more sensitive than the pp65 antigenemia assay, and compared favorably to the CMV R-gene real-time PCR (Argene, France), except at DNA load levels near the threshold values of the two techniques.

The Qiagen RealArt CMV LightCycler PCR (Qiagen, Germantown, Md.), which employs primers that target the CMV MIE region, was compared to the Roche CMV UL54 Analyte-Specific Reagent PCR (Roche Molecular Systems, Inc., Indianapolis, Ind.), which employs primers that target UL54, and the Digene Hybrid Capture System CMV DNA test (version 2.0; Digene Corp., Gaithersburg, Md.), which is a solution hybridization antibody capture assay for the chemiluminescent detection and quantitation of CMV DNA in leukocytes, by Hanson et al. (J. Clin. Microbiol. 45(6): 1972-1973 (June 2007)) using whole virus standards and plasma specimens from allogeneic stem cell transplant recipients. The Qiagen and Roche tests reportedly were more sensitive than the Digene test, detected CMV DNA earlier after transplant, and remained positive longer once antiviral treatment was initiated.

Koidl et al. (J. Virol. Methods 154(1-2): 210-212 (December 2008); epub 10.1.08) evaluated assay of CMV DNA in whole blood preserved with EDTA and plasma preserved with EDTA using two commercially available methods of detection, i.e., CMV HHV6,7,8 R-gene™ kit of Argene, Inc. (Shirley, N.Y.) and the artus CMV LC PCR kit (Qiagen, Hamburg, Germany). Whole blood preserved with EDTA was found to be superior to plasma preserved with EDTA when using the CMV HH6,7,8 R-gene™ kit.

As reported by Habbal et al. ((2009), supra), several evaluation studies have demonstrated significant differences in sensitivity of various in-house (also referred to as homebrew) and commercial PCRs (see, e.g., Allen et al. (1995), supra; Distefano et al. (2004), supra; Weinberg et al. (1998), supra; and Wirgart (1998), supra). Moreover, the most frequently used primers have failed to detect CMV in some isolates (see, e.g., Allen et al. (1995), supra; Distefano et al. (2004), supra; and Wirgart et al. (1998), supra). Habbal et al. concludes that such observations imply that the most appropriate target region for amplification has not yet been defined, and that standardization is still required for reliable and comparable PCR results. Further, as highlighted by Gimeno et al. ((2008), supra) and arguably supported by Koidl et al. ((2008), supra), analytical performance is also impacted by methods of detection and extraction. In this regard, Xue et al. (Clin. Chem. Lab Med. 47(2): 177-181 (2009)) concluded PCR should be used in combination with the antigenemia test to monitor CMV infection and predict its outcome, at least in the context of renal transplantation. Gimeno et al. ((2008), supra) on the other hand, opines that real-time PCR displays several advantages over the antigenemia assay for monitoring active CMV infection in allogeneic stem cell transplant patients. Such advantages include earlier diagnosis of active CMV infection, more reliable marker of successful clearance of CMV from blood, and the possible prediction of the response to CMV treatment by analysis of kinetics of CMV DNAemia at the time of initiation of pre-emptive therapy or early thereafter.

In view of the foregoing, there remains a need for oligonucleotide primers and probes for the amplification and subsequent detection of CMV that are specific, sensitive, and have a limit of detection adequate to detect CMV in any biological fluid sample, in particular blood or plasma. Desirably, the primers and probes enable detection of most strains of CMV, and even more desirably, all strains of CMV. The present disclosure seeks to provide further oligonucleotide primers and probes that, when used in combination in a PCR assay of CMV, provide a highly robust assay that is not only specific and sensitive but highly reproducible. This and other objects and advantages, as well as inventive features, will become apparent from the detailed description provided herein.

SUMMARY

A method of amplifying cytomegalovirus (CMV) nucleic acid sequences in a sample is provided. The method comprises (a) forming a mixture comprising the sample, nucleic acid amplification reagents, a pair of primers for amplification of a UL34 nucleic acid sequence, and a pair of primers for amplification of a UL80.5 nucleic acid sequence, and (b) subjecting the mixture to conditions that promote amplification of the UL34 nucleic acid sequence and the UL80.5 nucleic acid sequence. The primers for amplification of a UL34 nucleic acid sequence can amplify a nucleic acid sequence in the region from about nucleotide 29 to about nucleotide 79 of the UL34 coding domain sequence (CDS). One of the pair of primers for amplification of a UL34 nucleic acid sequence can specifically hybridize to the UL34 CDS in the region from about nucleotide 2 to about nucleotide 29, and the other of the pair of primers for amplification of a UL34 nucleic acid sequence can specifically hybridize to the UL34 CDS in the region from about nucleotide 78 to about nucleotide 106. The primers for amplification of a UL34 nucleic acid sequence can comprise, or consist essentially of, (i) 5' TGA ACT TCA TCA TCA CCA CCC GAG ACT 3' [SEQ ID NO: 49] as a forward primer, and (ii) 5' CCT TGT ACG CTT TGG AAA TCG AGC CTG 3' [SEQ ID NO: 50] as a reverse primer. The primers for amplification of a UL80.5 nucleic acid sequence can amplify a nucleic acid sequence in the region from about 2025 to about 2080 of the UL80.5 CDS. One of the pair of primers for amplification of a UL80.5 nucleic acid sequence can specifically hybridize to the UL80.5 CDS in the region from about 2005 to about 2025, and the other of the pair of primers for amplification of a UL80.5 nucleic acid sequence can specifically hybridize to the UL80.5 CDS in the region from about nucleotide 2078 to about nucleotide 2105. The primers for amplification of a UL80.5 nucleic acid sequence can comprise, or consist essentially of, (i) 5' CGG CTA GTG TCG TGT TAG C 3' [SEQ ID NO: 16] as a forward primer, and (ii) 5' CAC AAA AAT CCG CCG ATT CAG ATC 3' [SEQ ID NO: 47] as a reverse primer. The mixture in (a) can further comprises an internal control (IC) nucleic acid and a pair of primers for amplifying the IC nucleic acid, in which case the conditions in (b) also promote amplification of the IC nucleic acid. The method can further comprise simultaneously or subsequently detecting the presence, amount or concentration of CMV in the sample; when simultaneously detecting, the mixture in (a) can further comprise a probe for detection of amplification of a UL34 nucleic acid sequence and a probe for detection of amplification of a UL80.5 nucleic acid sequence. The probe for detection of amplification of a UL34 nucleic acid sequence can specifically hybridize to the UL34 CDS in the region from about nucleotide 29 to about nucleotide 79, such as in the region from about nucleotide 33 to about nucleotide 59. The nucleotide sequence of the probe for detection of amplification of a UL34 nucleic acid sequence can comprise, or consist essentially of, 5' CG ACG ATT CAG TCC TGC GAG CC 3' [SEQ ID NO: 51]. The probe for detection of amplification of a UL80.5 nucleic acid sequence can specifically hybridize to the UL80.5 CDS in the region from about 2025 to about 2080, such as in the region from about nucleotide 2040 to about nucleotide 2062. The nucleotide sequence of the probe for detection of amplification of a UL80.5 nucleic acid sequence can comprise, or consist essentially of, 5'AAGCCGCCG- CAGCTTCCCAG 3' [SEQ ID NO: 52]. Preferably, the probe is labeled with FAM and quenched by BHQ-1. The method can further comprise simultaneously or subsequently detecting the presence, amount or concentration of IC in the sample.

Also provided is a set of primers. The set of primers comprises a pair of forward and reverse primers for amplification of a CMV UL34 nucleic acid sequence and a pair of forward and reverse primers for amplification of a CMV UL80.5 nucleic acid sequence. The pair of forward and reverse primers for amplification of a CMV UL34 nucleic acid sequence can amplify a nucleic acid sequence in the region from about nucleotide 29 to about nucleotide 79 of the UL34 CDS, and the pair of forward and reverse primers for amplification of a CMV UL80.5 nucleic acid sequence can amplify a nucleic acid sequence in the region from about 2025 to about 2080 of the UL80.5 CDS. One of the pair of primers for amplification of a UL34 nucleic acid sequence can specifically hybridize to the UL34 CDS in the region from about nucleotide 2 to about nucleotide 29, and the other of the pair of primers for amplification of a UL34 nucleic acid sequence can specifically hybridize to the UL34 CDS in the region from about nucleotide 78 to about nucleotide 106. One of the pair of primers for amplification of a UL80.5 nucleic acid sequence can specifically hybridize to the UL80.5 CDS in the region from about 2005 to about 2025, and the other of the pair of primers for amplification of a UL80.5 nucleic acid sequence can specifically hybridize to the UL80.5 CDS in the region from about nucleotide 2078 to about nucleotide 2105. The primers for amplification of a UL34 nucleic acid sequence can comprise, or consist essentially of, (i) 5' TGA ACT TCA TCA TCA CCA CCC GAG ACT 3' [SEQ ID NO: 49] as a forward primer, and (ii) 5' CCT TGT ACG CTT TGG AAA TCG AGC CTG 3' [SEQ ID NO: 50] as a reverse primer, and the primers for amplification of a UL80.5 nucleic acid sequence can comprise, or consist essentially of, (i') 5' CGG CTA GTG TCG TGT TAG C 3' [SEQ ID NO: 16] as a forward primer, and (ii') 5' CAC AAA AAT CCG CCG ATT CAG ATC 3' [SEQ ID NO: 47] as a reverse primer.

Further provided is a set of probes. The set of probes comprises a probe for detection of amplification of a CMV UL34 nucleic acid sequence and a probe for detection of amplification of a CMV UL80.5 nucleic acid sequence. The probe for detection of amplification of a UL34 nucleic acid sequence can specifically hybridize to the UL34 CDS in the region from about nucleotide 29 to about nucleotide 79, such as from about nucleotide 33 to about nucleotide 59, and the probe for detection of amplification of a UL80.5 nucleic acid sequence can specifically hybridize to the UL80.5 CDS in the region from about 2025 and about 2080, such as from about nucleotide 2040 to about nucleotide 2062. The nucleotide sequence of the probe for detection of amplification of a UL34 nucleic acid sequence can comprise, or consist essentially of, 5' CG ACG ATT CAG TCC TGC GAG CC 3' [SEQ ID NO: 51], and the nucleotide sequence of the probe for detection of amplification of a UL80.5 nucleic acid sequence can comprise, or consist essentially of, 5'AAGCCGCCG-CAGCTTCCCAG 3' [SEQ ID NO: 52]. Preferably, the probe is labeled with FAM and quenched with BHQ-1.

Still further provided is a kit for amplification of CMV nucleic acid sequences in a sample. The kit comprises (i) a set of primers comprising a pair of forward and reverse primers for amplification of a CMV UL34 nucleic acid sequence and a pair of forward and reverse primers for amplification of a CMV UL80.5 nucleic acid sequence and (ii) instructions for using the set of primers in the amplification of CMV nucleic acid sequences and/or one or more reagents for using the sets of primers in the amplification of CMV nucleic acid sequences. The pair of forward and reverse primers for amplification of a CMV UL34 nucleic acid sequence can amplify a nucleic acid sequence in the region from about nucleotide 29 to about nucleotide 79 of the UL34 CDS, and the pair of forward and reverse primers for amplification of a CMV UL80.5 nucleic acid sequence can amplify a nucleic acid sequence in the region from about 2025 to about 2080 of the UL80.5 CDS. One of the pair of primers for amplification of a UL34 nucleic acid sequence can specifically hybridize to the UL34 CDS in the region from about nucleotide 2 to about nucleotide 29, and the other of the pair of primers for amplification of a UL34 nucleic acid sequence can specifically hybridize to the UL34 CDS in the region from about nucleotide 78 to about nucleotide 106. One of the pair of primers for amplification of a UL80.5 nucleic acid sequence can specifically hybridize to the UL80.5 CDS in the region from about 2025 to about 2025, and the other of the pair of primers for amplification of a UL80.5 nucleic acid sequence can specifically hybridize to the UL80.5 CDS in the region from about nucleotide 2078 to about nucleotide 2105. The primers for amplification of a UL34 nucleic acid sequence can comprise, or consist essentially of, (i) 5' TGA ACT TCA TCA TCA CCA CCC GAG ACT 3' [SEQ ID NO: 49] as a forward primer, and (ii) 5' CCT TGT ACG CTT TGG AAA TCG AGC CTG 3' [SEQ ID NO: 50] as a reverse primer, and the primers for amplification of a UL80.5 nucleic acid sequence can comprise, or consist essentially of, (i') 5' CGG CTA GTG TCG TGT TAG C 3' [SEQ ID NO: 16] as a forward primer, and (ii') 5' CAC AAA AAT CCG CCG ATT CAG ATC 3' [SEQ ID NO: 47] as a reverse primer. The kit can further comprise (i) a probe for detection of amplification of a CMV UL34 nucleic acid sequence and a probe for detection of amplification of a CMV UL80.5 nucleic acid sequence and (ii) instructions for using the probes in the detection of amplification of CMV nucleic acid sequences and/or one or more reagents for using the probes in the detection of amplification of CMV nucleic acid sequences. The probe for detection of amplification of a UL34 nucleic acid sequence can specifically hybridize to the UL34 CDS in the region from about nucleotide 29 to about nucleotide 79, and the probe for detection of amplification of a UL80.5 nucleic acid sequence can specifically hybridize to the UL80.5 CDS in the region from about 2025 and about 2080. The probe for detection of amplification of a UL34 nucleic acid sequence can specifically hybridize to the UL34 CDS in the region from about nucleotide 33 to about nucleotide 59, and the probe for detection of amplification of a UL80.5 nucleic acid sequence can specifically hybridize to the UL80.5 CDS in the region from about nucleotide 2040 to about nucleotide 2062. The nucleotide sequence of the probe for detection of amplification of a UL34 nucleic acid sequence can comprise, or consist essentially of 5' CG ACG ATT CAG TCC TGC GAG CC 3' [SEQ ID NO: 51], and the nucleotide sequence of the probe for detection of amplification of a UL80.5 nucleic acid sequence can comprise, or consist essentially of 5'AAGCCGCCG-CAGCTTCCCAG 3' [SEQ ID NO: 52]. The probe is preferably labeled with FAM and quenched with BHQ-1.

BRIEF DESCRIPTION OF THE FIGURES

FIG. 1a-FIG. 1c is an alignment of publically available sequences for CMV UL34. The sequences were aligned to maximize sequence homology and identify regions free of mutations for design of primers and probes. CMV Merlin is available from GenBank as Accession No. AY446894.2 [SEQ ID NO: 61], CMV AD169 is available from GenBank as Accession No. X17403.1 [SEQ ID NO: 62], CMV Towne is available from GenBank as Accession No. AY315197.2 [SEQ ID NO: 63], CMV Toledo is available from GenBank as Accession No. AC146905.1 [SEQ ID NO: 64], CMV FIX is available from GenBank as Accession No. AC146907.1 [SEQ ID NO: 65], CMV PH is available from GenBank as Accession No. AC146904.1 [SEQ ID NO: 66], CMV TB40/E is available from GenBank as Accession No. EF999921.1 [SEQ ID NO: 67], and CMV TR is available from GenBank as Accession No. AC146906.1 [SEQ ID NO: 68].

FIG. 2a-FIG. 2e is an alignment of publically available sequences for CMV UL80.5. The sequences were aligned to maximize sequence homology and identify regions free of mutations for design of primers and probes. CMV Merlin is available from GenBank as Accession No. AY446894.2 [SEQ ID NO: 69], CMV AD169 is available from GenBank as Accession No. X17403.1 [SEQ ID NO: 70], CMV Towne is available from GenBank as Accession No. AY315197.2 [SEQ ID NO: 71], CMV Toledo is available from GenBank as Accession No. AC146905.1 [SEQ ID NO: 72], CMV FIX is available from GenBank as Accession No. AC146907.1 [SEQ ID NO: 73], CMV PH is available from GenBank as Accession No. AC146904.1 [SEQ ID NO: 74], CMV TB40/E is available from GenBank as Accession No. EF999921.1 [SEQ ID NO: 75], and CMV TR is available from GenBank as Accession No. AC146906.1 [SEQ ID NO: 76].

DETAILED DESCRIPTION

The present disclosure is predicated, at least in part, on the discovery of targets in CMV for amplification and quantitation. The targets are in genes that are essential for viral replication and/or survival, are sufficiently unique for CMV as compared to other herpes viruses, are not known or potential future drug targets, and are highly conserved. The targets are UL34, which is essential for CMV replication (see, e.g., Dunn et al. (2003), supra), and UL80.5, which is essential for capsid assembly (see, e.g., Gibson (2008), supra).

Definitions

The following terms are relevant to the present disclosure:

"About" refers to approximately a +/−10% variation from the stated value. It is to be understood that such a variation is always included in any given value provided herein, whether or not specific reference is made to it.

"Antigenemia" and "pp 65 antigenemia" are used interchangeably herein to refer to the detection of CMV pp 65 in leukocytes.

"CMV infection" is used herein to refer to isolation of the CMV virus or detection of CMV components, such as proteins or nucleic acids, in a bodily fluid or tissue specimen. The source of the specimen can be any suitable specimen including, but not limited to, whole blood, plasma, serum, peripheral blood leukocytes, cerebrospinal fluid, and urine. A "primary CMV infection" is used herein to refer to isolation of the CMV virus or detection of CMV components or anti-CMV antibodies (provided that passive transfer of antibodies via blood products and the like can be excluded) in a patient that was previously sero-negative for CMV. A "recurrent CMV infection" is used herein to refer to isolation of the CMV virus or detection of CMV components in a patient that was previously infected with CMV but had no detectable virus for a specified period of time, such as at least four weeks, during active surveillance. A recurrent CMV infection may result from reactivation of latent, i.e., endogenous, virus or re-infection (i.e., with exogenous virus). "Reinfection" is used herein to refer to the detection of a strain of CMV in a patient that is distinct from the strain of CMV that caused the primary infection in the patient. "Reactivation" is used herein to refer to the detection of a strain of CMV in a patient that is indistinguishable from the strain of CMV that caused the primary infection in the patient. Humar et al. (Amer. J. Transplant. 6: 262-274 (2006)) have proposed that "CMV active infection" be defined for trials of immunosuppressive agents as replicative infection diagnosed by growing the virus in vitro, finding evidence of viral infection by intra-cytoplasmic or intra-nuclear inclusions or by antibody-based staining of histopathologic sections or finding evidence of replication using nucleic acid based assays or antigenemia studies. Similarly, Kotton et al. (Transplantation 89(7): 779-795 (Apr. 15, 2010)) have defined "CMV infection" as evidence of CMV replication regardless of symptoms (consistent with the American Society of Transplantations recommendations for use in clinical trials (Humar et al. (2006), supra). Humar et al. ((2006), supra) have further proposed that "CMV disease" be defined for trials of immunosuppressive agents as evidence of CMV infection with attributable symptoms, wherein CMV disease can be sub-classified into CMV viral syndrome or tissue invasive disease. Similarly, Kotton et al. ((2010), supra) have defined "CMV disease" as evidence of CMV infection with attributable symptoms, wherein CMV disease can be sub-classified into CMV viral syndrome, when fever, malaise, leukopenia, and thrombocytopenia are present, or tissue-invasive disease (consistent with the American Society of Transplantation recommendations for use in clinical trials (Humar et al. (2006), supra)).

"Control" refers to a composition known to not contain an analyte ("negative control"), such as CMV nucleic acid, or to contain an analyte ("positive control"). A positive control can comprise a known concentration of an analyte, such as CMV nucleic acid. "Control," "positive control," and "calibrator" may be used interchangeably herein to refer to a composition comprising a known concentration of an analyte. A "positive control" can be used to establish assay performance characteristics and is a useful indicator of the integrity of reagents (e.g., analytes). An "internal control," as used herein, is a non-CMV nucleic acid added to the reaction mixture. Amplification of the internal control is a useful indicator of the integrity of the amplification.

"DNAemia" is used herein to refer to the detection of DNA in samples of plasma, whole blood, and isolated peripheral blood leukocytes or in buffy-coat specimens.

"FCN" is a quantitative cycle number associated with position of the maxRatio curve peak (Abbott Molecular, Inc., Des Plaines, Ill.).

"Label" and "detectable label" mean a moiety attached to a probe to render the hybridization between the probe and the analyte, e.g., CMV nucleic acid, in particular amplified CMV nucleic acid, detectable, and the probe so labeled is referred to as "detectably labeled." A label can produce a signal that is detectable by visual or instrumental means. In this regard, the moiety, itself, may not be detectable but may become detectable upon reaction with yet another moiety. Use of the term "detectably labeled" is intended to encompass such labeling.

"maxRatio" or "MR" is used herein to refer to the maxRatio method of (Abbott Molecular, Inc., Des Plaines, Ill.) independent curve shape analysis of a real-time PCR curve. The maxRatio curve is generated by taking successive ratios of the signal generated from the PCR curve. When the real-time amplification curve is in its exponential phase, a large change occurs in the ratio curve creating a peak. The location of the peak in cycles is the FCN cycle number. MR is a measure of the relative reaction efficiency associated with the height of the ratio curve peak. The width of the ratio curve peak at one-half of the MR value is a measure of reaction normality or abnormality.

"Nucleic acid sequence-based amplification" or "NASBA" is the amplification, i.e., the generation of multiple copies, of a specific nucleic acid sequence, such as a specific DNA or RNA sequence, which is present in a sample at a low copy number. Amplification techniques include polymerase chain reaction (PCR), real-time PCR, transcription-mediated amplification (TMA), ligase chain reaction (LCR), strand displacement amplification (SDA), and the like. Real-time PCR is preferred in the context of the present disclosure. Certain amplification techniques may require primer modification.

"Preemptive therapy" is used herein to refer to the initiation of antiviral therapy when regular period laboratory monitoring detects early, asymptomatic viral replication (i.e., once viral replication reaches a certain assay threshold) so as to prevent progression to clinical disease. See, e.g., Kotton et al. (2010), supra, for further discussion.

"Prophylaxis" is used herein to refer to the administration of antiviral medication to a patient, who has not been identified as "at risk" for CMV infection or who has been identified as "at risk" for CMV infection. Administration of anti-viral medication is usually begun in the immediate or very early post-transplant period and continued for a finite period of time, often in the range of 3-6 months. Examples of anti-viral medications include acyclovir, valacyclovir, intravenous ganciclovir, oral ganciclovir, and valganciclovir. See, e.g., Kotton et al. (2010), supra, for further discussion.

"Specifically hybridize(s)," as used herein, refers to the ability of a given nucleic acid, such as a primer or probe, to bind specifically to another nucleic acid, e.g., a CMV nucleic acid.

The terminology used herein is for the purpose of describing particular embodiments only and is not otherwise intended to be limiting.

Methods of Amplifying and Detecting CMV

A method of amplifying cytomegalovirus (CMV) nucleic acid sequences in a sample is provided. The method comprises (a) forming a mixture comprising the sample, nucleic acid amplification reagents, a pair of primers for amplification of a UL34 nucleic acid sequence, and a pair of primers for amplification of a UL80.5 nucleic acid sequence, and (b) subjecting the mixture to conditions that promote amplification of the UL34 nucleic acid sequence and the UL80.5 nucleic acid sequence.

Nucleic acid amplification reagents include an enzyme having polymerase activity (e.g., AmpliTaq Gold®), one or more enzyme co-factors (e.g., $MgCl_2$), and deoxynucleotide triphosphates (dNTPs; e.g., dATP, dGTP, dCTP, and dTTP). Preferred concentrations of nucleic acid amplification reagents are exemplified herein.

Conditions that promote amplification are those that promote annealing of primers and extension of nucleic acid sequences. Annealing is dependent on various parameters, such as temperature, ionic strength, length of sequences being amplified, complementarity, and G:C content of the sequences being amplified. For example, lowering the temperature promotes annealing of complementary nucleic acid sequences. High G:C content and longer length stabilize duplex formation. Generally, primers and probes of about 30 bp or less and having a high G:C content work well. Preferred amplification conditions, primers and probes are exemplified herein.

Step (b) can be repeated any suitable number of times by thermal cycling the reaction mixture between about 10 and about 100 times, such as between about 20 and about 75 times, such as between about 25 and about 50 times.

The primers for amplification of a UL34 nucleic acid sequence amplify a nucleic acid sequence in the region from about nucleotide 29 to about nucleotide 79 of the UL34 coding domain sequence (CDS; all references to nucleotide positions are made with reference to the Merlin strain of CMV (GenBank Accession No. AY446894.2)). One of the pair of primers for amplification of a UL34 nucleic acid sequence specifically hybridizes to the UL34 CDS in the region from about nucleotide 2 to about nucleotide 29, and the other of the pair of primers for amplification of a UL34 nucleic acid sequence specifically hybridizes to the UL34 CDS in the region from about nucleotide 78 to about nucleotide 106. The primers for amplification of a UL34 nucleic acid sequence can comprise, or consist essentially of, and preferably do comprise or consist essentially of, (i) 5' TGA ACT TCA TCA TCA CCA CCC GAG ACT 3' [SEQ ID NO: 49] as a forward primer, and (ii) 5' CCT TGT ACG CTT TGG AAA TCG AGC CTG 3' [SEQ ID NO: 50] as a reverse primer.

The primers for amplification of a UL80.5 nucleic acid sequence amplify a nucleic acid sequence in the region from about 2025 to about 2080 of the UL80.5 CDS. One of the pair of primers for amplification of a UL80.5 nucleic acid sequence specifically hybridizes to the UL80.5 CDS in the region from about 2005 to about 2025, and the other of the pair of primers for amplification of a UL80.5 nucleic acid sequence specifically hybridizes to the UL80.5 CDS in the region from about nucleotide 2078 to about nucleotide 2105. The primers for amplification of a UL80.5 nucleic acid sequence can comprise, or consist essentially of, and preferably do comprise or consist essentially of, (i) 5' CGG CTA GTG TCG TGT TAG C 3' [SEQ ID NO: 16] as a forward primer, and (ii) 5' CAC AAA AAT CCG CCG ATT CAG ATC 3' [SEQ ID NO: 47] as a reverse primer.

The mixture in (a) can, and preferably does, comprise an internal control (IC) nucleic acid and a pair of primers for amplifying the IC nucleic acid. When the mixture in (a) comprises an IC nucleic acid, the conditions in (b) also promote amplification of the IC nucleic acid.

The method can further comprise, and preferably does comprise, simultaneously or subsequently detecting the presence, amount or concentration of CMV in the sample. The detection of CMV in the sample enables quantitation of CMV viral load, and the like. When standard PCR is used, detection after amplification is complete, such as after using a labeled primer during amplification, by using a labeled primer as a labeled probe after amplification, or by using a labeled probe, which differs in sequence from the primers, after amplification for hybridization to the amplified target sequence; amplification products hybridized to labeled probes then can be separated and detected by other means, such as by using microparticles and labeled probes. When real-time PCR is used, the mixture in (a) further comprises nucleic acid detection reagents, such as a non-specific fluorescent dye that intercalates with any double-stranded DNA, for example, or a labeled sequence-specific DNA probe, which permits detection only after the probe hybridizes with its complementary DNA target, thereby enabling simultaneous amplification and detection. Preferably, labeled sequence-specific DNA probes are used, particularly given the simultaneous amplification of two different nucleic acid sequences in accordance with the present disclosure. When a detection probe is present in the mixture in (a) during amplification, the detection probe should be stable under the conditions that promote amplification, should not interfere with amplification, should bind to its target sequence under amplification conditions, and emit a signal only upon binding its target sequence. Examples of probe that are particularly well-suited in this regard include molecular beacon probes, TAQMAN® probes, and linear probes, such as those described by Abravaya et al. (U.S. Pat. App. Pub. No. 2005/0227257). The probes disclosed herein can form the loop region, alone or in further combination with part of the stem region, of a molecular beacon. The probes disclosed herein also can be used as linear probes with a fluorophore (e.g., FAM) at one end and a high-efficiency quencher, such as the Black Hole Quencher (BHQ®; BioSearch Technologies, Inc., Novato, Calif.), at the other end.

In view of the foregoing, the mixture in (a) can further comprise, and preferably does comprise, a probe for detection of amplification of a UL34 nucleic acid sequence and a probe for detection of amplification of a UL80.5 nucleic acid sequence. The probe for detection of amplification of a UL34 nucleic acid sequence specifically hybridizes to the UL34 CDS in the region from about nucleotide 29 to about nucleotide 79, such as in the region from about nucleotide 33 to about nucleotide 59. The nucleotide sequence of the probe for detection of amplification of a UL34 nucleic acid sequence can comprise, or consist essentially of, and preferably does comprise or consist essentially of, 5' CG ACG ATT CAG TCC TGC GAG CC 3' [SEQ ID NO: 51]. The probe for detection of amplification of a UL80.5 nucleic acid sequence specifically hybridizes to the UL80.5 CDS in the region from about 2025 to about 2080, such as in the region from about nucleotide 2040 to about nucleotide 2062. The nucleotide sequence of the probe for detection of amplification of a U134 nucleic acid sequence can comprise, or consist essentially of, and preferably does comprise or consist essentially of, 5'AAGC-CGCCGCAGCTTCCCAG 3' [SEQ ID NO: 52]. A preferred label for a probe is FAM, and a preferred quencher for a probe is BHQ-1.

The method can, and preferably does, further comprise detecting the presence, amount or concentration of an IC in the sample. The amplification and detection of the IC demonstrates that the process has proceeded correctly for each sample.

Any suitable biological sample can be used. Preferably, the biological sample is liquid. Preferred examples of liquid biological samples include, but are not limited to, whole blood and plasma. Preferably, the plasma or whole blood is preserved, such as by the addition of a chelating agent, e.g., ethylenediaminetetraacetic acid (EDTA) or a salt thereof, such as a disodium salt or a calcium disodium salt. A proteinase, such as proteinase K, preferably is added to the sample to digest unwanted proteins.

The sample may be prepared for assay using any suitable method as is known in the art. Desirably, the method extracts and concentrates nucleic acids. The method also desirably makes the target sequence accessible for amplification, and removes potential inhibitors of amplification from the extract.

The use of an automated sample preparation system, such as an automated sample preparation system designed to use magnetic microparticle processes for the purification of nucleic acids, can be preferred. An example of an automated sample preparation system is m2000sp, which is available from Abbott Laboratories, Abbott Park, Ill. Alternatively, plasma samples can be prepared using the m24sp automated sample preparation system (Abbott) or prepared manually. Automated sample preparation is preferred over manual preparation because it is more consistent.

The Abbott mSample Preparation System$_{DNA}$ (4×24 preps; Abbott) reagents lyse the virions, capture the nucleic acids, and wash the particles to remove unbound sample components. Proteinase K is included in the lysis step for plasma samples to digest proteins associated with the samples. The bound nucleic acids are eluted and transferred to a 96-well deep plate. The nucleic acids are then ready for amplification. An unrelated DNA sequence, which serves as an internal control (IC) to demonstrate that the process has proceeded correctly for each sample, is introduced into the sample preparation procedure and is processed along with the calibrators, controls, and specimens.

Amplification/detection can be carried out as known in the art, such as by use of the m2000rt instrument (Abbott Molecular Inc., Des Plaines, Ill.). The target DNA is amplified by DNA polymerase in the presence of deoxynucleotide triphosphates (dNTPs) and magnesium. The amplification reagent contains specific sets of amplification primers for CMV and, preferably, an IC. During PCR amplification, high temperature is used to separate the strands of double-stranded DNA. When the reaction is cooled to a temperature where DNA annealing can occur, the analyte-specific, single-stranded DNA oligonucleotide primers bind to the analyte DNA. The primers are extended by DNA polymerase, thereby making an exact copy of a short target stretch of the analyte DNA. The DNA polymerase is a thermophilic enzyme that has been modified in its active site by a molecule that renders it inactive. When the enzyme is heated prior to the initiation of PCR, the inhibitory molecule is cleaved from the enzyme, thereby allowing it to regain its activity. In this manner, the enzyme is only active at temperatures where specific DNA-DNA interactions occur. This greatly reduces non-specific PCR artifacts, such as primer dimers. During each round of thermal cycling, amplification products dissociate to single strands at high temperature, allowing primer annealing and extension as the temperature is lowered. Exponential amplification of the target is achieved through repeated cycling between high and low temperatures. Amplification of the CMV and, if present, the IC targets takes place simultaneously in the same reaction.

Two short sequences within the UL34 and UL80.5 genes of the CMV genome are targeted in accordance with the present disclosure. The regions are specific for CMV and are highly conserved among different strains of CMV. The redundancy in target amplification is designed to produce robust, accurate and sensitive amplification of CMV DNA.

Any suitable sequence can be used as the IC. A preferred IC target sequence is derived from the hydroxypyruvate reductase gene from *Cucurbita pepo* (pumpkin). The IC can be in the form of a linearized DNA plasmid, preferably in a buffer solution with carrier DNA. Optionally, a preservative, such as sodium azide and/or ProClin® 950, is included.

Single-stranded, linear DNA oligonucleotides, which are detectably labeled, are used as probes. The probes can be detectably labeled in accordance with methods known in the art. In this regard, any suitable label can be used. For example, a fluorescent moiety can be covalently linked to one end of the probe and a quenching moiety can be covalently linked to the other end. During each round of PCR amplification, the detectably labeled probes anneal to the amplified target DNA, if present. In the absence of target sequences, the probes adopt a conformation that brings the quencher close enough to the excited fluorophore to absorb its energy before it can be fluorescently emitted. When the probe binds to its complementary sequence in the target, the fluorophore and the quencher are held apart, allowing fluorescent emission and detection. Preferably, the CMV-specific probes and the IC-specific probes are labeled differently so that CMV DNA and IC DNA can be distinguished. Since the fluorescence occurs during every cycle, the PCR reaction can be read in real-time. The amplification cycle at which fluorescent signal is detected is inversely proportional to the log of the CMV DNA concentration present in the original sample.

Primers and Probes

A set of primers, which comprises a pair of forward and reverse primers for amplification of a CMV UL34 nucleic acid sequence and a pair of forward and reverse primers for amplification of a CMV UL80.5 nucleic acid sequence, is also provided. The pair of forward and reverse primers for amplification of a CMV UL34 nucleic acid sequence amplify a nucleic acid sequence in the region from about nucleotide 29 to about nucleotide 79 of the UL34 CDS. The pair of forward and reverse primers for amplification of a CMV UL80.5 nucleic acid sequence amplifies a nucleic acid sequence in the region from about 2025 to about 2080 of the UL80.5 CDS. One of the pair of primers for amplification of a UL34 nucleic acid sequence specifically hybridizes to the UL34 CDS in the region from about nucleotide 2 to about nucleotide 29, and the other of the pair of primers for amplification of a UL34 nucleic acid sequence specifically hybridizes to the UL34 CDS in the region from about nucleotide 78 to about nucleotide 106. One of the pair of primers for amplification of a UL80.5 nucleic acid sequence specifically hybridizes to the UL80.5 CDS in the region from about 2005 to about 2025, and the other of the pair of primers for amplification of a UL80.5 nucleic acid sequence specifically hybridizes to the UL80.5 CDS in the region from about nucleotide 2078 to about nucleotide 2105. The primers for amplification of a UL34 nucleic acid sequence can comprise, or consist essentially of, and preferably do comprise or consist essentially of, (i) 5' TGA ACT TCA TCA TCA CCA CCC GAG ACT 3' [SEQ ID NO: 49] as a forward primer, and (ii) 5' CCT TGT ACG CTT TGG AAA TCG AGC CTG 3' [SEQ ID NO: 50] as a reverse primer. The primers for amplification of a UL80.5 nucleic acid sequence can comprise, or consist essentially of, and preferably do comprise or consist essentially of, (i') 5' CGG CTA GTG TCG TGT TAG C 3' [SEQ ID NO: 16] as a forward primer, and (ii') 5' CAC AAA AAT CCG CCG ATT CAG ATC 3' [SEQ ID NO: 47] as a reverse primer.

A set of probes, which comprises a probe for detection of amplification of a CMV UL34 nucleic acid sequence and a probe for detection of amplification of a CMV UL80.5 nucleic acid sequence, is also provided. The probe for detection of amplification of a UL34 nucleic acid sequence specifically hybridizes to the UL34 CDS in the region from about nucleotide 29 to about nucleotide 79, and the probe for detection of amplification of a UL80.5 nucleic acid sequence specifically hybridizes to the UL80.5 CDS in the region from about 2025 and about 2080. The probe for detection of amplification of a UL34 nucleic acid sequence specifically hybridizes to the UL34 CDS in the region from about nucleotide 33 to about nucleotide 59, and the probe for detection of amplification of a UL80.5 nucleic acid sequence specifically hybridizes to the UL80.5 CDS in the region from about nucleotide 2040 to about nucleotide 2062. The nucleotide sequence of the probe for detection of amplification of a UL34 nucleic acid sequence can comprise, or consist essentially of, and preferably does comprise or consist essentially of, 5' CG ACG ATT CAG TCC TGC GAG CC 3' [SEQ ID NO: 51]. The nucleotide sequence of the probe for detection of amplification of a UL80.5 nucleic acid sequence can comprise, or consist essentially of, and preferably does comprise or consist essentially of, 5'AAGCCGCCGCAGCTTCCCAG 3' [SEQ ID NO: 52]. Such probes not only enable the detection of the presence of CMV in a sample, but also enable the determination of the amount or concentration of CMV (i.e., quantitation) in a sample.

Primers and probes can be prepared by conventional techniques, such as solid-phase synthesis using commercially available equipment (see, e.g., Applied Biosystems, Inc. (Foster City, Calif.), DuPont (Wilmington, Del.), and Milligen (Bedford, Mass.)). While the primers and probes have been described herein in the context of their use in nucleic acid-based amplification methods, such as PCR, in particular real-time PCR, such primers and probes can be useful as probes in other nucleic acid-based methods, such as hybridization techniques (e.g., membrane-based hybridization techniques (Southern blots and Northern blots), modified nucleic acid hybridization techniques (see, e.g., Pandian et al., U.S. Pat. No. 5,627,030), and enzyme-linked immunoadsorbent assay (ELISA)-like techniques), which are used to detect identical, similar and complementary polynucleotide sequences.

The probes, which are single-stranded, linear DNA oligonucleotides, are detectably labeled in accordance with methods known in the art. Any suitable label can be used. For example, a fluorescent moiety can be covalently linked to one end of the probe and a quenching moiety can be covalently linked to the other end. Examples of suitable fluorophores include, but are not limited to, FAM, fluorescein and derivatives thereof, coumarin and derivatives thereof, Lucifer yellow, TEXAS RED®, tetramethylrhodamine, tetrachloro-6-carboxyfluoroscein, 5-carboxyrhodamine, and cyanine dyes (e.g., Cy5) and derivatives thereof. FAM is a preferred label. Examples of quenchers include DABCYL, DABSYL, DABMI, tetramethylrhodamine, TAMRA, and BHQ® dyes. As indicated above under "Methods of Amplifying and Detecting CMV," during each round of real-time PCR amplification, the detectably labeled probes anneal to the amplified target DNA, if present. In the absence of a target sequence, each of the probes adopts a conformation that brings the quencher close enough to the excited fluorophore to absorb its energy before it can be fluorescently emitted. In the presence of a target sequence, each probe binds to its complementary sequence in the target and the fluorophore and the quencher are held apart, allowing fluorescent emission and detection. Preferably, the CMV-specific probes and the IC-specific probes are labeled differently so that CMV DNA and IC DNA can be distinguished. In this regard, the CMV-specific probe(s) is/are preferably labeled with FAM and quenched with BHQ-1.

Kits

A kit for amplification of CMV nucleic acid sequences in a sample is provided. The kit comprises (i) a set of primers comprising a pair of forward and reverse primers for amplification of a CMV UL34 nucleic acid sequence and a pair of forward and reverse primers for amplification of a CMV UL80.5 nucleic acid sequence and (ii) instructions for using the set of primers in the amplification of CMV nucleic acid sequences and/or one or more reagents for using the set of primers in the amplification of CMV nucleic acid sequences. The pair of forward and reverse primers for amplification of a CMV UL34 nucleic acid sequence amplify a nucleic acid sequence in the region from about nucleotide 29 to about nucleotide 79 of the UL34 CDS, and the pair of forward and reverse primers for amplification of a CMV UL80.5 nucleic acid sequence amplify a nucleic acid sequence in the region from about 2025 to about 2080 of the UL80.5 CDS. One of the pair of primers for amplification of a UL34 nucleic acid sequence specifically hybridizes to the UL34 CDS in the region from about nucleotide 2 to about nucleotide 29, and the other of the pair of primers for amplification of a UL34 nucleic acid sequence specifically hybridizes to the UL34 CDS in the region from about nucleotide 78 to about nucleotide 106. One of the pair of primers for amplification of a UL80.5 nucleic acid sequence specifically hybridizes to the UL80.5 CDS in the region from about 2005 to about 2025, and the other of the pair of primers for amplification of a UL80.5 nucleic acid sequence specifically hybridizes to the UL80.5 CDS in the region from about nucleotide 2078 to about nucleotide 2105. The primers for amplification of a UL34 nucleic acid sequence can comprise, or consist essentially of, and preferably do comprise or consist essentially of, (i) 5' TGA ACT TCA TCA TCA CCA CCC GAG ACT 3' [SEQ ID NO: 49] as a forward primer, and (ii) 5' CCT TGT ACG CTT TGG AAA TCG AGC CTG 3' [SEQ ID NO: 50] as a reverse primer. The primers for amplification of a UL80.5 nucleic acid sequence can comprise, or consist essentially of, and preferably do comprise or consist essentially of, (i') 5' CGG CTA GTG TCG TGT TAG C 3' [SEQ ID NO: 16] as a forward primer, and (ii') 5' CAC AAA AAT CCG CCG ATT CAG ATC 3' [SEQ ID NO: 47] as a reverse primer.

The kit can further comprise, and preferably does comprise, (i) a probe for detection of amplification of a CMV UL34 nucleic acid sequence and a probe for detection of amplification of a CMV UL80.5 nucleic acid sequence and (ii) instructions for using the probes in the detection of amplification of CMV nucleic acid sequences and/or one or more reagents for using the probes in the detection of amplification of CMV nucleic acid sequences. The probe for detection of amplification of a UL34 nucleic acid sequence specifically hybridizes to the UL34 CDS in the region from about nucleotide 29 to about nucleotide 79, such as from about nucleotide 33 to about nucleotide 59. The probe for detection of amplification of a UL80.5 nucleic acid sequence specifically hybridizes to the UL80.5 CDS in the region between about 2025 and about 2080, such as from about nucleotide 2040 to about nucleotide 2062. The nucleotide sequence of the probe for detection of amplification of a UL34 nucleic acid sequence can comprise, or consist essentially of, and preferably does comprise or consist essentially of, 5' CG ACG ATT CAG TCC TGC GAG CC 3' [SEQ ID NO: 51]. The nucleotide sequence of the probe for detection of amplification of a UL80.5 nucleic acid sequence can comprise, or consist essentially of, and preferably does comprise or consist essentially of, 5'AAGCCGCCGCAGCTTCCCAG 3' [SEQ ID NO: 52]. A preferred label for a probe is FAM. In this regard, the label FAM is preferably used in combination with the quencher BHQ-1.

The kit can further comprise dNTPs. Preferably, the dNTPs are supplied in a buffered solution with a reference dye.

The primers, probes and dNTPs can be packaged in various configurations. Preferably, the primers, probes and dNTPS are in a single container. The container preferably also contains a preservative, such as sodium azide and/or ProClin® 950.

The kit can further comprise a DNA polymerase. Any suitable DNA polymerase can be used. An example of a preferred DNA polymerase is AmpliTaq Gold® (Life Technologies Corp., Carlsbad, Calif.). The DNA polymerase can be supplied in a buffered solution, which optionally contains, and preferably does contain, stabilizers.

The kit can further comprise an activation reagent, such as magnesium chloride, in a buffered solution. The buffered solution preferably includes a preservative, such as sodium azide and/or ProClin® 950.

The kit can optionally further comprise an IC. The IC is an unrelated DNA sequence that demonstrates that the process has proceeded correctly for each sample. Any suitable sequence can be used as the IC. A preferred IC target sequence is derived from the hydroxypyruvate reductase gene from *Cucurbita* pepo (pumpkin). The IC can be in the form of a linearized DNA plasmid, preferably in a buffer solution with carrier DNA. Optionally, a preservative, such as sodium azide and/or ProClin® 950, is included. The CMV-specific probes and the IC-specific probes are labeled differently so that CMV DNA and IC DNA can be distinguished. A preferred label for the IC-specific probe is NED. Preferably, the label NED is used in combination with the quencher BHQ-2.

A negative control also can be included in the kit. A negative control can contain carrier DNA in a buffered solution. Optionally, a preservative, such as sodium azide and/or ProClin® 950, is included.

A positive control also can be included in the kit. A positive control can contain inactivated CMV in human plasma, which is non-reactive by FDA-licensed tests for antibodies to HCV, HIV-1, HIV-2 and HBsAg. Optionally, a preservative, such as sodium azide and/or ProClin® 950, is included.

A calibrator also can be included in the kit. The calibrator can contain noninfectious, linearized CMV DNA plasmid in a buffer solution with carrier DNA. Optionally, a preservative, such as sodium azide and/or ProClin® 950, is included.

Applications

The materials and method described herein can be used to quantify viral load in whole blood (or plasma). Such quantification enables early detection of active CMV infection, close monitoring of a patient's response to anti-viral treatment, prediction of the risk of viremic relapse, emergence of resistant strains, and eventual development of CMV disease (Emery et al., Lancet 355: 2032-2036 (2000); and Razonable et al., J. Clin. Microbiol. 40: 746-752 (2002)). Monthly quantitative viral load assessment, at a minimum, is recommended in clinical trials evaluating new immunosuppressive regimens in transplant patients, with continued assessment for at least one year after transplant, and testing beyond that dependent on whether or not a prophylaxis regimen is employed and the nature of the regimen (Humar et al. (2006), supra). Donor and recipient should be screened by CMV serology prior to transplant.

Quantitative viral load assessment may be safely used for guiding pre-emptive therapy (Gema et al., Bone Marrow Transplant. 41: 873-879 (2008); Allice et al., J. Virol. Methods 148(1-2): 9-16 (March 2008; epub 11.28.07); Harrington et al., Bone Marrow Transplant. 39: 237-238 (2007); Lilleri et al., J. Med. Virol. 73: 412-418 (2004); Lilleri et al., Blood 110: 2757-2760 (2007); Ruell et al., Bone Marrow Transplant. 40: 55-61 (2007); and Verkruyse et al., Bone Marrow Transplant. 37: 51-56 (2006)). Two consecutive positive PCR tests performed on whole blood have been shown to be a clinically safe approach for triggering the initiation of preemptive therapy (Einsele et al., Blood 86: 2815-2820 (1995); and Lengerke et al., Bone Marrow Transplant. 38: 53-60 (2006)) but may lead to over-treatment (Gimeno et al. (2008), supra).

Currently, the international consensus guidelines on the management of CMV in solid organ transplantation include the following for diagnostics:

conduct pre-transplant donor and recipient serology; if recipient is negative, re-test at time of transplant; if pre-transplant serology is equivocal in recipient, assume it is negative; if pre-transplant serology is equivocal in donor, assume it is positive;

both antigenemia and quantitative nucleic acid testing (QNAT), i.e., viral load tests, are acceptable options for diagnosis, decisions regarding preemptive therapy, and monitoring response to therapy;

either plasma or whole blood is an acceptable specimen for QNAT with an appreciation of the differences in viral load values and viral kinetics in the two compartments; specimen type should not be changed when monitoring patients; and a universal cutoff for initiating therapy has not been established yet; individual laboratories should establish their own cutoffs and audit clinical outcomes to verify the cutoff used (Kotton et al. (2010), supra).

Currently, the international consensus guidelines on the management of CMV in solid organ transplantation include the following for preemptive therapy:

choose an appropriate threshold value for the specific assay being used;

for optimal preemptive therapy, kidney, pancreas, liver, and heart transplants should be monitored by CMV PCR or antigenemia every week for three months after transplant;

once the positive threshold is reached for the specific assay being used, therapy with treatment (not prophylactic) dose valganciclovir or intravenous ganciclovir should be started and continued until one or two negative tests are obtained; testing while on treatment is often performed once or twice per week; and whether to reinitiate subsequent monitoring or secondary antiviral prophylaxis after the end of treatment should be an institutional decision (Kotton et al. (2010), supra).

Currently, the international consensus guidelines on the management of CMV in solid organ transplantation include the following for CMV treatment:

weekly laboratory monitoring of CMV with a QNAT or antigenemia-based assay during the treatment phase to monitor response and the possible development of resistance;

two consecutive negative samples, preferably sampled one week apart, ensure viral clearance;

periodic viral load monitoring should also be performed during secondary prophylaxis; the correct time interval for monitoring is not known but more frequent monitoring should be done in those at high risk for breakthrough disease; and the lower limits of detection of QNAT assays are variable; therefore, "undetectable" is an assay-specific term; when using extremely sensitive viral load assays, which may detect latent virus, it is unknown if treatment to "undetectable" viral load is required (Kotton et al. (2010), supra).

Currently, the international consensus guidelines on the management of CMV in solid organ transplantation include the following for suspected CMV drug resistance:

suspect drug resistance if cumulative ganciclovir treatment is greater than six weeks and viral load increases, or disease progresses, after two weeks at full dose (Kotton et al. (2010), supra).

Currently, the international consensus guidelines on the management of CMV in solid organ transplantation include the following for pediatric patients:

donors, who are less than 18 months of age, should be regarded as CMV seropositive if the CMV serologic test is positive;

recipients, who are less than 18 months of age, should be regarded as CMV seronegative; and CMV urine culture of QNAT should be obtained from seropositive recipients less than 18 months of age; a positive result would confirm prior CMV exposure; negative CMV urine culture may result from intermittent shedding of virus (Kotton et al. (2010), supra).

Currently, there are no consensus guidelines on the management of CMV in bone marrow transplantation. Consequently, different transplant centers have their own institutional guidelines.

A pervasive issue in quantitative viral load assessment is which clinical specimen—plasma, whole blood, or leukocytes—is optimal. Recent data suggest plasma and whole blood are equally suitable for monitoring active CMV infection in allo-stem cell transplant recipients (Gimeno et al. (2008), supra)). In this regard, 1,000-10,000 copies/mL of whole blood has been suggested as a threshold for DNAemia (Gema (2008), supra; Harrington et al., Bone Marrow Transplant. 39: 237-238 (2007); Lilleri et al. (2007), supra; Ruell et al. (2007), supra; and Verkruyse et al., Bone Marrow Transplant. 37: 51-56 (2006)); 550 copies/mL of whole blood also has been suggested as a threshold for DNAemia (Gimeno et al. (2008), supra). Two hundred to 10,000 copies/mL of plasma has been suggested as a threshold for DNAemia, at least with regard to allogeneic stem cell transplant recipients (Kalpoe et al., J. Clin. Microbiol. 42: 1498-1504 (2004); Limaye et al., J. Infect. Dis. 183: 377-382 (2001); Mori et al., Bone Marrow Transplant. 29: 777-782 (2002); and Tanaka et al., Bone Marrow Transplant. 30: 315-319 (2002)). However, none of the suggested threshold levels has been clinically validated (Gimeno et al. (2008), supra). Gimeno et al. suggest a DNAemia level increase of 2.42 $\log_{10}$ (266 copies/mL) between two consecutive positive PCR samples drawn a median of one week apart is the optimal value for discriminating between patients who require pre-emptive therapy and those who do not (Gimeno et al. (2008), supra). Mullier et al. (Acta Clin. Belg. 64(6): 477-482 (November-December 2009)) has suggested a CMV real-time PCR clinical threshold of 1500 copies/mL for reactivation in transplant recipients. Choi et al. (J. Korean Med. Sci. 24(4): 571-578 (August 2009; epub Jul. 29, 2010)) has suggested CMV real-time PCR clinical thresholds for initiation of pre-emptive therapy of $2 \times 10^4$ copies/mL for hematopoietic stem cell transplant recipients with a high risk of CMV infection and $3 \times 10^4$ copies/mL for hematopoietic stem cell transplant recipients with a low risk of CMV infection.

Irrespective of when consensus guidelines are established, the materials and method of the present disclosure enable a level of detection of approximately 10 copies of CMV/mL of plasma and a level of detection of approximately 30 copies of CMV/mL of whole blood. In addition, potential cross-reactants (e.g., HSV-1, HSV-2, EBV, HHV-6A, HHV-6B, HHV-7, Kaposi's sarcoma-associated herpesvirus (KSHV)/HHV-8, Vaccinia virus, Varicella Zoster virus (VZV), BK human polyomavirus, *Chlamydia trachomatis, Neisseria gonorrhoeae, Candida albicans, Staphylococcus aureus, Staphylococcus epidermidis, Mycobacterium gordonae, Mycobacterium smegmatis*, HIV-1, HIV-2, HTLV-1, HPV-16, HPV-18, HBV, and HCV) at $1 \times 10^5$ cp/mL of CMV-negative control give negative results.

EXAMPLES

The following examples serve to illustrate the present disclosure. The examples are not intended to limit the scope of the claimed invention in any way.

Example 1

This example describes the criteria that were employed in the design and evaluation of CMV primer and probe sequences.

Figure 1A:
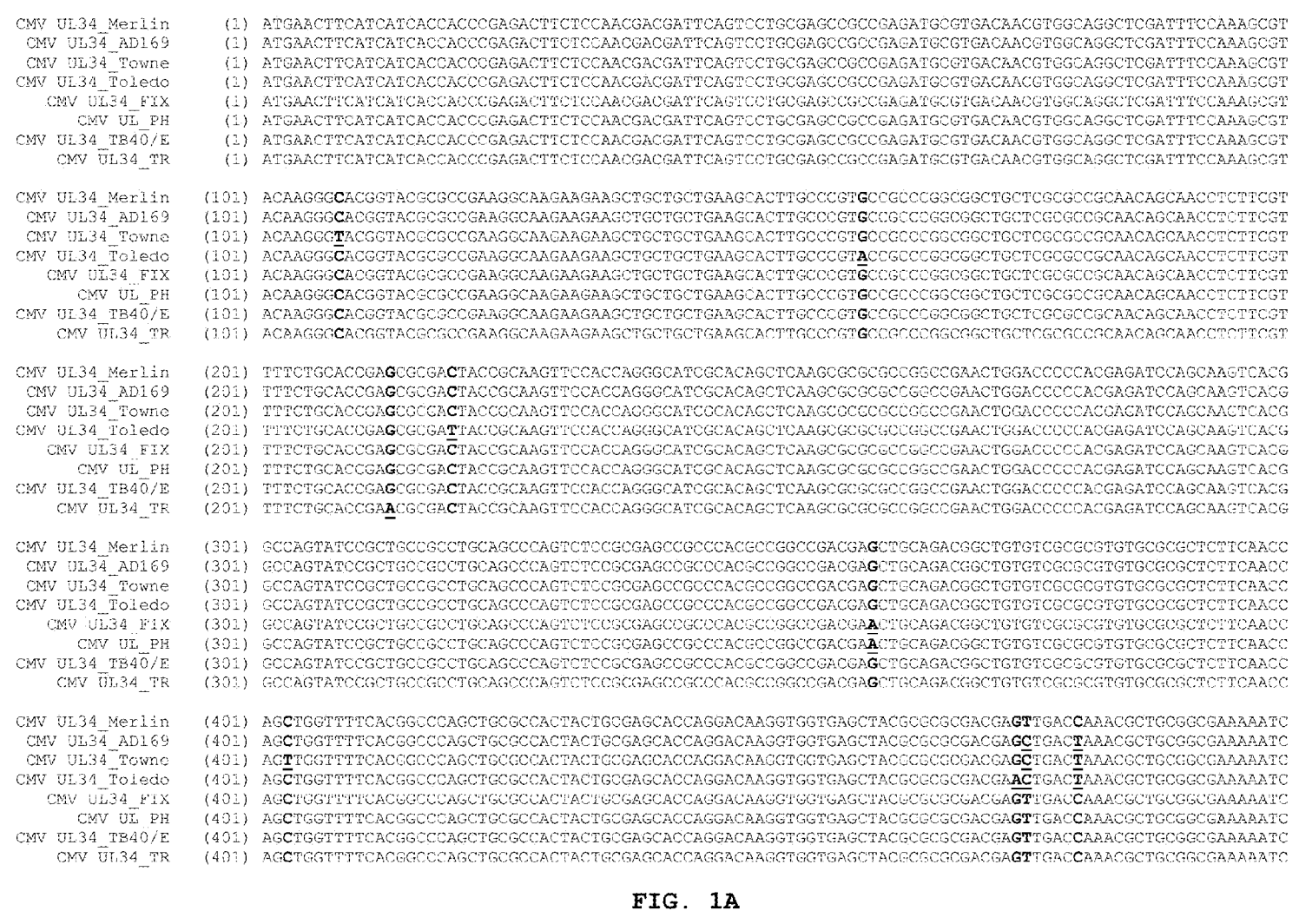
Figure 1B:
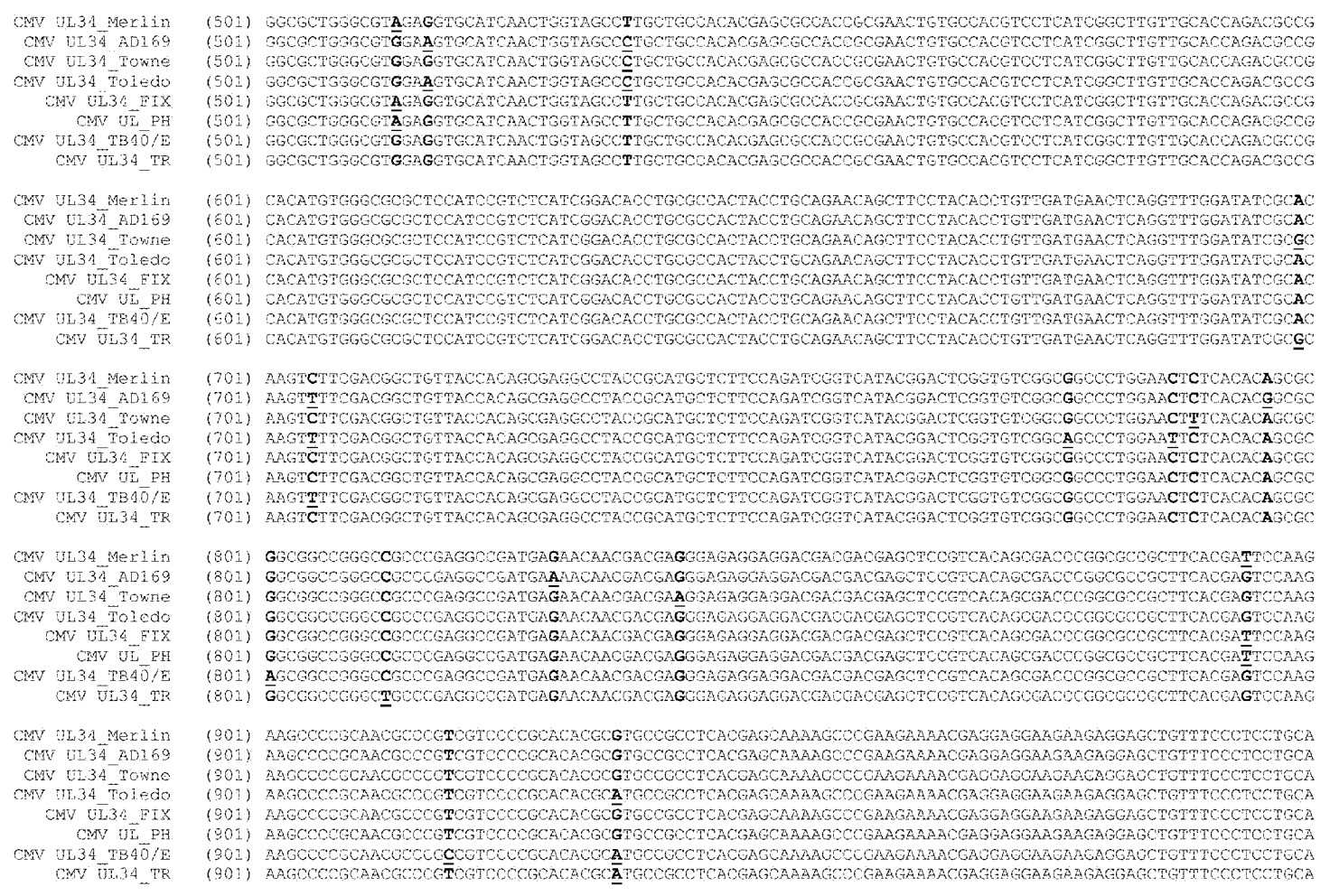
Figure 2A:
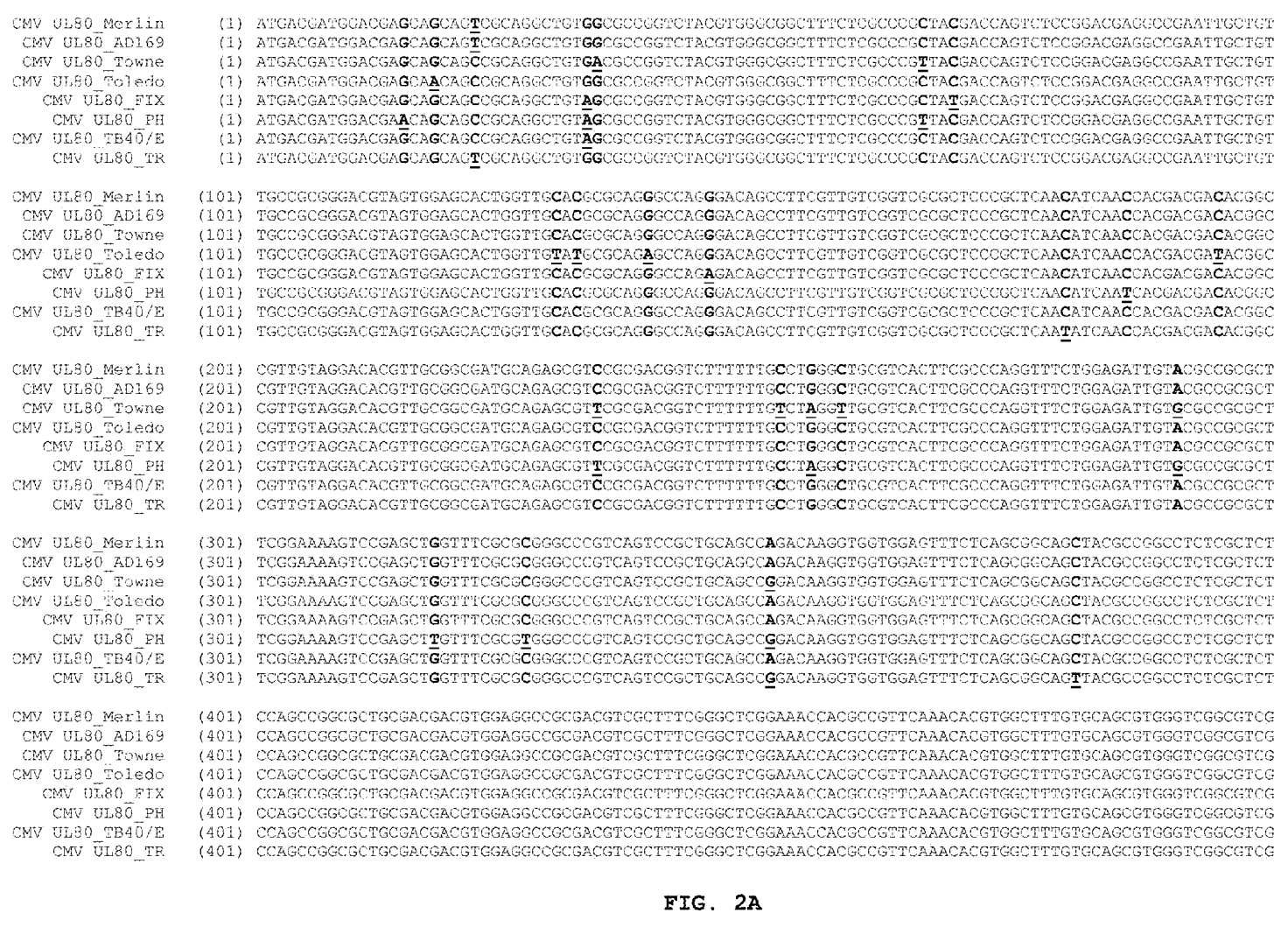
Figure 2B:
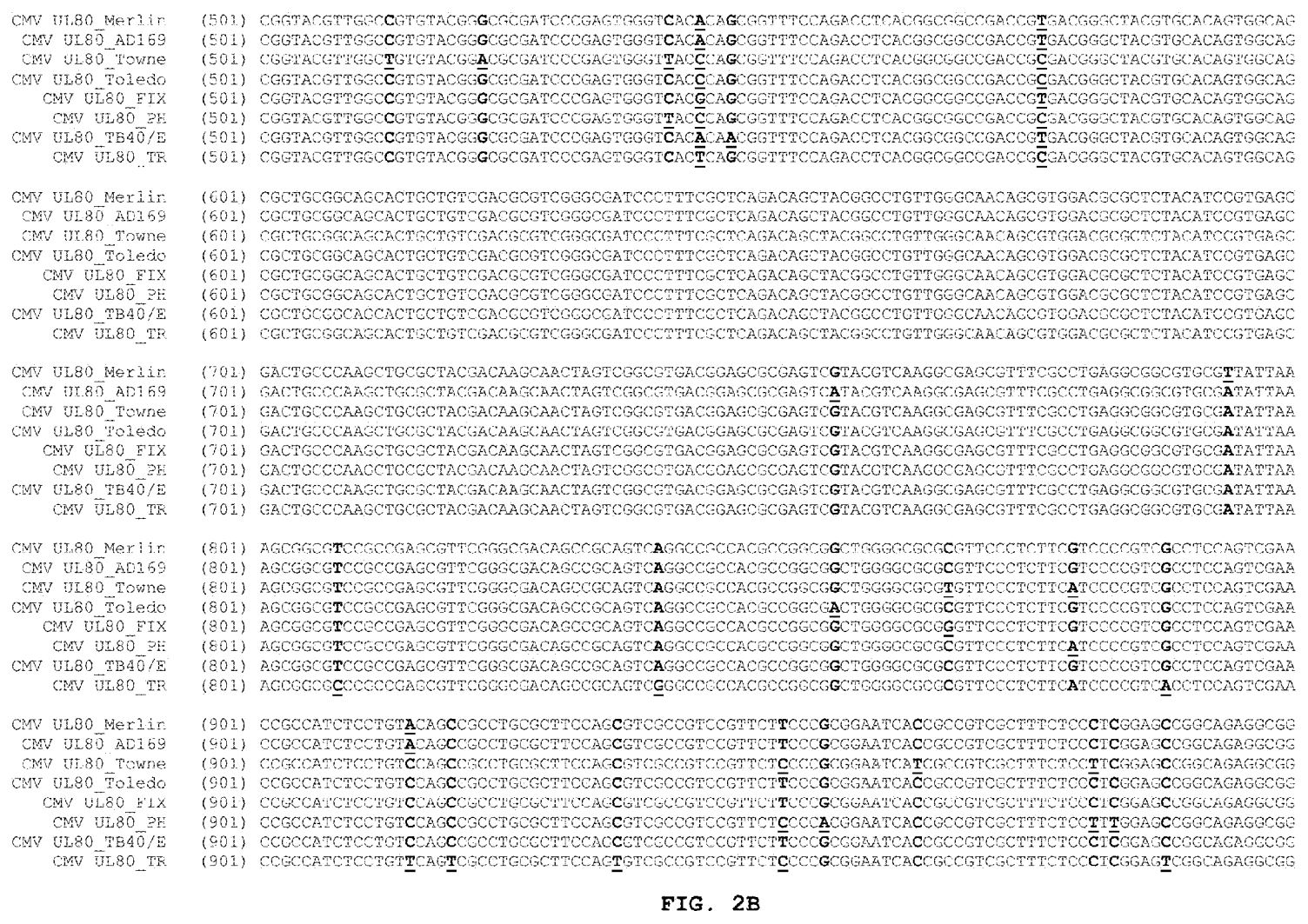
Figure 2C:
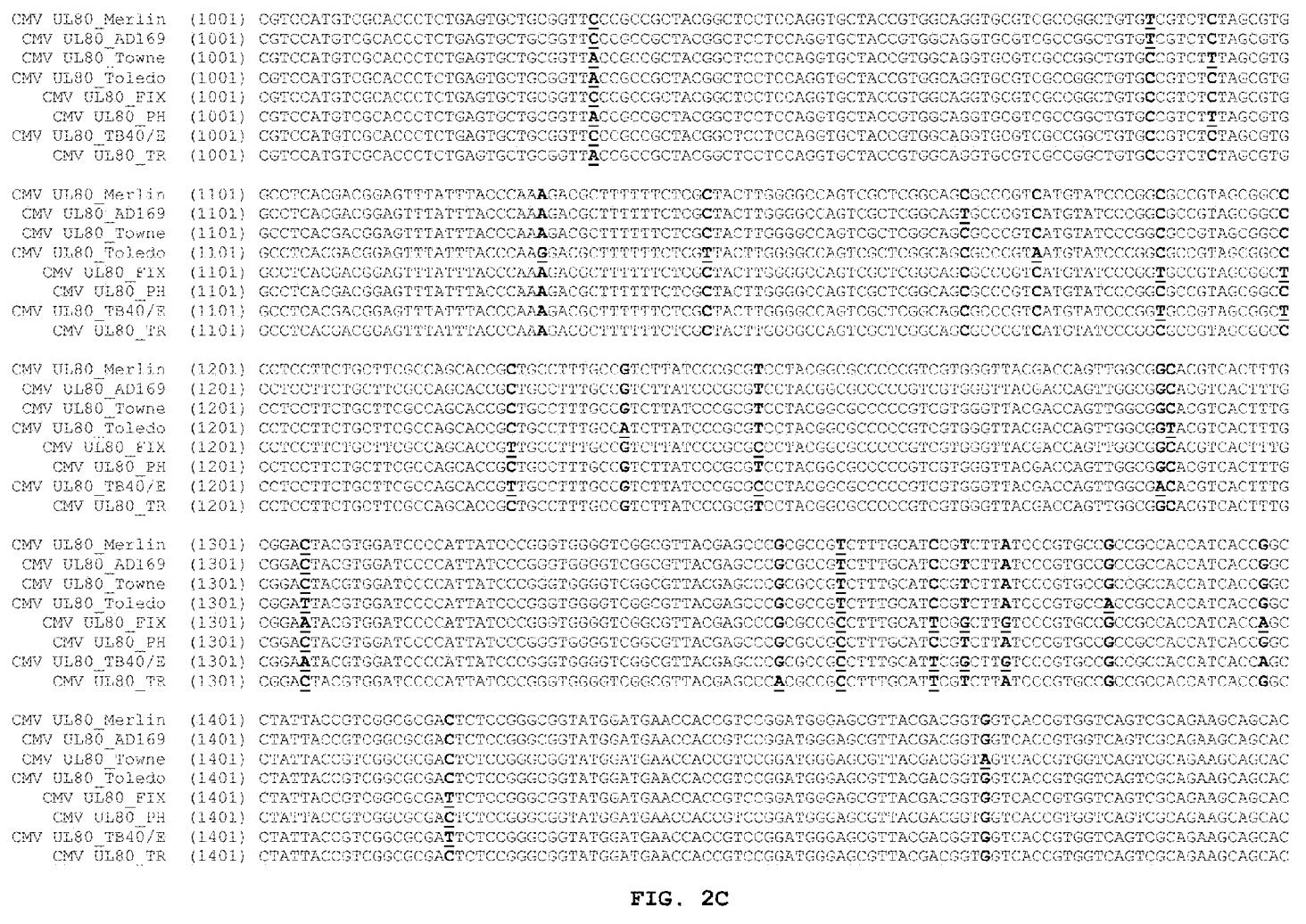
Figure 2D:
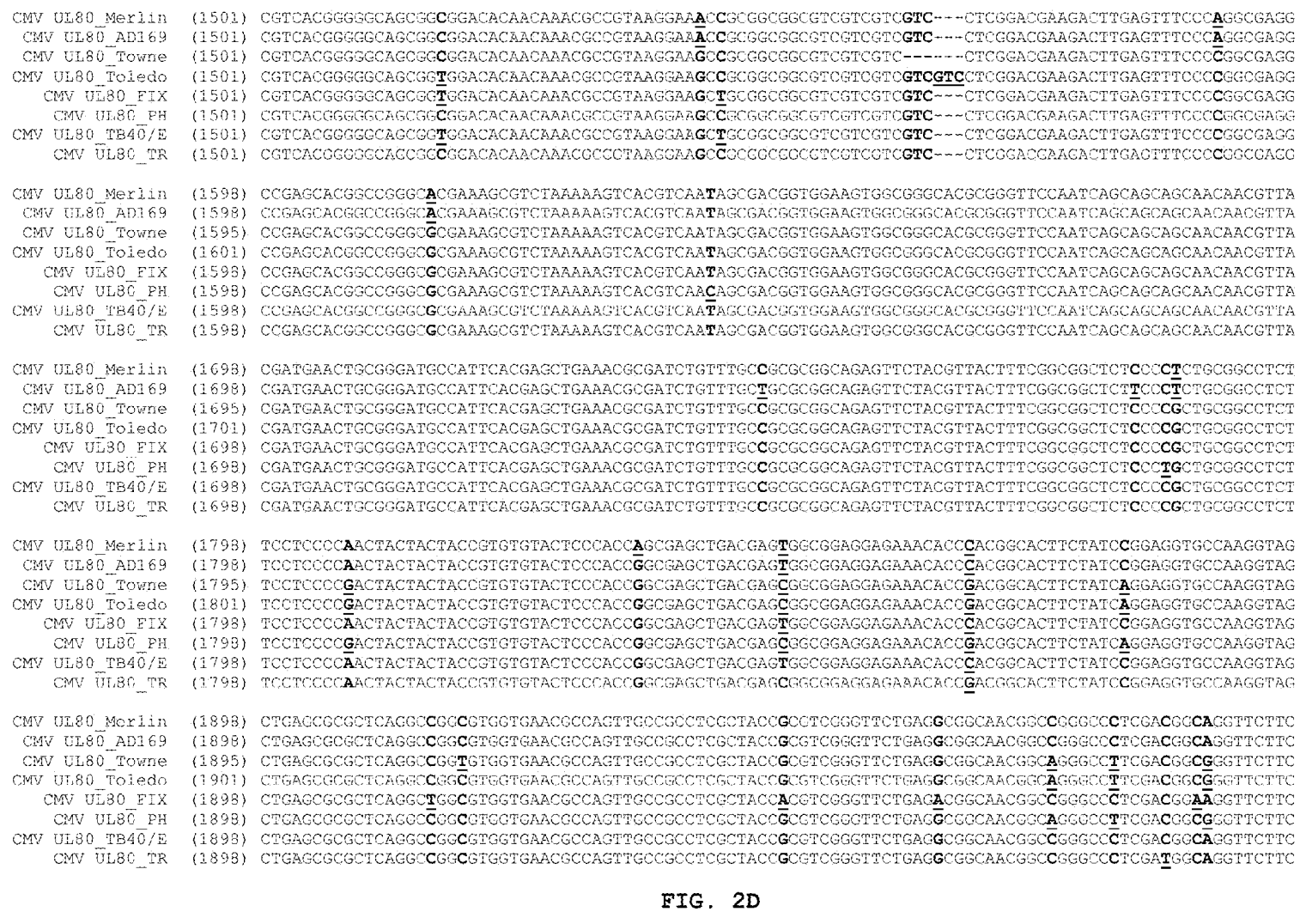
Figure 2E:
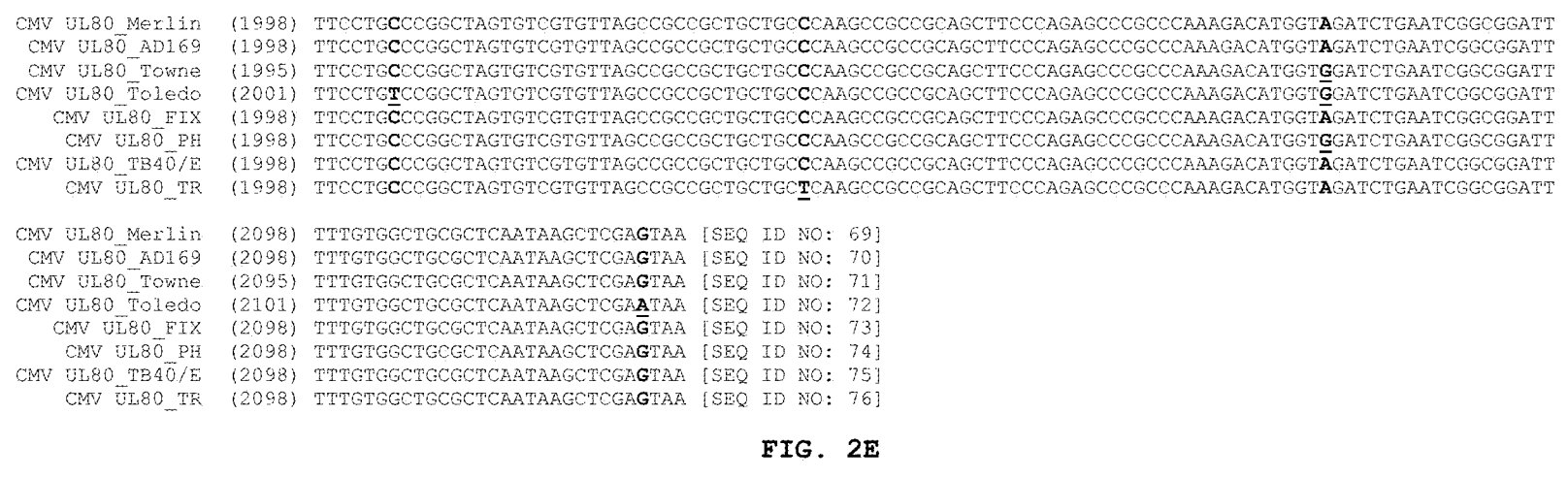

Publically available CMV sequences were aligned to maximize sequence homology. The alignments (see FIG. 1 (UL34) and FIG. 2 (UL80.5)) were used to identify potential regions for primers and probes that avoided mutation sites.

The following criteria were applied in selecting regions for primers and probes:
- no more than one mutation site within a primer or probe sequence,
- if a mutation is present, it must not be on or near the 3' end of the primer or probe,
- low or no self-priming likely,
- low chance of hairpin structure (for primers),
- no primer/primer or primer/probe annealing,
- relative Tm>65° C. in 6 mM MgCl$_2$,
- probe Tm should be about 5° C. higher than the primer Tm, if possible,
- strong G+C rich regions, palindromes, and stretches of more than four identical nucleotides in a row should be avoided, and
- a "G" at the 5' end of a probe should be avoided.

Example 2

This example describes the design and evaluation of primers and probes for amplification of UL34.

The primers and probes evaluated for amplification of UL34 are identified in Table I.

TABLE I

CMV UL34 Primers and Probes

| Location | Sequence | SEQ ID NO: |
|---|---|---|
| Forward Primers: | | |
| UL34 2-28 | 5' TGA ACT TCA TCA TCA CCA CCC GAG ACT 3' | 49 |
| UL34 5-31 | 5' ACT TCA TCA TCA CCA CCC GAG ACT TCT 3' | 56 |
| UL34 5-28 | 5' ACT TCA TCA TCA CCA CCC GAG ACT 3' | 1 |
| Reverse Primers: | | |
| UL34 78-103 | 5' TGT ACG CTT TGG AAA TCG AGC CTG CC 3' | 57 |
| UL34 75-101 | 5' CCT TGT ACG CTT TGG AAA TCG AGC CTG 3' | 50 |
| UL34 78-101 | 5' TGT ACG CTT TGG AAA TCG AGC CTG 3' | 2 |
| Probes: | | |
| UL34 40-65 | 5' ATT CAG TCC TGC GAG CCG CCG AGA T 3' | 3 |
| UL34 36-57 | 5' CG ACG ATT CAG TCC TGC GAG CC 3' | 51 |
| UL34 38-62 | 5' ACG ATT CAG TCC TGC GAG CCG A 3' | 58 |

Different combinations of primers and probe (Merlin strain of CMV; GenBank Accession No. AY446894.2) were evaluated under different concentrations of magnesium and different annealing temperatures. Then select combinations of primers and probes were evaluated for optimal amplification of low level CMV in whole blood specimens. CMV targets were spiked into eluates (i.e., the material recovered from sample preparation for purifying nucleic acid) from either negative diluent (Tris-buffered solution with low levels of carrier DNA) or human whole blood, which contains high levels of genomic DNA. Amplification plots were generated for head-to-head comparisons of four potential primer/probe sets for detecting UL34. The results of the testing showed that the following primer/probe sets performed equivalently and well:

[SEQ ID NO: 49]
forward primer (FP): 5' TGA ACT TCA TCA TCA CCA CCC GAG ACT 3',

[SEQ ID NO: 57]
reverse primer (RP): 5' TGT ACG CTT TGG AAA TCG AGC CTG CC 3',
and

[nucleotide sequence is SEQ ID NO: 3]
probe: 5' FAM-ATT CAG TCC TGC GAG CCG CCG AGA T-BHQ-1 dT 3';
and

[SEQ ID NO: 49]
forward primer (FP): 5' TGA ACT TCA TCA TCA CCA CCC GAG ACT 3',

-continued

```
                                              [SEQ ID NO: 50]
reverse primer (RP): 5' CCT TGT ACG CTT TGG AAA TCG AGC CTG 3',
and

[nucleotide sequence is SEQ ID NO: 3]
probe: 5' FAM-ATT CAG TCC TGC GAG CCG CCG AGA T-BHQ-1 dT 3'.
```

There was little to no difference in the amount of target amplified in both ND and WB samples with these primer/probe sets. The following primer/probe sets did not perform as well:

```
                                              [SEQ ID NO: 56]
forward primer (FP): 5' ACT TCA TCA TCA CCA CCC GAG ACT TCT 3',

[SEQ ID NO: 57]
reverse primer (RP): 5' TGT ACG CTT TGG AAA TCG AGC CTG CC 3',
and

[nucleotide sequence is SEQ ID NO: 3]
probe: 5' FAM-ATT CAG TCC TGC GAG CCG CCG AGA T-BHQ-1 dT 3';
and

[SEQ ID NO: 56]
forward primer (FP): 5' ACT TCA TCA TCA CCA CCC GAG ACT TCT 3',

[SEQ ID NO: 50]
reverse primer (RP): 5' CCT TGT ACG CTT TGG AAA TCG AGC CTG 3',
and

[nucleotide sequence is SEQ ID NO: 3]
probe: 5' FAM-ATT CAG TCC TGC GAG CCG CCG AGA T-BHQ-1 dT 3'.
```

The amplification of CMV in whole blood with these primer/probe sets was not as efficient and, therefore, not as robust as similar samples in negative diluent. Based on such evaluations, the following primer sequences and probe sequence were selected for amplification of UL34:

```
                                              [SEQ ID NO: 1]
forward primer (FP): 5' ACT TCA TCA TCA CCA CCC GAG ACT 3',

[SEQ ID NO: 2]
reverse primer (RP): 5' TGT ACG CTT TGG AAA TCG AGC CTG 3',
and

[nucleotide sequence is SEQ ID NO: 3]
probe: 5' QUASAR ™-ATT CAG TCC TGC GAG CCG CCG AGA T-BHQ-2 ™ dT 3'.
```

Example 3

This example describes the design and evaluation of primers and probes for amplification of UL80.5

The primers and probes evaluated for amplification of UL80.5 are identified in Table II.

TABLE II

CMV UL80.5 Primers and Probes

| Location | Sequence | SEQ ID NO: |
|---|---|---|
| Forward Primers: | | |
| UL80 1006-1025 Forward | 5' ATG TCG CAC CCT CTG AGT GC 3' | 4 |
| UL80 1012-1031 Forward | 5' CAC CCT CTG AGT GCT GCG GT 3' | 5 |
| UL80 1038-1056 Forward | 5' CGC TAC GGC TCC TCC AGG T 3' | 6 |
| UL80 1056-1075 Forward | 5' TGC TAC CGT GGC AGG TGC GT 3' | 7 |

TABLE II-continued

CMV UL80.5 Primers and Probes

| Location | Sequence | SEQ ID NO: |
|---|---|---|
| UL80 1154-1171 Forward | 5' CCA GTC GCT CGG CAG CGC 3' | 8 |
| UL80 1204-1223 Forward | 5' CCT TCT GCT TCG CCA GCA CC 3' | 9 |
| UL80 1226-1247 Forward | 5' TGC CTT TGC CGT CTT ATC CCG C 3' | 10 |
| UL80 1229-1247 Forward | 5' CTT TGC CGT CTT ATC CCG C 3' | 11 |
| UL80 1376-1395 Forward | 5' CCG TGC CGC CGC CAC CAT CA 3' | 12 |
| UL80 1379-1395 Forward | 5' TGC CGC CGC CAC CAT CA 3' | 13 |
| UL80 1642-1660 Forward | 5' AGC GAC GGT GGA AGT GGC G 3' | 14 |
| UL80 1666-1690 Forward | 5' GCG GGT TCC AAT CAG CAG CAG CAA C 3' | 15 |
| UL80 2006-2024 Forward | 5' CGG CTA GTG TCG TGT TAG C 3' | 16 |
| UL80 2043-2061 Forward | 5' CGC CGC AGC TTC CCA GAG C 3' | 17 |

Probes:

| Location | Sequence | SEQ ID NO: |
|---|---|---|
| UL80 1037-1058 Forward | 5' CCG CTA CGG CTC CTC CAG GTG C 3' | 18 |
| UL80 1037-1058 Reverse | 5' GCA CCT GGA GGA GCC GTA GCG G 3' | 19 |
| UL80 1059-1079 Forward | 5' TAC CGT GGC AGG TGC GTC GCC 3' | 20 |
| UL80 1056-1077 Reverse | 5' CGA CGC ACC TGC CAC GGT AGC A 3' | 21 |
| UL80 1101-1126 Forward | 5' GCC TCA CGA CGG AGT TTA TTT ACC CA 3' | 22 |
| UL80 1203-1223 Reverse | 5' GGT GCT GGC GAA GCA GAA GGA 3' | 23 |
| UL80 1263-1286 Forward | 5' CGT CGT GGG TTA CGA CCA GTT GGC 3' | 24 |
| UL80 1263-1285 Reverse | 5' GCC AAC TGG TCG TAA CCC ACG AC 3' | 25 |
| UL80 1399-1418 Forward | 5' GCC TAT TAC CGT CGG CGC GA 3' | 26 |
| UL80 1399-1418 Reverse | 5' TCG CGC CGA CGG TAA TAG GC 3' | 27 |
| UL80 1666-1690 Forward | 5' GCG GGT TCC AAT CAG CAG CAG CAA C 3' | 28 |
| UL80 1666-1690 Reverse | 5' GTT GCT GCT GCT GAT TGG AAC CCG C 3' | 29 |
| UL80 1698-1722 Forward | 5' CGA TGA ACT GCG GGA TGC CAT TCA C 3' | 30 |
| UL80 1698-1722 Reverse | 5' GTG AAT GGC ATC CCG CAG TTC ATC G 3' | 31 |
| UL80 2043-2061 Forward | 5' CGC CGC AGC TTC CCA GAG C 3' | 32 |
| UL80 2042-2060 Reverse | 5' GGC TCT GGG AAG CTG CGG C 3' | 33 |
| UL80 2080-2103 Reverse | 5' CAC AAA AAT CCG CCG ATT CAG ATC 3' | 34 |
| UL80 2039-2058 Reverse | 5' CTG GGA AGC TGC GGC GGC TT 3' | 59 |
| UL80 2041-2060 Reverse | 5' CTC TGG GAA GCT GCG GCG GC 3' | 60 |

Reverse Primers:

| Location | Sequence | SEQ ID NO: |
|---|---|---|
| UL80 1060-1078 Reverse | 5' CGG CGA CGC ACC TGC CAC G 3' | 35 |
| UL80 1068-1086 Reverse | 5' CAC AGC CGG CGA CGC ACC T 3' | 36 |
| UL80 1101-1124 Reverse | 5' GGT AAA TAA ACT CCG TCG TGA GGC 3' | 37 |
| UL80 1137-1157 Reverse | 5' CTG GCC CCA AGT AGC GAG AAA 3' | 38 |
| UL80 1154-1172 Reverse | 5' GGC GCT GCC GAG CGA CTG G 3' | 39 |

TABLE II-continued

CMV UL80.5 Primers and Probes

| Location | Sequence | SEQ ID NO: |
|---|---|---|
| UL80 1229-1247 Reverse | 5' GCG GGA TAA GAC GGC AAA G 3' | 40 |
| UL80 1291-1310 Reverse | 5' ACG TAG TCC GCA AAG TGA CG 3' | 41 |
| UL80 1421-1440 Reverse | 5' TTC ATC CAT ACC GCC CGG AG 3' | 42 |
| UL80 1700-1719 Reverse | 5' AAT GGC ATC CCG CAG TTC AT 3' | 43 |
| UL80 1750-1774 Reverse | 5' CCG AAA GTA ACG TAG AAC TCT GCC G 3' | 44 |
| UL80 1760-1781 Reverse | 5' AGA GCC GCC GAA AGT AAC GTA G 3' | 45 |
| UL80 2066-2090 Reverse | 5' CGA TTC AGA TCT ACC ATG TCT TTG G 3' | 46 |
| UL80 2080-2103 Reverse | 5' CAC AAA AAT CCG CCG ATT CAG ATC 3' | 47 |
| UL80 2106-2123 Reverse | 5' TCG AGC TTA TTG AGC GCA 3' | 48 |

The physical analysis of the primers and probes of Table II is shown in Table III.

TABLE III

CMV UL80.5 Primers and Probes

| Location | SEQ ID NO: | Length (nts) | % GC | °C. | Self-priming (kcal/mole) | Hairpin (kcal/mole) |
|---|---|---|---|---|---|---|
| Forward Primers: | | | | | | |
| UL80 1006-1025 Forward | 4 | 20 | 60 | 68.3 | −6.44 | −2.75 |
| UL80 1012-1031 Forward | 5 | 20 | 65 | 70.1 | −4.41 | −0.09 |
| UL80 1038-1056 Forward | 6 | 19 | 68.4 | 69.4 | −4.67 | −1.45 |
| UL80 1056-1075 Forward | 7 | 20 | 65 | 72.4 | −5.09 | −2.1 |
| UL80 1154-1171 Forward | 8 | 19 | 78.9 | 73.4 | −9.89 | −3.87 |
| UL80 1204-1223 Forward | 9 | 20 | 65 | 69.3 | −6.69 | −2.67 |
| UL80 1226-1247 Forward | 10 | 22 | 59.1 | 70.7 | −3.61 | −0.88 |
| UL80 1229-1247 Forward | 11 | 19 | 57.9 | 65 | −3.61 | 0.3 |
| UL80 1376-1395 Forward | 12 | 20 | 75 | 75.2 | −3.61 | −0.64 |
| UL80 1379-1395 Forward | 13 | 17 | 70.6 | 71.7 | −3.61 | −0.64 |
| UL80 1642-1660 Forward | 14 | 19 | 68.4 | 70.8 | −3.61 | −1.31 |
| UL80 1666-1690 Forward | 15 | 25 | 60 | 72.9 | −3.61 | −2.32 |
| UL80 2006-2024 Forward | 16 | 20 | 60 | 66.2 | −8.77 | −3.38 |
| UL80 2043-2061 Forward | 17 | 19 | 73.7 | 71.5 | −6.34 | −1.33 |
| Probes: | | | | | | |
| UL80 1037-1058 Forward | 18 | 22 | 72.7 | 73.3 | −6.68 | −2.55 |
| UL80 1037-1058 Reverse | 19 | 22 | 72.7 | 73.3 | −6.68 | −3.62 |
| UL80 1059-1079 Forward | 20 | 22 | 68.2 | 73.8 | −5.09 | −2.1 |
| UL80 1056-1077 Reverse | 21 | 22 | 68.2 | 73.8 | −5.09 | −1.77 |
| UL80 1101-1126 Forward | 22 | 26 | 50 | 69.5 | −3.61 | −1.05 |
| UL80 1203-1223 Reverse | 23 | 21 | 61.9 | 70.5 | −6.68 | −2.98 |
| UL80 1263-1286 Forward | 24 | 24 | 62.5 | 71.7 | −7.87 | −5.17 |
| UL80 1263-1285 Reverse | 25 | 24 | 62.5 | 71.7 | −7.87 | −5.03 |
| UL80 1399-1418 Forward | 26 | 20 | 65 | 70.1 | −10.36 | −1.35 |
| UL80 1399-1418 Reverse | 27 | 20 | 65 | 70.1 | −10.36 | −1.82 |
| UL80 1666-1690 Forward | 28 | 25 | 60 | 72.9 | −3.61 | −2.32 |
| UL80 1666-1690 Reverse | 29 | 25 | 60 | 72.9 | −3.61 | −2.48 |
| UL80 1698-1722 Forward | 30 | 25 | 56 | 70.7 | −5.47 | −2.96 |
| UL80 1698-1722 Reverse | 31 | 25 | 56 | 70.7 | −5.47 | −2.94 |
| UL80 2043-2061 Forward | 32 | 19 | 73.7 | 71.5 | −6.34 | −1.33 |
| UL80 2043-2061 Reverse | 33 | 19 | 73.7 | 71.5 | −6.34 | −1.19 |
| UL80 2080-2103 Reverse | 34 | 24 | 45.8 | 66.3 | −4.99 | −1.06 |
| Reverse Primers: | | | | | | |
| UL80 1060-1078 Reverse | 35 | 17 | 76.5 | 70.1 | −6.75 | −1.96 |
| UL80 1068-1086 Reverse | 36 | 19 | 73.7 | 73.2 | −16.03 | −2.02 |
| UL80 1101-1124 Reverse | 37 | 24 | 50 | 66.7 | −3.61 | −1.4 |
| UL80 1137-1157 Reverse | 38 | 21 | 57.1 | 68.1 | −9.28 | −1.03 |
| UL80 1154-1172 Reverse | 39 | 19 | 78.9 | 73.4 | −9.89 | −5.02 |
| UL80 1229-1247 Reverse | 40 | 19 | 57.9 | 65 | −3.61 | −0.71 |
| UL80 1291-1310 Reverse | 41 | 20 | 55 | 66.4 | −6.3 | −1.23 |

TABLE III-continued

CMV UL80.5 Primers and Probes

| Location | SEQ ID NO: | Length (nts) | % GC | °C. | Self-priming (kcal/mole) | Hair-pin (kcal/mole) |
|---|---|---|---|---|---|---|
| UL80 1421-1440 Reverse | 42 | 20 | 60 | 67.7 | −9.75 | −1.85 |
| UL80 1700-1719 Reverse | 43 | 20 | 50 | 67 | −3.61 | −1.68 |
| UL80 1750-1774 Reverse | 44 | 25 | 52 | 68 | −6.3 | −0.53 |
| UL80 1760-1781 Reverse | 45 | 22 | 54.5 | 67.8 | −6.3 | −0.5 |
| UL80 2066-2090 Reverse | 46 | 25 | 44 | 64.9 | −7.82 | −2.17 |
| UL80 2080-2103 Reverse | 47 | 24 | 45.8 | 66.3 | −4.99 | −1.06 |
| UL80 2106-2123 Reverse | 48 | 18 | 50 | 63.8 | −9.89 | −2.08 |
| Mean | | 21.27 | 62.36 | 69.99 | −6.32 | −1.96 |
| S.D. | | 2.51 | 9.28 | 2.90 | 2.63 | 1.25 |

The combinations of forward primer, reverse primer and probe that were evaluated for amplification of UL80.5 are shown in Table IV.

TABLE IV

UL80.5 Combinations of Primers and Probe

| Combo | Forward Primer | Probe (R = reverse; F = forward) | Reverse Primer | Amplicon (nts) |
|---|---|---|---|---|
| 1 | UL80 1006-1025 | UL80 1037-1058 R | UL80 1060-1078 | 73 |
| 2 | UL80 1006-1025 | UL80 1037-1058 F | UL80 1068-1086 | 81 |
| 3 | UL80 1006-1025 | UL80 1037-1058 R | UL80 1068-1086 | 81 |
| 4 | UL80 1006-1025 | UL80 1037-1058 F | UL80 1101-1124 | 119 |
| 5 | UL80 1006-1025 | UL80 1037-1058 R | UL80 1101-1124 | 119 |
| 6 | UL80 1006-1025 | UL80 1059-1079 F | UL80 1101-1124 | 119 |
| 7 | UL80 1006-1025 | UL80 1056-1077 R | UL80 1101-1124 | 119 |
| 8 | UL80 1012-1031 | UL80 1037-1058 F | UL80 1060-1078 | 67 |
| 9 | UL80 1012-1031 | UL80 1037-1058 R | UL80 1060-1078 | 67 |
| 10 | UL80 1012-1031 | UL80 1037-1058 F | UL80 1068-1086 | 75 |
| 11 | UL80 1012-1031 | UL80 1037-1058 R | UL80 1068-1086 | 75 |
| 12 | UL80 1012-1031 | UL80 1037-1058 F | UL80 1101-1124 | 113 |
| 13 | UL80 1012-1031 | UL80 1037-1058 R | UL80 1101-1124 | 113 |
| 14 | UL80 1012-1031 | UL80 1059-1079 F | UL80 1101-1124 | 113 |
| 15 | UL80 1012-1031 | UL80 1056-1077 R | UL80 1101-1124 | 113 |
| 16 | UL80 1038-1056 | UL80 1101-1126 F | UL80 1137-1157 | 120 |
| 17 | UL80 1056-1075 | UL80 1101-1126 F | UL80 1137-1157 | 102 |
| 18 | UL80 1056-1075 | UL80 1101-1126 F | UL80 1154-1172 | 117 |
| 19 | UL80 1154-1171 | UL80 1203-1223 R | UL80 1229-1247 | 94 |
| 20 | UL80 1204-1223 | UL80 1263-1285 R | UL80 1291-1310 | 107 |
| 21 | UL80 1226-1247 | UL80 1263-1286 F | UL80 1291-1310 | 85 |
| 22 | UL80 1226-1247 | UL80 1263-1285 R | UL80 1291-1310 | 85 |
| 23 | UL80 1229-1247 | UL80 1263-1286 F | UL80 1291-1310 | 82 |
| 24 | UL80 1229-1247 | UL80 1263-1285 R | UL80 1291-1310 | 82 |
| 25 | UL80 1376-1395 | UL80 1399-1418 F | UL80 1421-1440 | 65 |
| 26 | UL80 1376-1395 | UL80 1399-1418 R | UL80 1421-1440 | 65 |
| 27 | UL80 1379-1395 | UL80 1399-1418 F | UL80 1421-1440 | 62 |
| 28 | UL80 1379-1395 | UL80 1399-1418 R | UL80 1421-1440 | 62 |
| 29 | UL80 1642-1660 | UL80 1666-1690 F | UL80 1700-1719 | 78 |
| 30 | UL80 1642-1660 | UL80 1666-1690 R | UL80 1700-1719 | 78 |
| 31 | UL80 1666-1690 | UL80 1698-1722 F | UL80 1750-1774 | 109 |
| 32 | UL80 1666-1690 | UL80 1698-1722 R | UL80 1750-1774 | 109 |
| 33 | UL80 1666-1690 | UL80 1698-1722 F | UL80 1760-1781 | 116 |
| 34 | UL80 1666-1690 | UL80 1698-1722 R | UL80 1760-1781 | 116 |
| 35 | UL80 2006-2024 | UL80 2043-2061 F | UL80 2066-2090 | 85 |
| 36 | UL80 2006-2024 | UL80 2042-2060 R | UL80 2066-2090 | 85 |
| 37 | UL80 2006-2024 | UL80 2043-2061 F | UL80 2080-2103 | 98 |
| 38 | UL80 2006-2024 | UL80 2042-2060 R | UL80 2080-2103 | 98 |
| 39 | UL80 2006-2024 | UL80 2080-2103 R | UL80 2106-2123 | 118 |
| 40 | UL80 2043-2061 | UL80 2080-2103 R | UL80 2106-2123 | 81 |

The various combinations of primers and probe for UL80.5 were evaluated in quadruplicates at different concentrations of magnesium and different annealing temperatures. Each reaction contained 0.5 μM CMV forward primer, 0.5 μM CMV reverse primer, 0.2 μM CMV probe, 0.5 μM internal control (IC) forward primer, 0.5 μM IC reverse primer, 0.2 μM IC PCR probe, 0.012 μM ROX (a passive reference dye with constant fluorescence that provides a stable baseline for sample normalization; Life Technologies Corp., Carlsbad, Calif.), 1 unit of 10× Taq Gold Buffer, 0.6 mM dNTPs, 7.5 Units/reaction Amplitaq Gold, 84 copies/reaction CTNG IC 2G28Y (Abbott Laboratories, Abbott Park, Ill.), 5 μg genomic DNA, and $1.5 \times 10^3$ copies/reaction CMV target. The final reaction volume was brought to 60 μL using molecular biology water. Concentrations of magnesium included 4 mM, 6 mM, 8 mM, 10 mM, 12 mM and 14 mM. The annealing temperatures included 62° C. and 58° C. The fluorescent dye Cy5 was used to detect amplification of the target region, whereas the fluorescent dye NED (Life Technologies Corp., Carlsbad, Calif.) was used to detect amplification of the IC. The maxRatio (MR) analysis (Abbott Molecular, Inc., Des Plaines, Ill.) was employed, and the mean MR and quantitative cycle numbers (FCN) were determined.

Example 4

This example describes the evaluation of UL34 primers and probes in combination with UL80.5 primers and probes and the optimization of amplification conditions for detection of low levels of CMV in plasma and whole blood samples UL80.5 primers and probe combination 38 was selected for evaluation with the UL34 primers and probe in the analysis of CMV-spiked plasma and whole blood samples in triplicate. A 3× reagent master mix containing 500 nM CMV UL34 forward primer, 500 nM CMV UL34 reverse primer, 200 nM CMV UL34 FAM™ (FAM™, Applied Biosystems, Foster, Calif.) probe, 500 nM CMV UL80 forward primer, 500 nM CMV UL80 reverse primer, 200 nM CMV UL80 Cy5 probe, 500 nM IC forward primer, 500 nM IC reverse primer, 200 nM IC CT/NG probe (Abbott Laboratories, Abbott Park, Ill.), 12 nM ROX, 1 unit of 10× Taq Gold Buffer, 600 μM dNTPs, 6 mM $MgCl_2$, and 7.5 Units/μL Amplitaq Gold was prepared. The reagent master mix was prepared as 3× and was brought to a final volume of 4.1 mL using molecular biology water. Twenty microliters of the 3× reagent master mix were used per reaction in a total volume of 60 μL. Samples were evaluated using the Abbott m2000rt amplification detection system (Abbott Molecular, Inc.) with cycling conditions of one cycle at 95° C. for 9.5 minutes and 45 cycles at 92° C. for 10 seconds, 62° C. for 30 seconds, and 65° C. for one minute.

Cycling conditions were optimized to address the fact that CMV is G-C rich (~57%). The combination of one cycle at 95° C. for 9.5 minutes, five cycles at 92° C. for five seconds, 96° C. for 10 seconds, 66° C. for five seconds, 62° C. for 30 seconds, and 65° C. for seconds, and 42 cycles at 85° C. for 5 seconds, 92° C. for 10 seconds, 66° C. for 5 seconds, 62° C. for 30 seconds, and 65° C. for 60 seconds was determined to be optimal.

Conditions were also optimized to eradicate non-specific amplifications that can result in false positive results. Tests were conducting using water as the target. Primers and probes were prepared in the PCR reaction master mix. The results are shown in Table V.

TABLE V

Results from Experiments Testing for Non-Specific CMV (FAM) Amplification Detection

| Run | Seq ID Nos. Tested (FP - Probe - RP) | Result |
|---|---|---|
| 1 | [UL34] 1-51-50/[UL80] 16-60-47 | 1/184 reactive |
|   | [UL34] 1-51-50/[UL80] 16-59-47 | 2/184 reactive |
| 2 | [UL34] 1-51-50/[UL80] 16-60-48 | 1/184 reactive |
| 3 | [UL34] 49-51-50 | 0/280 reactive |
| 4 | [UL34] 49-51-50/[UL80] 16-60-47 | 27/184 reactive |
|   | [UL34] 49-51-50/[UL80] 16-60-48 | 25/184 reactive |
|   | [UL34] 49-51-50/[UL80] 16-59-48 | 17/184 reactive |
| 5 | [UL34] 1-51-50/[UL80] 16-60-47 | 3/24 reactive |
|   | [UL34] 49-51-2/[UL80] 16-60-47 | 6/24 reactive |
| 6 | [UL34] 1-51-57/[UL80] 16-60-47 | 4/24 reactive |
|   | [UL34] 49-51-2/[UL80] 16-60-47 | 1/24 reactive |
|   | [UL34] 49-51-50/[UL80] 16-60-47 | 0/24 reactive |
|   | [UL80] 16-60-47 | 13/208 reactive |
|   | [UL34] 49-51-50 | 0/96 reactive |
| 7 | [UL80] 16-33-47 | 0/32 reactive |
|   | [UL80] 16-52-47 | 0/32 reactive |
|   | [UL80] 16-59-47 | 0/32 reactive |
|   | [UL80] 16-33-48 | 1/32 reactive |
|   | [UL80] 16-52-48 | 0/32 reactive |
|   | [UL80] 16-59-48 | 0/32 reactive |
| 8 | [UL34] 49-51-57/[UL80] 16-52-47 | 0/96 reactive |
|   | [UL34] 49-51-50/[UL80] 16-52-47 | 0/96 reactive |
| 9 | [UL34] 49-51-50/[UL80] 16-52-47/[IC] 53-55-54 | 1/768 reactive |

Conditions were also optimized for whole blood samples. The detection of very low levels of CMV is difficult in whole blood due to the presence of large quantities of human genomic DNA and the competition of non-specific binding of primers and probe. The following changes were made to the UL34 primers and probe in order to optimize conditions for whole blood samples (additions shown in bold, deletions shown by strikethrough):

[SEQ ID NO: 49]
forward primer (FP): 5' TGA ACT TCA TCA TCA CCA CCC GAG ACT 3',

[SEQ ID NO: 50]
reverse primer (RP): 5' CCT TGT ACG CTT TGG AAA TCG AGC CTG 3', and

[nucleotide sequence is SEQ ID NO: 51]
probe: 5' Quasar-CG ACG ATT CAG TCC TGC GAG CCG CC-BHQ2 dT 3'.

With regard to the forward primer, it is interesting to note that the addition of TCT to the 3' end, instead of the addition of TGA to the 5' end, decreased performance. With regard to the reverse primer, the addition of CC to the 3' end was comparable to the addition of CCT to the 5' end. With regard to the probe, addition of CGACG to the 5' end and deletion of GCCGAGAT from the 3' end of the probe improved performance. The following change was made to the UL80.5 probe in combination no. 38 in order to optimize conditions for whole blood samples:

[SEQ ID NO: 33]
forward probe: 5' GGC TCT GGG AAG CTG CGG C 3'

[SEQ ID NO: 52]
was replaced with reverse probe: 5' AAGCCGCCGCAGCTTCCCAG 3'.

The forward primer, reverse primer, and probe selected for amplification of the IC (hydroxypyruvate reductase gene from *Cucurbita pepo*) are as follows:

```
                                            [SEQ ID NO: 53]
forward primer (FP): 5' CLL CAC LLL CLC LLG CAG 3',
wherein L = 5-propynyl dU

[SEQ ID NO: 54]
reverse primer (RP): 5' ACA AAT TTG GAA GCC ATG CAT CA 3',
and

[nucleotide sequence is SEQ ID NO: 55]
probe: 5' NED-AA GCT GAC GAG TTC ATG AGG GCA GG-BHQ2-dT 3'.
```

The following primer and probe concentrations were selected for PCR (Table VI):

TABLE VI

| | |
|---|---|
| UL34 FP | 0.5 µM |
| UL34 RP | 0.5 µM |
| UL34 probe | 100 nM |
| UL80.5 FP | 0.5 µM |
| UL80.5 RP | 0.5 µM |
| UL80.5 probe | 150 nM |
| IC FP | 0.5 µM |
| IC RP | 0.5 µM |
| IC probe | 150 nM |
| dNTPs | 0.8 mM |
| ROX | 120 nM |
| MgCl$_2$ | 6 mM |
| AmpliTaq Gold | 11.25 units/reaction |

Assay level of detection (LOD) analysis of plasma samples spiked with CMV indicated that 100% of samples containing 14 copies/mL (or 1.13 log copies/mL; 95% confidence interval of 11-19 copies/mL or 1.04-1.29 log copies/mL) or more of inactivated CMV were detected with 95% probability. Assay LOD analysis of whole blood samples spiked with CMV indicated that 100% of samples containing 27 copies/mL (95% confidence interval of 24-31 copies/mL) or more of inactivated CMV were detected with 95% probability. The different in assay LOD between plasma samples and whole blood samples reflects the difference in sample input volume for sample preparation. The limit of detection is defined as the CMV DNA concentration detected with a probability of 95% or greater. When the assay performance is standardized to the 1$^{st}$ International WHO Standard for Human Cytomegalovirus, the values in IU/mL are:

Plasma 21.08 IU/mL (95% CI 17.01 to 30.10 IU/mL) and Whole Blood 41.99 IU/mL (95% CI 37.61 to 48.72 IU/mL).

Example 5

This example demonstrates that the assay detects expected amounts of CMV DNA.

The ZeptoMetrix OptiQuant$_{CMV}$ Panel DNA (ZeptoMetrix Corp., Buffalo, N.Y.) is a panel of varying concentrations of CMV intact virions for extraction and assay of DNA. The panel is routinely used in the art to assess performance of a given CMV assay. The expected amount of panel DNA purified from whole virions was detected using the Abbott Real-Time CMV Assay (n=6 replicates for each panel level). The nominal panel member CMV target levels are 2.7, 3.7, 4.7 and 5.7 log copies/mL for CMV$_{tc}$ 5E2, 5E3, 5E4 and 5E5 panel members, respectively. The results of the testing (mean Log copies/mL for 6 replicates) with the Abbott RealTime CMV Assay using the primers and probes described in the above example were 2.48, 3.37, 4.35 and 5.42 log copies/ml for CMV$_{tc}$ 5E2, 5E3, 5E4 and 5E5 panel members, respectively.

Example 6

This example demonstrates that the assay does not generate false positive results for CMV in the presence of potential cross-reactants, and that there was no interference in the assay performance in the presence of the potential cross-reactants for CMV-positive samples.

Potential cross-reactants (e.g., Herpes simplex virus (HSV)-1 (purified nucleic acid), HSV-2 (purified nucleic acid), Epstein-Barr virus (EBV; purified nucleic acid), human herpes virus (HHV)-6A (purified nucleic acid), HHV-6B (purified nucleic acid), HHV-7 (purified nucleic acid), Kaposi's sarcoma-associated herpesvirus (KSHV)/HHV-8 (purified nucleic acid), Vaccinia virus (VACV; purified nucleic acid), Varicella Zoster virus (VZV; purified nucleic acid), BK human polyomavirus (purified nucleic acid), *Chlamydia trachomatis* (purified nucleic acid), *Neisseria gonorrhoeae* (purified nucleic acid), *Candida albicans* (purified nucleic acid), *Staphylococcus aureus* (purified nucleic acid), *Staphylococcus epidermidis* (purified nucleic acid), *Mycobacterium gordonae* (purified nucleic acid), *Mycobacterium smegmatis* (purified nucleic acid), human immunodeficiency virus (HIV)-1 (purified nucleic acid), HIV-2 (viral lysate), HTLV-1 (viral lysates), human papilloma virus (HPV)-16 (purified nucleic acid), HPV-18 (purified nucleic acid), hepatitis B virus (HBV; purified nucleic acid), and hepatitis C virus (HCV; purified nucleic acid) in CMV plasma samples were tested for cross-reactivity. Purified nucleic acid or viral lysate from each virus or microorganism was added to CMV Negative Control and plasma or whole blood samples that contained approximately 3,120 IU/mL CMV DNA. All potential cross-reactors were tested at a target concentration of $1\times10^5$ cp/mL. No interference in the performance of the assay was observed in the presence of the potential cross-reactants for all positive and negative samples tested.

Example 7

This example describes a comparison of the assay with the Artus CMV test in the analysis of clinical specimens for clinical correlation.

Whole blood clinical specimens (n=114) from St. Louis Hospital (Paris, France) were tested and produced positive results. The results were compared to the values determined by the hospital laboratory using the Artus CMV test, showing that 86% of clinical specimens were within 0.5 log of the reported values of both assays, with the mean difference between assays close to 0 (mean difference of assay−Artus=−0.08). St. Louis Hospital also provided paired clinical specimens in plasma that were not previously tested. Comparison of CMV testing of whole blood clinical specimens to their plasma equivalent specimen (as described herein) showed 82% of clinical specimens within 0.5 log of the reported values of both sample types, with the mean difference between specimen types close to 0 (mean difference assay of plasma−assay of whole blood=−0.11).

Example 8

This example describes the linearity of the assay.
Using the assay components described in Table VI, linearity was determined to range from 31.20 IU/mL to 156 million IU/mL for plasma samples spiked with CMV DNA, and from 62.40 IU/mL to 156 million IU/mL for whole blood samples spiked with CMV DNA.

Example 9

This example describes the precision of the assay.
Precision panels were made with either CMV plasmid (high target levels at greater than 1.56 million IU/mL) or inactivated CMV virus (mid to low target levels of 1.56 million IU/mL or lower) spiked in pooled human plasma and also in human whole blood. Testing was performed with three lots of amplification reagents on three instrument sets for each set of panels. The assay was designed to achieve an inter-assay standard deviation (SD) of less than or equal to 0.500 log IU/mL for plasma samples containing 780 to 15.6 million IU/mL of CMV DNA and for whole blood samples containing 1,560 to 15.6 million IU/mL of CMV DNA.

TABLE VII

Precision for Plasma Specimens

| Panel Member | n | Mean Conc. (IU/mL) | Mean Conc. (Log IU/mL) | Within-Run Component SD(Log IU/mL) | Between-Run Component SD(Log IU/mL) | Inter-Assay SD[a] (Log IU/mL) |
|---|---|---|---|---|---|---|
| 1 | 40[b] | 19 | 1.23 | 0.232 | 0.055 | 0.239 |
| 2 | 53[c] | 32 | 1.41 | 0.269 | 0.173 | 0.320 |
| 3 | 60 | 103 | 1.99 | 0.134 | 0.020 | 0.136 |
| 4 | 60 | 848 | 2.92 | 0.058 | 0.067 | 0.088 |
| 5 | 60 | 6,835 | 3.83 | 0.053 | 0.035 | 0.063 |
| 6 | 60 | 69,405 | 4.83 | 0.046 | 0.042 | 0.062 |
| 7 | 60 | 1,173,359 | 6.07 | 0.036 | 0.017 | 0.039 |
| 8 | 60 | 12,075,054 | 7.08 | 0.050 | 0.028 | 0.057 |
| 9 | 59[d] | 59,407,767 | 7.77 | 0.036 | 0.026 | 0.044 |
| 10 | 59[d] | 187,017,056 | 8.26 | 0.042 | 0.020 | 0.047 |

[a]Inter-assay SD contains the within-run and between-run components.
[b]CMV DNA was not detected in 20 replicates.
[c]CMV DNA was not detected in 6 replicates. One replicate of panel member 2 was determined to be an outlier and was, therefore, removed from the data analysis.
[d]One replicate did not generate a result due to instrument error.

TABLE VIII

Precision for Whole Blood Specimens

| Panel Member | n | Mean Conc. (IU/mL) | Mean Conc. (Log IU/mL) | Within-Run Component SD(Log IU/mL) | Between-Run Component SD(Log IU/mL) | Inter-Assay SD[a] (Log IU/mL) |
|---|---|---|---|---|---|---|
| 1 | 54[b] | 55 | 1.68 | 0.235 | 0.045 | 0.239 |
| 2 | 59[c] | 99 | 1.93 | 0.233 | 0.082 | 0.247 |
| 3 | 60 | 185 | 2.24 | 0.153 | 0.000 | 0.153 |
| 4 | 60 | 1,492 | 3.17 | 0.063 | 0.012 | 0.064 |
| 5 | 60 | 13,305 | 4.12 | 0.036 | 0.000 | 0.036 |
| 6 | 60 | 129,498 | 5.11 | 0.050 | 0.000 | 0.050 |
| 7 | 60 | 1,298,102 | 6.11 | 0.030 | 0.012 | 0.032 |
| 8 | 60 | 13,305,411 | 7.12 | 0.074 | 0.027 | 0.079 |
| 9 | 60 | 65,277,486 | 7.81 | 0.060 | 0.000 | 0.060 |
| 10 | 60 | 201,514,426 | 8.30 | 0.031 | 0.019 | 0.036 |

[a]Inter-assay SD contains the within-run and between-run components.
[b]CMV DNA was not detected in 6 replicates.
[c]CMV DNA was not detected in 1 replicate.

The results presented above are representative of the precision seen using the CMV primer and probe sets to detect CMV DNA purified from plasma and whole blood samples, respectively.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A method of amplifying and detecting cytomegalovirus (CMV) nucleic acid sequences in a sample, which method comprises:
   (a) forming a mixture comprising
      (i) the sample,
      (ii) nucleic acid amplification reagents,
      (iii) a first pair of primers for amplification of a unique long 34 (UL34) nucleic acid sequence, the first pair of primers consisting of 5' TGA ACT TCA TCA TCA CCA CCC GAG ACT 3' [SEQ ID NO: 49] as a forward primer and 5' CCT TGT ACG CTT TGG AAA TCG AGC CTG 3' [SEQ ID NO: 50] as a reverse primer,
      (iv) a second pair of primers for amplification of a unique long 80.5 (UL80.5) nucleic acid sequence, the second pair of primers consisting of 5' CGG CTA GTG TCG TGT TAG C 3' [SEQ ID NO: 16] as a forward primer and 5' CAC AAA AAT CCG CCG ATT CAG ATC 3' [SEQ ID NO: 47] as a reverse primer,
      (v) a first probe for detection of amplification of the UL34 nucleic acid sequence, the first probe consisting of 5' CG ACG ATT CAG TCC TGC GAG CC 3' [SEQ ID NO: 51], and
      (vi) a second probe for detection of amplification of the UL80.5 nucleic acid sequence, the second probe consisting of 5' AAG CCG CCG CAG CTT CCC AG 3' [SEQ ID NO: 52];
   (b) subjecting the mixture to conditions that promote amplification of the UL34 nucleic acid sequence and the UL80.5 nucleic acid sequence; and
   (c) simultaneously or subsequently detecting the presence, amount or concentration of CMV in the sample,
   wherein linearity ranges from 31.20 IU/mL to 156 million IU/mL for plasma and from 62.40 IU/mL to 156 million IU/mL for whole blood,
   whereupon CMV nucleic acid sequences in the sample are amplified and detected.

2. The method of claim 1, wherein the mixture in (a) further comprises an internal control (IC) nucleic acid and a pair of primers for amplifying the IC nucleic acid and wherein the conditions in (b) also promote amplification of the IC nucleic acid, whereupon the IC nucleic acid sequence is amplified.

3. The method of claim 1, wherein each of the first and second probes is detectably labeled.

4. The method of claim 2, which further comprises simultaneously or subsequently detecting the presence, amount or concentration of IC in the mixture, whereupon IC is detected in the mixture.

5. The method of claim 1, wherein each of the first and second probes is labeled with a fluorophore and a quencher.

6. The method of claim 5, wherein the fluorophore is FAM and the quencher is BHQ-1.

* * * * *

```
                         SEQUENCE LISTING

<160> NUMBER OF SEQ ID NOS: 76

<210> SEQ ID NO 1
<211> LENGTH: 24
<212> TYPE: DNA
<213> ORGANISM: Human cytomegalovirus

<400> SEQUENCE: 1
acttcatcat caccacccga gact                                            24

<210> SEQ ID NO 2
<211> LENGTH: 24
<212> TYPE: DNA
<213> ORGANISM: Human cytomegalovirus

<400> SEQUENCE: 2
tgtacgcttt ggaaatcgag cctg                                            24

<210> SEQ ID NO 3
<211> LENGTH: 25
<212> TYPE: DNA
<213> ORGANISM: Human cytomegalovirus

<400> SEQUENCE: 3
attcagtcct gcgagccgcc gagat                                           25

<210> SEQ ID NO 4
<211> LENGTH: 20
<212> TYPE: DNA
<213> ORGANISM: Human cytomegalovirus

<400> SEQUENCE: 4
atgtcgcacc ctctgagtgc                                                 20

<210> SEQ ID NO 5
<211> LENGTH: 20
<212> TYPE: DNA
<213> ORGANISM: Human cytomegalovirus
```

```
<400> SEQUENCE: 5
caccctctga gtgctgcggt                                              20

<210> SEQ ID NO 6
<211> LENGTH: 19
<212> TYPE: DNA
<213> ORGANISM: Human cytomegalovirus

<400> SEQUENCE: 6
cgctacggct cctccaggt                                               19

<210> SEQ ID NO 7
<211> LENGTH: 20
<212> TYPE: DNA
<213> ORGANISM: Human cytomegalovirus

<400> SEQUENCE: 7
tgctaccgtg gcaggtgcgt                                              20

<210> SEQ ID NO 8
<211> LENGTH: 18
<212> TYPE: DNA
<213> ORGANISM: Human cytomegalovirus

<400> SEQUENCE: 8
ccagtcgctc ggcagcgc                                                18

<210> SEQ ID NO 9
<211> LENGTH: 20
<212> TYPE: DNA
<213> ORGANISM: Human cytomegalovirus

<400> SEQUENCE: 9
ccttctgctt cgccagcacc                                              20

<210> SEQ ID NO 10
<211> LENGTH: 22
<212> TYPE: DNA
<213> ORGANISM: Human cytomegalovirus

<400> SEQUENCE: 10
tgcctttgcc gtcttatccc gc                                           22

<210> SEQ ID NO 11
<211> LENGTH: 19
<212> TYPE: DNA
<213> ORGANISM: Human cytomegalovirus

<400> SEQUENCE: 11
ctttgccgtc ttatcccgc                                               19

<210> SEQ ID NO 12
<211> LENGTH: 20
<212> TYPE: DNA
<213> ORGANISM: Human cytomegalovirus

<400> SEQUENCE: 12
ccgtgccgcc gccaccatca                                              20

<210> SEQ ID NO 13
<211> LENGTH: 17
<212> TYPE: DNA
<213> ORGANISM: Human cytomegalovirus
```

-continued

```
<400> SEQUENCE: 13
tgccgccgcc accatca                                                 17

<210> SEQ ID NO 14
<211> LENGTH: 19
<212> TYPE: DNA
<213> ORGANISM: Human cytomegalovirus

<400> SEQUENCE: 14
agcgacggtg gaagtggcg                                               19

<210> SEQ ID NO 15
<211> LENGTH: 25
<212> TYPE: DNA
<213> ORGANISM: Human cytomegalovirus

<400> SEQUENCE: 15
gcgggttcca atcagcagca gcaac                                        25

<210> SEQ ID NO 16
<211> LENGTH: 19
<212> TYPE: DNA
<213> ORGANISM: Human cytomegalovirus

<400> SEQUENCE: 16
cggctagtgt cgtgttagc                                               19

<210> SEQ ID NO 17
<211> LENGTH: 19
<212> TYPE: DNA
<213> ORGANISM: Human cytomegalovirus

<400> SEQUENCE: 17
cgccgcagct tcccagagc                                               19

<210> SEQ ID NO 18
<211> LENGTH: 22
<212> TYPE: DNA
<213> ORGANISM: Human cytomegalovirus

<400> SEQUENCE: 18
ccgctacggc tcctccaggt gc                                           22

<210> SEQ ID NO 19
<211> LENGTH: 22
<212> TYPE: DNA
<213> ORGANISM: Human cytomegalovirus

<400> SEQUENCE: 19
gcacctggag gagccgtagc gg                                           22

<210> SEQ ID NO 20
<211> LENGTH: 21
<212> TYPE: DNA
<213> ORGANISM: Human cytomegalovirus

<400> SEQUENCE: 20
taccgtggca ggtgcgtcgc c                                            21

<210> SEQ ID NO 21
<211> LENGTH: 22
<212> TYPE: DNA
```

<213> ORGANISM: Human cytomegalovirus

<400> SEQUENCE: 21
cgacgcacct gccacggtag ca                                    22

<210> SEQ ID NO 22
<211> LENGTH: 26
<212> TYPE: DNA
<213> ORGANISM: Human cytomegalovirus

<400> SEQUENCE: 22
gcctcacgac ggagtttatt taccca                                26

<210> SEQ ID NO 23
<211> LENGTH: 21
<212> TYPE: DNA
<213> ORGANISM: Human cytomegalovirus

<400> SEQUENCE: 23
ggtgctggcg aagcagaagg a                                     21

<210> SEQ ID NO 24
<211> LENGTH: 24
<212> TYPE: DNA
<213> ORGANISM: Human cytomegalovirus

<400> SEQUENCE: 24
cgtcgtgggt tacgaccagt tggc                                  24

<210> SEQ ID NO 25
<211> LENGTH: 23
<212> TYPE: DNA
<213> ORGANISM: Human cytomegalovirus

<400> SEQUENCE: 25
gccaactggt cgtaacccac gac                                   23

<210> SEQ ID NO 26
<211> LENGTH: 20
<212> TYPE: DNA
<213> ORGANISM: Human cytomegalovirus

<400> SEQUENCE: 26
gcctattacc gtcggcgcga                                       20

<210> SEQ ID NO 27
<211> LENGTH: 20
<212> TYPE: DNA
<213> ORGANISM: Human cytomegalovirus

<400> SEQUENCE: 27
tcgcgccgac ggtaataggc                                       20

<210> SEQ ID NO 28
<211> LENGTH: 25
<212> TYPE: DNA
<213> ORGANISM: Human cytomegalovirus

<400> SEQUENCE: 28
gcgggttcca atcagcagca gcaac                                 25

<210> SEQ ID NO 29
<211> LENGTH: 25

```
<212> TYPE: DNA
<213> ORGANISM: Human cytomegalovirus

<400> SEQUENCE: 29
gttgctgctg ctgattggaa cccgc                                    25

<210> SEQ ID NO 30
<211> LENGTH: 25
<212> TYPE: DNA
<213> ORGANISM: Human cytomegalovirus

<400> SEQUENCE: 30
cgatgaactg cgggatgcca ttcac                                    25

<210> SEQ ID NO 31
<211> LENGTH: 25
<212> TYPE: DNA
<213> ORGANISM: Human cytomegalovirus

<400> SEQUENCE: 31
gtgaatggca tcccgcagtt catcg                                    25

<210> SEQ ID NO 32
<211> LENGTH: 19
<212> TYPE: DNA
<213> ORGANISM: Human cytomegalovirus

<400> SEQUENCE: 32
cgccgcagct tcccagagc                                           19

<210> SEQ ID NO 33
<211> LENGTH: 19
<212> TYPE: DNA
<213> ORGANISM: Human cytomegalovirus

<400> SEQUENCE: 33
ggctctggga agctgcggc                                           19

<210> SEQ ID NO 34
<211> LENGTH: 24
<212> TYPE: DNA
<213> ORGANISM: Human cytomegalovirus

<400> SEQUENCE: 34
cacaaaaatc cgccgattca gatc                                     24

<210> SEQ ID NO 35
<211> LENGTH: 19
<212> TYPE: DNA
<213> ORGANISM: Human cytomegalovirus

<400> SEQUENCE: 35
cggcgacgca cctgccacg                                           19

<210> SEQ ID NO 36
<211> LENGTH: 19
<212> TYPE: DNA
<213> ORGANISM: Human cytomegalovirus

<400> SEQUENCE: 36
cacagccggc gacgcacct                                           19

<210> SEQ ID NO 37
```

```
<211> LENGTH: 24
<212> TYPE: DNA
<213> ORGANISM: Human cytomegalovirus

<400> SEQUENCE: 37
ggtaaataaa ctccgtcgtg aggc                                              24

<210> SEQ ID NO 38
<211> LENGTH: 21
<212> TYPE: DNA
<213> ORGANISM: Human cytomegalovirus

<400> SEQUENCE: 38
ctggccccaa gtagcgagaa a                                                 21

<210> SEQ ID NO 39
<211> LENGTH: 19
<212> TYPE: DNA
<213> ORGANISM: Human cytomegalovirus

<400> SEQUENCE: 39
ggcgctgccg agcgactgg                                                    19

<210> SEQ ID NO 40
<211> LENGTH: 19
<212> TYPE: DNA
<213> ORGANISM: Human cytomegalovirus

<400> SEQUENCE: 40
gcgggataag acggcaaag                                                    19

<210> SEQ ID NO 41
<211> LENGTH: 20
<212> TYPE: DNA
<213> ORGANISM: Human cytomegalovirus

<400> SEQUENCE: 41
acgtagtccg caaagtgacg                                                   20

<210> SEQ ID NO 42
<211> LENGTH: 20
<212> TYPE: DNA
<213> ORGANISM: Human cytomegalovirus

<400> SEQUENCE: 42
ttcatccata ccgcccggag                                                   20

<210> SEQ ID NO 43
<211> LENGTH: 20
<212> TYPE: DNA
<213> ORGANISM: Human cytomegalovirus

<400> SEQUENCE: 43
aatggcatcc cgcagttcat                                                   20

<210> SEQ ID NO 44
<211> LENGTH: 25
<212> TYPE: DNA
<213> ORGANISM: Human cytomegalovirus

<400> SEQUENCE: 44
ccgaaagtaa cgtagaactc tgccg                                             25
```

```
<210> SEQ ID NO 45
<211> LENGTH: 22
<212> TYPE: DNA
<213> ORGANISM: Human cytomegalovirus

<400> SEQUENCE: 45
agagccgccg aaagtaacgt ag                                              22

<210> SEQ ID NO 46
<211> LENGTH: 25
<212> TYPE: DNA
<213> ORGANISM: Human cytomegalovirus

<400> SEQUENCE: 46
cgattcagat ctaccatgtc tttgg                                           25

<210> SEQ ID NO 47
<211> LENGTH: 24
<212> TYPE: DNA
<213> ORGANISM: Human cytomegalovirus

<400> SEQUENCE: 47
cacaaaaatc cgccgattca gatc                                            24

<210> SEQ ID NO 48
<211> LENGTH: 18
<212> TYPE: DNA
<213> ORGANISM: Human cytomegalovirus

<400> SEQUENCE: 48
tcgagcttat tgagcgca                                                   18

<210> SEQ ID NO 49
<211> LENGTH: 27
<212> TYPE: DNA
<213> ORGANISM: Human cytomegalovirus

<400> SEQUENCE: 49
tgaacttcat catcaccacc cgagact                                         27

<210> SEQ ID NO 50
<211> LENGTH: 27
<212> TYPE: DNA
<213> ORGANISM: Human cytomegalovirus

<400> SEQUENCE: 50
ccttgtacgc tttggaaatc gagcctg                                         27

<210> SEQ ID NO 51
<211> LENGTH: 22
<212> TYPE: DNA
<213> ORGANISM: Human cytomegalovirus

<400> SEQUENCE: 51
cgacgattca gtcctgcgag cc                                              22

<210> SEQ ID NO 52
<211> LENGTH: 20
<212> TYPE: DNA
<213> ORGANISM: Human cytomegalovirus

<400> SEQUENCE: 52
aagccgccgc agcttcccag                                                 20
```

```
<210> SEQ ID NO 53
<211> LENGTH: 18
<212> TYPE: DNA
<213> ORGANISM: Cucurbita pepo
<220> FEATURE:
<221> NAME/KEY: misc_feature
<222> LOCATION: (2)..(3)
<223> OTHER INFORMATION: N is 5-propynyl dU
<220> FEATURE:
<221> NAME/KEY: misc_feature
<222> LOCATION: (7)..(9)
<223> OTHER INFORMATION: N is 5-propynyl dU
<220> FEATURE:
<221> NAME/KEY: misc_feature
<222> LOCATION: (11)..(11)
<223> OTHER INFORMATION: N is 5-propynyl dU
<220> FEATURE:
<221> NAME/KEY: misc_feature
<222> LOCATION: (13)..(14)
<223> OTHER INFORMATION: N is 5-propynyl dU

<400> SEQUENCE: 53
cnncacnnnc ncnngcag                                                 18

<210> SEQ ID NO 54
<211> LENGTH: 23
<212> TYPE: DNA
<213> ORGANISM: Cucurbita pepo

<400> SEQUENCE: 54
acaaatttgg aagccatgca tca                                           23

<210> SEQ ID NO 55
<211> LENGTH: 25
<212> TYPE: DNA
<213> ORGANISM: Cucurbita pepo

<400> SEQUENCE: 55
aagctgacga gttcatgagg gcagg                                         25

<210> SEQ ID NO 56
<211> LENGTH: 27
<212> TYPE: DNA
<213> ORGANISM: Human cytomegalovirus

<400> SEQUENCE: 56
acttcatcat caccacccga gacttct                                       27

<210> SEQ ID NO 57
<211> LENGTH: 26
<212> TYPE: DNA
<213> ORGANISM: Human cytomegalovirus

<400> SEQUENCE: 57
tgtacgcttt ggaaatcgag cctgcc                                        26

<210> SEQ ID NO 58
<211> LENGTH: 25
<212> TYPE: DNA
<213> ORGANISM: Human cytomegalovirus

<400> SEQUENCE: 58
acgattcagt cctgcgagcc gccga                                         25

<210> SEQ ID NO 59
<211> LENGTH: 20
```

```
<212> TYPE: DNA
<213> ORGANISM: Human cytomegalovirus

<400> SEQUENCE: 59
ctgggaagct gcggcggctt                                              20

<210> SEQ ID NO 60
<211> LENGTH: 20
<212> TYPE: DNA
<213> ORGANISM: Human cytomegalovirus

<400> SEQUENCE: 60
ctctgggaag ctgcggcggc                                              20

<210> SEQ ID NO 61
<211> LENGTH: 1224
<212> TYPE: DNA
<213> ORGANISM: Human cytomegalovirus

<400> SEQUENCE: 61
atgaacttca tcatcaccac ccgagacttc tccaacgacg attcagtcct gcgagccgcc     60
gagatgcgtg acaacgtggc aggctcgatt tccaaagcgt acaagggcac ggtacgcgcc    120
gaaggcaaga agaagctgct gctgaagcac ttgcccgtgc cgccggcgg ctgctcgcgc     180 cgcaacagca acctcttcgt tttctgcacc gagcgcgact accgcaagtt ccaccagggc    240
atcgcacagc tcaagcgcgc gccggccgaa ctggaccccc acgagatcca gcaagtcacg    300
gccagtatcc gctgccgcct gcagcccagt ctccgcgagc cgcccacgcc ggccgacgag    360
ctgcagacgg ctgtgtcgcg cgtgtgcgcg ctcttcaacc agctggtttt cacggcccag    420
ctgcgccact actgcgagca ccaggacaag gtggtgagct acgcgcgcga cgagttgacc    480
aaacgctgcg gcgaaaaatc ggcgctgggc gtagaggtgc atcaactggt agccttgctg    540
ccacacgagc gccaccgcga actgtgccac gtcctcatcg gcttgttgca ccagacgccg    600
cacatgtggg cgcgctccat ccgtctcatc ggacacctgc gccactacct gcagaacagc    660
ttcctacacc tgttgatgaa ctcaggtttg gatatcgcac aagtcttcga cggctgttac    720
cacagcgagg cctaccgcat gctcttccag atcggtcata cggactcggt gtcggcggcc    780
ctggaactct cacacagcgc ggcggccggg ccgcccgagg ccgatgagaa caacgacgag    840
ggagaggagg acgacgacga gctccgtcac agcgaccccg gcgccgcttca cgattccaag    900 aagccccgca cgcccgtcg tccccgcaca cgcgtgccgc ctcacgagca aaagcccgaa    960
gaaaacgagg aggaagaaga ggagctgttt ccctcctgca aggcaaccgc agcattcctg   1020
cgggcagaac cctccgtctc caacgacgac ggcaacggtg gcgaacgctg cgacacgcta   1080
gcgaccgccc tgcggcatcg cgccgacgaa gaagacggac tctagccag ccagacctct   1140 gtgcgagtcg ccgcgacccc ctcaccttca gtcacctcag cccttacccc cgtcacgtcc   1200
cccataaccc cgttgtgtat ttaa                                          1224

<210> SEQ ID NO 62
<211> LENGTH: 1224
<212> TYPE: DNA
<213> ORGANISM: Human cytomegalovirus

<400> SEQUENCE: 62
atgaacttca tcatcaccac ccgagacttc tccaacgacg attcagtcct gcgagccgcc     60
gagatgcgtg acaacgtggc aggctcgatt tccaaagcgt acaagggcac ggtacgcgcc    120
```

```
gaaggcaaga agaagctgct gctgaagcac ttgcccgtgc cgcccggcgg ctgctcgcgc        180
cgcaacagca acctcttcgt tttctgcacc gagcgcgact accgcaagtt ccaccagggc        240
atcgcacagc tcaagcgcgc gccggccgaa ctggaccccc acgagatcca gcaagtcacg        300
gccagtatcc gctgccgcct gcagcccagt ctccgcgagc cgcccacgcc ggccgacgag        360
ctgcagacgg ctgtgtcgcg cgtgtgcgcg ctcttcaacc agctggtttt cacggcccag        420
ctgcgccact actgcgagca ccaggacaag gtggtgagct acgcgcgcga cgagctgact        480
aaacgctgcg gcgaaaaatc ggcgctgggc gtggaagtgc atcaactggt agccctgctg        540
ccacacgagc gccaccgcga actgtgccac gtcctcatcg gcttgttgca ccagacgccg        600
cacatgtggg cgcgctccat ccgtctcatc ggacacctgc cgactacct gcagaacagc         660 ttcctacacc tgttgatgaa ctcaggtttg gatatcgcac aagttttcga cggctgttac        720
cacagcgagg cctaccgcat gctcttccag atcggtcata cggactcggt gtcggcggcc        780
ctggaactct cacacggcgc ggcggccggg ccgcccgagg ccgatgaaaa caacgacgag        840
ggagaggagg acgacgacga gctccgtcac agcgacccgg cgccgcttca cgagtccaag        900
aagccccgca acgcccgtcg tccccgcaca cgcgtgccgc ctcacgagca aaagcccgaa        960
gaaaacgagg aggaagaaga ggagctgttt ccctcctgca aggcaaccgc agcattcctg       1020
cgggcagaac cctccgtctc caacgacgac ggcaacggcg cgaacgctg cgacacgcta        1080 gcgaccgccc tgcggcatcg cgccgacgaa gaagacggac tctagccag ccagaccgct        1140 gtgcgggtcg ccgcgacccc ctcaccttca gtcacccag cccttacccc cgtcacgtcc        1200
cccataaccc cgttgtgtat ttaa                                              1224

<210> SEQ ID NO 63
<211> LENGTH: 1224
<212> TYPE: DNA
<213> ORGANISM: Human cytomegalovirus

<400> SEQUENCE: 63
atgaacttca tcatcaccac ccgagacttc tccaacgacg attcagtcct gcgagccgcc         60
gagatgcgtg acaacgtggc aggctcgatt tccaaagcgt acaagggtac ggtacgcgcc        120
gaaggcaaga agaagctgct gctgaagcac ttgcccgtgc cgcccggcgg ctgctcgcgc        180
cgcaacagca acctcttcgt tttctgcacc gagcgcgact accgcaagtt ccaccagggc        240
atcgcacagc tcaagcgcgc gccggccgaa ctggaccccc acgagatcca gcaagtcacg        300
gccagtatcc gctgccgcct gcagcccagt ctccgcgagc cgcccacgcc ggccgacgag        360
ctgcagacgg ctgtgtcgcg cgtgtgcgcg ctcttcaacc agttggtttt cacggcccag        420
ctgcgccact actgcgagca ccaggacaag gtggtgagct acgcgcgcga cgagctgact        480
aaacgctgcg gcgaaaaatc ggcgctgggc gtggaggtgc atcaactggt agccctgctg        540
ccacacgagc gccaccgcga actgtgccac gtcctcatcg gcttgttgca ccagacgccg        600
cacatgtggg cgcgctccat ccgtctcatc ggacacctgc cgactacct gcagaacagc         660 ttcctacacc tgttgatgaa ctcaggtttg gatatcgcgc aagtcttcga cggctgttac        720
cacagcgagg cctaccgcat gctcttccag atcggtcata cggactcggt gtcggcggcc        780
ctggaacttt cacacagcgc ggcggccggg ccgcccgagg ccgatgagaa caacgacgaa        840
ggagaggagg acgacgacga gctccgtcac agcgacccgg cgccgcttca cgagtccaag        900
aagccccgca acgcccgtcg tccccgcaca cgcgtgccgc ctcacgagca aaagcccgaa        960
gaaaacgagg aggaagaaga ggagctgttt ccctcctgca aggcaaccgc agcattcctg       1020
```

```
cgggcagaac cctccgtctc caacgacgac ggcaacggcg gcgaacgctg cgacacgcta   1080
gcgaccgccc tgcggcattg cgccgacgaa gaagacggac tctagccag ccagaccgct   1140 gtgcgggtcg ccgcgacccc ctcaccttca gtcacccag cccttacccc cgtcacgtcc   1200
cccataaccc cgttgtgtat ttaa                                            1224

<210> SEQ ID NO 64
<211> LENGTH: 1224
<212> TYPE: DNA
<213> ORGANISM: Human cytomegalovirus

<400> SEQUENCE: 64
atgaacttca tcatcaccac ccgagacttc tccaacgacg attcagtcct gcgagccgcc    60
gagatgcgtg acaacgtggc aggctcgatt tccaaagcgt acaagggcac ggtacgcgcc   120
gaaggcaaga agaagctgct gctgaagcac ttgcccgtac cgcccggcgg ctgctcgcgc   180
cgcaacagca acctcttcgt tttctgcacc gagcgcgatt accgcaagtt ccaccagggc   240
atcgcacagc tcaagcgcgc gccggccgaa ctggaccccc acgagatcca gcaagtcacg   300
gccagtatcc gctgccgcct gcagcccagt ctccgcgagc cgcccacgcc ggccgacgag   360
ctgcagacgg ctgtgtcgcg cgtgtgcgcg ctcttcaacc agctggtttt cacggcccag   420
ctgcgccact actgcgagca ccaggacaag gtggtgagct acgcgcgcga cgaactgact   480
aaacgctgcg gcgaaaaatc ggcgctgggc gtggaagtgc atcaactggt agccctgctg   540
ccacacgagc gccaccgcga actgccac gtcctcatcg gcttgttgca ccagacgccg   600
cacatgtggg cgcgctccat ccgtctcatc ggacacctgc gccactacct gcagaacagc   660
ttcctacacc tgttgatgaa ctcaggtttg gatatcgcac aagttttcga cggctgttac   720
cacagcgagg cctaccgcat gctcttccag atcggtcata cggactcggt gtcggcagcc   780
ctggaattct cacacagcgc ggcggccggg ccgcccgagg ccgatgagaa caacgacgag   840
ggagaggagg acgacgacga gctccgtcac agcgacccgg cgccgcttca cgagtccaag   900
aagccccgca cgcccgtcg tccccgcaca cgcatgccgc ctcacgagca aaagcccgaa   960
gaaaacgagg aggaagaaga ggagctgttt ccctcctgca aggcaaccgc agcattcctg   1020
cgggcagaac cctccgtctc caacgacgac ggcaacggcg gcgaacgctg cgacacgcta   1080
gcgaccgccc tgcggcattg cgccgacgaa gaagacggac tctagccag ccagaccgct   1140 gtgcgggtcg ccgcgacccc ctcaccttca gtcacccag cccttacccc cgtcacgtcc   1200
cccataaccc cgttgtgtat ttaa                                            1224

<210> SEQ ID NO 65
<211> LENGTH: 1224
<212> TYPE: DNA
<213> ORGANISM: Human cytomegalovirus

<400> SEQUENCE: 65
atgaacttca tcatcaccac ccgagacttc tccaacgacg attcagtcct gcgagccgcc    60
gagatgcgtg acaacgtggc aggctcgatt tccaaagcgt acaagggcac ggtacgcgcc   120
gaaggcaaga agaagctgct gctgaagcac ttgcccgtgc cgcccggcgg ctgctcgcgc   180
cgcaacagca acctcttcgt tttctgcacc gagcgcgact accgcaagtt ccaccagggc   240
atcgcacagc tcaagcgcgc gccggccgaa ctggaccccc acgagatcca gcaagtcacg   300
gccagtatcc gctgccgcct gcagcccagt ctccgcgagc cgcccacgcc ggccgacgaa   360
```

```
ctgcagacgg ctgtgtcgcg cgtgtgcgcg ctcttcaacc agctggtttt cacggcccag    420
ctgcgccact actgcgagca ccaggacaag gtggtgagct acgcgcgcga cgagttgacc    480
aaacgctgcg gcgaaaaatc ggcgctgggc gtagaggtgc atcaactggt agccttgctg    540
ccacacgagc gccaccgcga actgtgccac gtcctcatcg gcttgttgca ccagacgccg    600
cacatgtggg cgcgctccat ccgtctcatc ggacacctgc gccactacct gcagaacagc    660
ttcctacacc tgttgatgaa ctcaggtttg gatatcgcac aagtcttcga cggctgttac    720
cacagcgagg cctaccgcat gctcttccag atcggtcata cggactcggt gtcggcggcc    780
ctggaactct cacacagcgc ggcggccggg ccgcccgagg ccgatgagaa caacgacgag    840
ggagaggagg acgacgacga gctccgtcac agcgacccgg cgccgcttca cgattccaag    900 aagcccccgca acgccgtcg tccccgcaca cgcgtgccgc ctcacgagca aaagcccgaa    960
gaaaacgagg aggaagaaga ggagctgttt ccctcctgca aggcaaccgc agcattcctg   1020
cgggcagaac cctccgtctc caacaacgac ggcaacggtg gcgaacgctg cgacacgcta   1080
gcgaccgccc tgcggcatcg cgccgacgaa gaagacggac ctctagccag ccagacctct   1140
gtgcgagtcg ccgcgacccc ctcaccttca gtcacctcag cccttacccc cgtcacgtcc   1200
cccataaccc cgttgtgtat ttaa                                          1224

<210> SEQ ID NO 66
<211> LENGTH: 1224
<212> TYPE: DNA
<213> ORGANISM: Human cytomegalovirus

<400> SEQUENCE: 66
atgaacttca tcatcaccac ccgagacttc tccaacgacg attcagtcct gcgagccgcc     60
gagatgcgtg acaacgtggc aggctcgatt tccaaagcgt acaagggcac ggtacgcgcc    120
gaaggcaaga agaagctgct gctgaagcac ttgcccgtgc cgcccggcgg ctgctcgcgc    180
cgcaacagca acctcttcgt tttctgcacc gagcgcgact accgcaagtt ccaccagggc    240
atcgcacagc tcaagcgcgc gccggccgaa ctggaccccc acgagatcca gcaagtcacg    300
gccagtatcc gctgccgcct gcagcccagt ctccgcgagc cgcccacgcc ggccgacgaa    360
ctgcagacgg ctgtgtcgcg cgtgtgcgcg ctcttcaacc agctggtttt cacggcccag    420
ctgcgccact actgcgagca ccaggacaag gtggtgagct acgcgcgcga cgagttgacc    480
aaacgctgcg gcgaaaaatc ggcgctgggc gtagaggtgc atcaactggt agccttgctg    540
ccacacgagc gccaccgcga actgtgccac gtcctcatcg gcttgttgca ccagacgccg    600
cacatgtggg cgcgctccat ccgtctcatc ggacacctgc gccactacct gcagaacagc    660
ttcctacacc tgttgatgaa ctcaggtttg gatatcgcac aagtcttcga cggctgttac    720
cacagcgagg cctaccgcat gctcttccag atcggtcata cggactcggt gtcggcggcc    780
ctggaactct cacacagcgc ggcggccggg ccgcccgagg ccgatgagaa caacgacgag    840
ggagaggagg acgacgacga gctccgtcac agcgacccgg cgccgcttca cgattccaag    900 aagcccccgca acgccgtcg tccccgcaca cgcgtgccgc ctcacgagca aaagcccgaa    960
gaaaacgagg aggaagaaga ggagctgttt ccctcctgca aggcaaccgc agcattcctg   1020
cgggcagaac cctccgtctc caacaacgac ggcaacggtg gcgaacgctg cgacacgcta   1080
gcgaccgccc tgcggcatcg cgccgacgaa gaagacggac ctctagccag ccagacctct   1140
gtgcgagtcg ccgcgacccc ctcaccttca gtcacctcag cccttacccc cgtcacgtcc   1200
cccataaccc cgttgtgtat ttaa                                          1224
```

<210> SEQ ID NO 67
<211> LENGTH: 1224
<212> TYPE: DNA
<213> ORGANISM: Human cytomegalovirus

<400> SEQUENCE: 67

```
atgaacttca tcatcaccac ccgagacttc tccaacgacg attcagtcct gcgagccgcc        60
gagatgcgtg acaacgtggc aggctcgatt tccaaagcgt acaagggcac ggtacgcgcc       120
gaaggcaaga agaagctgct gctgaagcac ttgcccgtgc cgcccggcgg ctgctcgcgc       180
cgcaacagca acctcttcgt tttctgcacc gagcgcgact accgcaagtt ccaccagggc       240
atcgcacagc tcaagcgcgc gccggccgaa ctggacccccc acgagatcca gcaagtcacg       300
gccagtatcc gctgccgcct gcagcccagt ctccgcgagc cgcccacgcc ggccgacgag       360
ctgcagacgg ctgtgtcgcg cgtgtgcgcg ctcttcaacc agctggtttt cacggcccag       420
ctgcgccact actgcgagca ccaggacaag gtggtgagct acgcgcgcga cgagttgacc       480
aaacgctgcg gcgaaaaatc ggcgctgggc gtggaggtgc atcaactggt agccttgctg       540
ccacacgagc gccaccgcga actgtgccac gtcctcatcg gcttgttgca ccagacgccg       600
cacatgtggg cgcgctccat ccgtctcatc ggacacctgc gccactacct gcagaacagc       660
ttcctacacc tgttgatgaa ctcaggtttg gatatcgcac aagttttcga cggctgttac       720
cacagcgagg cctaccgcat gctcttccag atcggtcata cggactcggt gtcggcggcc       780
ctggaactct cacacagcgc agcggccggg ccgcccgagg ccgatgagaa caacgacgag       840
ggagaggagg acgacgacga gctccgtcac agcgacccgg cgccgcttca cgagtccaag       900
aagccccgca acgcccgccg tccccgcaca cgcatgccgc ctcacgagca aaagcccgaa       960
gaaaacgagg aggaagaaga ggagctgttt ccctcctgca aggcaaccgc agcattcctg      1020
cgggcagaac cctccgtctc caacgacgac ggcaacggcg gcgaacgctg cgacacgcta      1080
gcgaccgccc tgcggcattg cgccgacgaa gaagacggac ctctagccag ccagaccgct      1140
gtgcgggtcg ccgcgacccc ctcaccttca gtcaccccag cccttacccc cgtcacgtcc      1200
cccataaccc cgttgtgtat ttaa                                             1224
```

<210> SEQ ID NO 68
<211> LENGTH: 1224
<212> TYPE: DNA
<213> ORGANISM: Human cytomegalovirus

<400> SEQUENCE: 68

```
atgaacttca tcatcaccac ccgagacttc tccaacgacg attcagtcct gcgagccgcc        60
gagatgcgtg acaacgtggc aggctcgatt tccaaagcgt acaagggcac ggtacgcgcc       120
gaaggcaaga agaagctgct gctgaagcac ttgcccgtgc cgcccggcgg ctgctcgcgc       180
cgcaacagca acctcttcgt tttctgcacc gaacgcgact accgcaagtt ccaccagggc       240
atcgcacagc tcaagcgcgc gccggccgaa ctggacccccc acgagatcca gcaagtcacg       300
gccagtatcc gctgccgcct gcagcccagt ctccgcgagc cgcccacgcc ggccgacgag       360
ctgcagacgg ctgtgtcgcg cgtgtgcgcg ctcttcaacc agctggtttt cacggcccag       420
ctgcgccact actgcgagca ccaggacaag gtggtgagct acgcgcgcga cgagttgacc       480
aaacgctgcg gcgaaaaatc ggcgctgggc gtggaggtgc atcaactggt agccttgctg       540
ccacacgagc gccaccgcga actgtgccac gtcctcatcg gcttgttgca ccagacgccg       600
```

-continued

| | |
|---|---|
| cacatgtggg cgcgctccat ccgtctcatc ggacacctgc gccactacct gcagaacagc | 660 |
| ttcctacacc tgttgatgaa ctcaggtttg gatatcgcgc aagtcttcga cggctgttac | 720 |
| cacagcgagg cctaccgcat gctcttccag atcggtcata cggactcggt gtcggcggcc | 780 |
| ctggaactct cacacagcgc ggcggccggg ctgcccgagg ccgatgagaa caacgacgag | 840 |
| ggagaggagg acgacgacga gctccgtcac agcgacccgg cgccgcttca cgagtccaag | 900 |
| aagccccgca acgccgtcg tccccgcaca cgcatgccgc ctcacgagca aaagcccgaa | 960 |
| gaaaacgagg aggaagaaga ggagctgttt ccctcctgca aggcaaccgc agcattcctg | 1020 |
| cgggcagaac cctccgtctc caacgacgac ggcaacggcg gcgaacgctg cgacacgcta | 1080 |
| gcgaccgccc tgcggcattg cgccgacgaa gaagacggac ctctagccag ccagaccgct | 1140 |
| gtgcgggtcg ccgcgacccc ctcaccttca gtcaccccag cccttacccc cgtcacgtcc | 1200 |
| cccataaccc cgttgtgtat ttaa | 1224 |

<210> SEQ ID NO 69
<211> LENGTH: 2127
<212> TYPE: DNA
<213> ORGANISM: Human cytomegalovirus

<400> SEQUENCE: 69

| | |
|---|---|
| atgacgatgg acgagcagca gtcgcaggct gtggcgccgg tctacgtggg cggctttctc | 60 |
| gcccgctacg accagtctcc ggacgaggcc gaattgctgt tgccgcggga cgtagtggag | 120 |
| cactggttgc acgcgcaggg ccagggacag ccttcgttgt cggtcgcgct cccgctcaac | 180 |
| atcaaccacg acgacacggc cgttgtagga cacgttgcgg cgatgcagag cgtccgcgac | 240 |
| ggtcttttttt gcctgggctg cgtcacttcg cccaggtttc tggagattgt acgccgcgct | 300 |
| tcggaaaagt ccgagctggt ttcgcgcggg ccgtcagtc cgctgcagcc agacaaggtg | 360 |
| gtggagtttc tcagcggcag ctacgccggc ctctcgctct ccagccggcg ctgcgacgac | 420 |
| gtggaggccg cgacgtcgct ttcgggctcg gaaaccacgc cgttcaaaca cgtggctttg | 480 |
| tgcagcgtgg gtcggcgtcg cggtacgttg gccgtgtacg ggcgcgatcc cgagtgggtc | 540 |
| acacagcggt ttccagacct cacggcgcc gaccgtgacg ggctacgtgc acagtggcag | 600 |
| cgctgcggca gcactgctgt cgacgcgtcg ggcgatccct ttcgctcaga cagctacggc | 660 |
| ctgtttgggca acagcgtgga cgcgctctac atccgtgagc gactgcccaa gctgcgctac | 720 |
| gacaagcaac tagtcggcgt gacggagcgc gagtcgtacg tcaaggcgag cgtttcgcct | 780 |
| gaggcggcgt gcgttattaa agcggcgtcc gccgagcgtt cgggcgacag ccgcagtcag | 840 |
| gccgccacgc cggcggctgg ggcgcgcgtt ccctcttcgt ccccgtcgcc tccagtcgaa | 900 |
| ccgccatctc ctgtacagcc gcctgcgctt ccagcgtcgc cgtccgttct tcccgcggaa | 960 |
| tcaccgccgt cgctttctcc ctcggagccg gcagaggcgg cgtccatgtc gcaccctctg | 1020 |
| agtgctgcgg ttcccgccgc tacggctcct ccaggtgcta ccgtggcagg tgcgtcgccg | 1080 |
| gctgtgtcgt ctctagcgtg gcctcacgac ggagtttatt tacccaaaga cgcttttttc | 1140 |
| tcgctacttg gggccagtcg ctcggcagcg cccgtcatgt atcccggcgc cgtagcggcc | 1200 |
| cctccttctg cttcgccagc accgctgcct ttgccgtctt atcccgcgtc ctacggcgcc | 1260 |
| cccgtcgtgg gttacgacca gttggcggca cgtcactttg cggactacgt ggatccccat | 1320 |
| tatcccgggt ggggtcggcg ttacgagccc cgccgtcctt tgcatccgtc ttatcccgtg | 1380 |
| ccgccgccac catcaccggc ctattaccgt cggcgcgact ctccgggcgg tatggatgaa | 1440 |
| ccaccgtccg gatgggagcg ttacgacggt ggtcaccgtg gtcagtcgca gaagcagcac | 1500 |

```
cgtcacgggg gcagcggcgg acacaacaaa cgccgtaagg aaaccgcggc ggcgtcgtcg      1560
tcgtcctcgg acgaagactt gagtttccca ggcgaggccg agcacggccg ggcacgaaag      1620
cgtctaaaaa gtcacgtcaa tagcgacggt ggaagtggcg ggcacgcggg ttccaatcag      1680
cagcagcaac aacgttacga tgaactgcgg gatgccattc acgagctgaa acgcgatctg      1740
tttgccgcgc ggcagagttc tacgttactt tcggcggctc tcccctctgc ggcctcttcc      1800
tccccaacta ctactaccgt gtgtactccc accagcgagc tgacgagtgg cggaggagaa      1860
acacccacgg cacttctatc cggaggtgcc aaggtagctg agcgcgctca ggccggcgtg      1920
gtgaacgcca gttgccgcct cgctaccgcg tcgggttctg aggcggcaac ggccgggccc      1980
tcgacggcag gttcttcttc ctgcccggct agtgtcgtgt tagccgccgc tgctgcccaa      2040
gccgccgcag cttcccagag cccgcccaaa gacatggtag atctgaatcg gcggattttt      2100
gtggctgcgc tcaataagct cgagtaa                                          2127
```

<210> SEQ ID NO 70
<211> LENGTH: 2127
<212> TYPE: DNA
<213> ORGANISM: Human cytomegalovirus

<400> SEQUENCE: 70

```
atgacgatgg acgagcagca gtcgcaggct gtggcgccgg tctacgtggg cggctttctc       60
gcccgctacg accagtctcc ggacgaggcc gaattgctgt tgccgcggga cgtagtggag      120
cactggttgc acgcgcaggg ccagggacag ccttcgttgt cggtcgcgct cccgctcaac      180
atcaaccacg acgacacggc cgttgtagga cacgttgcgg cgatgcagag cgtccgcgac      240 ggtcttttt gcctgggctg cgtcacttcg cccaggtttc tggagattgt acgccgcgct      300
tcggaaaagt ccgagctggt ttcgcgcggg cccgtcagtc cgctgcagcc agacaaggtg      360
gtggagtttc tcagcggcag ctacgccggc ctctcgctct ccagccgcg ctgcgacgac       420 gtggaggccg cgacgtcgct ttcgggctcg gaaaccacgc cgttcaaaca cgtggctttg      480
tgcagcgtgg gtcggcgtcg cggtacgttg gccgtgtacg ggcgcgatcc cgagtgggtc      540
acacagcggt ttccagacct cacggcggcc gaccgtgacg ggctacgtgc acagtggcag      600
cgctgcggca gcactgctgt cgacgcgtcg ggcgatccct ttcgctcaga cagctacggc      660
ctgttgggca cagcgtggga cgcgctctac atccgtgagc gactgcccaa gctgcgctac      720
gacaagcaac tagtcggcgt gacggagcgc gagtcatacg tcaaggcgag cgtttcgcct      780
gaggcggcgt gcgatattaa agcggcgtcc gccgagcgtt cgggcgacag ccgcagtcag      840
gccgccacgc cggcggctgg ggcgcgcgtt ccctcttcgt ccccgtcgcc tccagtcgaa      900
ccgccatctc ctgtacagcc gcctgcgctt ccagcgtcgc cgtccgttct tcccgcggaa      960
tcaccgccgt cgcttttctcc ctcggagccg gcagaggcgg cgtccatgtc gcaccctctg     1020
agtgctgcgg ttcccgccgc tacgctcct ccaggtgcta ccgtggcagg tgcgtcgccg      1080
gctgtgtcgt ctctagcgtg gcctcacgac ggagttttatt acccaaaga cgcttttttc      1140 tcgctacttg gggccagtcg ctcggcagtg cccgtcatgt atccccggcgc cgtagcggcc      1200 cctccttctg cttcgccagc accgctgcct ttgccgtctt atcccgcgtc ctacggcgcc      1260
cccgtcgtgg gttacgacca gttggcggca cgtcactttg cggactacgt ggatccccat      1320
tatcccgggt ggggtcggcg ttacgagccc gcgccgtctt tgcatccgtc ttatcccgtg      1380
ccgccgccac catcaccggc ctattaccgt cggcgcgact ctccgggcgg tatggatgaa      1440
```

| | |
|---|---|
| ccaccgtccg gatgggagcg ttacgacggt ggtcaccgtg gtcagtcgca gaagcagcac | 1500 |
| cgtcacgggg gcagcggcgg acacaacaaa cgccgtaagg aaaccgcggc ggcgtcgtcg | 1560 |
| tcgtcctcgg acgaagactt gagtttccca ggcgaggccg agcacggccg ggcacgaaag | 1620 |
| cgtctaaaaa gtcacgtcaa tagcgacggt ggaagtggcg ggcacgcggg ttccaatcag | 1680 |
| cagcagcaac aacgttacga tgaactgcgg gatgccattc acgagctgaa acgcgatctg | 1740 |
| tttgctgcgc ggcagagttc tacgttactt tcggcggctc ttccctctgc ggcctcttcc | 1800 |
| tccccaacta ctactaccgt gtgtactccc accggcgagc tgacgagtgg cggaggagaa | 1860 |
| acacccacgg cacttctatc cggaggtgcc aaggtagctg agcgcgctca ggccggcgtg | 1920 |
| gtgaacgcca gttgccgcct cgctaccgcg tcgggttctg aggcggcaac ggccgggccc | 1980 |
| tcgacggcag gttcttcttc ctgcccggct agtgtcgtgt tagccgccgc tgctgcccaa | 2040 |
| gccgccgcag cttcccagag cccgcccaaa gacatggtag atctgaatcg gcggattttt | 2100 |
| gtggctgcgc tcaataagct cgagtaa | 2127 |

<210> SEQ ID NO 71
<211> LENGTH: 2124
<212> TYPE: DNA
<213> ORGANISM: Human cytomegalovirus

<400> SEQUENCE: 71

| | |
|---|---|
| atgacgatgg acgagcagca gccgcaggct gtgacgccgg tctacgtggg cggctttctc | 60 |
| gcccgttacg accagtctcc ggacgaggcc gaattgctgt tgccgcggga cgtagtggag | 120 |
| cactggttgc acgcgcaggg ccagggacag ccttcgttgt cggtcgcgct cccgctcaac | 180 |
| atcaaccacg acgacacggc cgttgtagga cacgttgcgg cgatgcagag cgttcgcgac | 240 |
| ggtcttttttt gtctaggttg cgtcacttcg cccaggtttc tggagattgt gcgccgcgct | 300 |
| tcggaaaagt ccgagctggt ttcgcgcggg cccgtcagtc cgctgcagcc ggacaaggtg | 360 |
| gtggagtttc tcagcggcag ctacgccggc ctctcgctct ccagccggcg ctgcgacgac | 420 |
| gtggaggccg cgacgtcgct ttcgggctcg gaaaccacgc cgttcaaaca cgtggctttg | 480 |
| tgcagcgtgg gtcggcgtcg cggtacgttg gctgtgtacg gacgcgatcc cgagtgggtt | 540 |
| acccagcggt ttccagacct cacggcggcc gaccgcgacg ggctacgtgc acagtggcag | 600 |
| cgctgcggca gcactgctgt cgacgcgtcg ggcgatccct ttcgctcaga cagctacggc | 660 |
| ctgttgggca acagcgtgga cgcgctctac atccgtgagc gactgcccaa gctgcgctac | 720 |
| gacaagcaac tagtcggcgt gacggagcgc gagtcgtacg tcaaggcgag cgtttcgcct | 780 |
| gaggcggcgt gcgatattaa agcggcgtcc gccgagcgtt cgggcgacag ccgcagtcag | 840 |
| gccgccacgc cggcggctgg ggcgcgtgtt ccctcttcat ccccgtcgcc tccagtcgaa | 900 |
| ccgccatctc ctgtccagcc gcctgcgctt ccagcgtcgc cgtccgttct ccccgcggaa | 960 |
| tcatcgccgt cgctttctcc ttcggagccg gcagaggcgg cgtccatgtc gcaccctctg | 1020 |
| agtgctgcgg ttaccgccgc tacggctcct ccaggtgcta ccgtggcagg tgcgtcgccg | 1080 |
| gctgtgccgt ctttagcgtg gcctcacgac ggagtttatt tacccaaaga cgcttttttc | 1140 |
| tcgctacttg gggccagtcg ctcggcagcg cccgtcatgt atcccggcgc cgtagcggcc | 1200 |
| cctccttctg cttcgccagc accgctgcct ttgccgtctt atcccgcgtc ctacggcgcc | 1260 |
| cccgtcgtgg gttacgacca gttgcggca cgtcactttg cggactacgt ggatccccat | 1320 |
| tatcccgggt ggggtcggcg ttacgagccc cgccgtctct tgcatccgtc ttatcccgtg | 1380 |
| ccgccgccac catcaccggc ctattaccgt cggcgcgact ctccgggcgg tatggatgaa | 1440 |

```
ccaccgtccg gatgggagcg ttacgacggt agtcaccgtg gtcagtcgca gaagcagcac    1500
cgtcacgggg gcagcggcgg acacaacaaa cgccgtaagg aagccgcggc ggcgtcgtcg    1560
tcctcggacg aagacttgag tttccccggc gaggccgagc acggccgggc gcgaaagcgt    1620
ctaaaaagtc acgtcaatag cgacggtgga agtggcgggc acgcggggttc caatcagcag   1680 cagcaacaac gttacgatga actgcgggat gccattcacg agctgaaacg cgatctgttt    1740
gccgcgcggc agagttctac gttactttcg gcggctctcc ccgctgcggc ctcttcctcc    1800
ccgactacta ctaccgtgtg tactcccacc ggcgagctga cgagcggcgg aggagaaaca    1860
ccgacggcac ttctatcagg aggtgccaag gtagctgagc gcgctcaggc cggtgtggtg    1920
aacgccagtt gccgcctcgc taccgcgtcg ggttctgagg cggcaacggc agggccttcg    1980
acggcgggtt cttcttcctg cccggctagt gtcgtgttag ccgccgctgc tgcccaagcc    2040
gccgcagctt cccagagccc gcccaaagac atggtggatc tgaatcggcg gattttttgtg   2100 gctgcgctca ataagctcga gtaa                                          2124
```

<210> SEQ ID NO 72
<211> LENGTH: 2130
<212> TYPE: DNA
<213> ORGANISM: Human cytomegalovirus

<400> SEQUENCE: 72

```
atgacgatgg acgagcaaca gccgcaggct gtggcgccgg tctacgtggg cggctttctc     60
gcccgctacg accagtctcc ggacgaggcc gaattgctgt tgccgcggga cgtagtggag    120
cactggttgt atgcgcagag ccagggacag ccttcgttgt cggtcgcgct cccgctcaac    180
atcaaccacg acgtatacggc cgttgtagga cacgttgcgg cgatgcagag cgtccgcgac   240 ggtcttttttt gcctgggctg cgtcacttcg cccaggtttc tggagattgt acgccgcgct   300
tcggaaaagt ccgagctggt ttcgcgcggg ccgtcagtc cgctgcagcc agacaaggtg    360
gtggagtttc tcagcggcag ctacgccggc ctctcgctct ccagccggcg ctgcgacgac    420
gtggaggccg cgacgtcgct ttcgggctcg gaaaccacgc cgttcaaaca cgtggctttg    480
tgcagcgtgg gtcggcgtcg cggtacgttg gccgtgtacg ggcgcgatcc cgagtgggtc    540
acccagcggt ttccagacct cacgcggcc gaccgcgacg ggctacgtgc acagtggcag    600
cgctgcggca gcactgctgt cgacgcgtcg ggcgatccct ttcgctcaga cagctacggc    660
ctgttgggca acagcgtgga cgcgctctac atccgtgagc gactgcccaa gctgcgctac    720
gacaagcaac tagtcggcgt gacggagcgc gagtcgtacg tcaaggcgag cgtttcgcct    780
gaggcggcgt gcgatattaa agcggcgtcc gccgagcgtt cgggcgacag ccgcagtcag    840
gccgccacgc cggcgactgg ggcgcgcgtt cctcttcgt ccccgtcgcc tccagtcgaa    900
ccgccatctc ctgtccagcc gcctgcgctt ccagcgtcgc cgtccgttct tcccgcggaa    960
tcaccgccgt cgctttctcc ctcggagccg gcagaggcgg cgtccatgtc gcaccctctg   1020
agtgctgcgg ttaccgccgc tacggctcct ccaggtgcta ccgtggcagg tgcgtcgccg   1080
gctgtgccgt ctctagcgtg gcctcacgac ggagtttatt acccaaggga cgcttttttc   1140
tcgttacttg gggccagtcg ctcggcagcg cccgtaatgt atcccggcgc cgtagcggcc   1200
cctccttctg cttcgccagc accgctgcct ttgccatctt atcccgcgtc ctacggcgcc   1260
cccgtcgtgg gttacgacca gttggcggta cgtcactttg cggattacgt ggatccccat   1320
tatcccgggt ggggtcggcg ttacgagccc cgccgtctt tgcatccgtc ttatcccgtg    1380
```

```
ccaccgccac catcaccggc ctattaccgt cggcgcgact ctccgggcgg tatggatgaa    1440
ccaccgtccg gatgggagcg ttacgacggt ggtcaccgtg gtcagtcgca gaagcagcac    1500
cgtcacgggg gcagcggtgg acacaacaaa cgccgtaagg aagccgcggc ggcgtcgtcg    1560
tcgtcgtcct cggacgaaga cttgagtttc cccggcgagg ccgagcacgg ccgggcgcga    1620
aagcgtctaa aaagtcacgt caatagcgac ggtggaagtg gcgggcacgc gggttccaat    1680
cagcagcagc aacaacgtta cgatgaactg cgggatgcca ttcacgagct gaaacgcgat    1740
ctgtttgccg cgcggcagag ttctacgtta cttcggcgg ctctccccgc tgcggcctct    1800
tcctccccga ctactactac cgtgtgtact cccaccggcg agctgacgag cggcggagga    1860
gaaacaccga cggcacttct atcaggaggt gccaaggtag ctgagcgcgc tcaggccggc    1920
gtggtgaacg ccagttgccg cctcgctacc gcgtcgggtt ctgaggcggc aacggcaggg    1980
ccttcgacgg cggggttcttc ttcctgtccg gctagtgtcg tgttagccgc cgctgctgcc    2040
caagccgccg cagcttccca gagcccgccc aaagacatgg tggatctgaa tcggcggatt    2100
tttgtggctg cgctcaataa gctcgaataa                                    2130

<210> SEQ ID NO 73
<211> LENGTH: 2127
<212> TYPE: DNA
<213> ORGANISM: Human cytomegalovirus

<400> SEQUENCE: 73
atgacgatgg acgagcagca gccgcaggct gtagcgccgg tctacgtggg cggctttctc      60
gcccgctatg accagtctcc ggacgaggcc gaattgctgt tgccgcggga cgtagtggag     120
cactggttgc acgcgcaggg ccagagacag ccttcgttgt cggtcgcgct cccgctcaac     180
atcaaccacg acgacacggc cgttgtagga cacgttgcgg cgatgcagag cgtccgcgac     240 ggtcttttt gcctgggctg cgtcacttcg cccaggtttc tggagattgt acgccgcgct     300
tcggaaaagt ccgagctggt ttcgcgcggg ccgtcagtc cgctgcagcc agacaaggtg     360
gtggagtttc tcagcggcag ctacgccggc ctctcgctct ccagccggcg ctgcgacgac     420
gtggaggccg cgacgtcgct ttcgggctcg gaaaccacgc cgttcaaaca cgtggctttg     480
tgcagcgtgg gtcggcgtcg cggtacgttg gccgtgtacg ggcgcgatcc cgagtgggtc     540
acgcagcggt ttccagacct cacggcgcc gaccgtgacg ggctacgtgc acagtggcag     600
cgctgcggca gcactgctgt cgacgcgtcg ggcgatccct ttcgctcaga cagctacggc     660 ctgtgggca acagcgtgga cgcgctctac atccgtgagc gactgcccaa gctgcgctac     720
gacaagcaac tagtcggcgt gacggagcgc gagtcgtacg tcaaggcgag cgtttcgcct     780
gaggcggcgt gcgatattaa agcggcgtcc gccgagcgtt cgggcgacag ccgcagtcag     840
gccgccacgc cggcggctgg ggcgcgggtt ccctcttcgt ccccgtcgcc tccagtcgaa     900
ccgccatctc ctgtccagcc gcctgcgctt ccagcgtcgc cgtccgttct tcccgcggaa     960
tcaccgccgt cgcttctctcc ctcggagccg gcagaggcgg cgtccatgtc gcaccctctg    1020
agtgctgcgg ttcccgccgc tacggctcct ccaggtgcta ccgtggcagg tgcgtcgccg    1080
gctgtgccgt ctctagcgtg gcctcacgac ggagtttatt tacccaaaga cgcttttttc    1140
tcgctacttg gggccagtcg ctcggcagcg cccgtcatgt atcccggtgc cgtagcggct    1200
cctccttctg cttcgccagc accgttgcct ttgccgtctt atcccgcgcc ctacggcgcc    1260
cccgtcgtgg gttacgacca gttggcggca cgtcactttg cggaatacgt ggatccccat    1320 tatccccgggt ggggtcggcg ttacgagccc gcgccgcctt tgcattcggc ttgtcccgtg    1380
```

```
ccgccgccac catcaccagc ctattaccgt cggcgcgatt ctccgggcgg tatggatgaa    1440
ccaccgtccg gatgggagcg ttacgacggt ggtcaccgtg gtcagtcgca gaagcagcac    1500
cgtcacgggg gcagcggtgg acacaacaaa cgccgtaagg aagctgcggc ggcgtcgtcg    1560
tcgtcctcgg acgaagactt gagtttcccc ggcgaggccg agcacggccg ggcgcgaaag    1620
cgtctaaaaa gtcacgtcaa tagcgacggt ggaagtggcg ggcacgcggg ttccaatcag    1680
cagcagcaac aacgttacga tgaactgcgg gatgccattc acgagctgaa acgcgatctg    1740
tttgccgcgc ggcagagttc tacgttactt tcggcggctc tccccgctgc ggcctcttcc    1800
tccccaacta ctactaccgt gtgtactccc accggcgagc tgacgagtgg cggaggagaa    1860
acacccacgg cacttctatc cggaggtgcc aaggtagctg agcgcgctca ggctggcgtg    1920
gtgaacgcca gttgccgcct cgctaccacg tcgggttctg agacggcaac ggccgggccc    1980
tcgacggaag gttcttcttc ctgcccggct agtgtcgtgt tagccgccgc tgctgcccaa    2040
gccgccgcag cttcccagag cccgcccaaa gacatggtag atctgaatcg gcggattttt    2100
gtggctgcgc tcaataagct cgagtaa                                        2127

<210> SEQ ID NO 74
<211> LENGTH: 2127
<212> TYPE: DNA
<213> ORGANISM: Human cytomegalovirus

<400> SEQUENCE: 74
atgacgatgg acgaacagca gccgcaggct gtagcgccgg tctacgtggg cggctttctc      60
gcccgttacg accagtctcc ggacgaggcc gaattgctgt tgccgcggga cgtagtggag     120
cactggttgc acgcgcaggg ccagggacag ccttcgttgt cggtcgcgct cccgctcaac     180
atcaatcacg acgacacggc cgttgtagga cacgttgcgg cgatgcagag cgttcgcgac     240 ggtcttttt gcctaggctg cgtcacttcg cccaggtttc tggagattgt gcgccgcgct     300
tcggaaaagt ccgagcttgt ttcgcgtggg cccgtcagtc cgctgcagcc ggacaaggtg     360
gtggagtttc tcagcggcag ctacgccggc ctctcgctct ccagccgcg ctgcgacgac     420 gtggaggccg cgacgtcgct ttcgggctcg gaaaccacgc cgttcaaaca cgtggctttg     480
tgcagcgtgg gtcggcgtcg cggtacgttg gccgtgtacg ggcgcgatcc cgagtgggtt     540
acccagcggt ttccagacct cacggcggcc gaccgcgacg ggctacgtgc acagtggcag     600
cgctgcggca gcactgctgt cgacgcgtcg ggcgatccct ttcgctcaga cagctacggc     660
ctgttgggca acagcgtgga cgcgctctac atccgtgagc gactgcccaa gctgcgctac     720
gacaagcaac tagtcggcgt gacggagcgc gagtcgtacg tcaaggcgag cgtttcgcct     780
gaggcggcgt gcgatattaa agcggcgtcc gccgagcgtt cgggcgacag ccgcagtcag     840
gccgccacgc cggcggctgg ggcgcgcgtt ccctcttcat ccccgtcgcc tccagtcgaa     900
ccgccatctc ctgtccagcc gcctgcgctt ccagcgtcgc cgtccgttct ccccacggaa     960
tcaccgccgt cgctttctcc tttggagccg gcagaggcgg cgtccatgtc gcaccctctg    1020
agtgctgcgg ttaccgccgc tacgctcct ccaggtgcta ccgtggcagg tgcgtcgccg    1080
gctgtgccgt cttttagcgtg gcctcacgac ggagtttatt tacccaaaga cgcttttttc    1140
tcgctacttg gggccagtcg ctcggcagcg cccgtcatgt atcccggcgc cgtagcggcc    1200
cctccttctg cttcgccagc accgctgcct ttgccgtctt atcccgcgtc ctacggcgcc    1260
cccgtcgtgg gttacgacca gttggcggca cgtcactttg cggactacgt ggatccccat    1320
```

| | | |
|---|---|---|
| tatcccgggt ggggtcggcg | ttacgagccc gcgccgcctt | tgcatccgtc ttatcccgtg | 1380 |
| ccgccgccac catcaccggc | ctattaccgt cggcgcgact | ctccgggcgg tatggatgaa | 1440 |
| ccaccgtccg gatgggagcg | ttacgacggt ggtcaccgtg | gtcagtcgca gaagcagcac | 1500 |
| cgtcacgggg gcagcggcgg | acacaacaaa cgccgtaagg | aagccgcggc ggcgtcgtcg | 1560 |
| tcgtcctcgg acgaagactt | gagtttcccc ggcgaggccg | agcacggccg ggcgcgaaag | 1620 |
| cgtctaaaaa gtcacgtcaa | cagcgacggt ggaagtggcg | ggcacgcggg ttccaatcag | 1680 |
| cagcagcaac aacgttacga | tgaactgcgg gatgccattc | acgagctgaa acgcgatctg | 1740 |
| tttgccgcgc ggcagagttc | tacgttactt tcggcggctc | tccctgctgc ggcctcttcc | 1800 |
| tccccgacta ctactaccgt | gtgtactccc accggcgagc | tgacgagcgg cggaggagaa | 1860 |
| acaccgacgg cacttctatc | aggaggtgcc aaggtagctg | agcgcgctca ggccggcgtg | 1920 |
| gtgaacgcca gttgccgcct | cgctaccgcg tcgggttctg | aggcggcaac ggcagggcct | 1980 |
| tcgacgcgg gttcttcttc | ctgcccggct agtgtcgtgt | tagccgccgc tgctgcccaa | 2040 |
| gccgccgcag cttcccagag | cccgcccaaa gacatggtgg | atctgaatcg gcggattttt | 2100 |
| gtggctgcgc tcaataagct cgagtaa | | 2127 |

<210> SEQ ID NO 75
<211> LENGTH: 2127
<212> TYPE: DNA
<213> ORGANISM: Human cytomegalovirus

<400> SEQUENCE: 75

| | | |
|---|---|---|
| atgacgatgg acgagcagca | gccgcaggct gtagcgccgg | tctacgtggg cggctttctc | 60 |
| gcccgctacg accagtctcc | ggacgaggcc gaattgctgt | tgccgcggga cgtagtggag | 120 |
| cactggttgc acgcgcaggg | ccagggacag ccttcgttgt | cggtcgcgct cccgctcaac | 180 |
| atcaaccacg acgacacggc | cgttgtagga cacgttgcgg | cgatgcagag cgtccgcgac | 240 |
| ggtcttttttt gcctgggctg | cgtcacttcg cccaggtttc | tggagattgt acgccgcgct | 300 |
| tcggaaaagt ccgagctggt | ttcgcgcggg cccgtcagtc | cgctgcagcc agacaaggtg | 360 |
| gtggagtttc tcagcggcag | ctacgccggc ctctcgctct | ccagccggcg ctgcgacgac | 420 |
| gtggaggccg cgacgtcgct | ttcgggctcg gaaaccacgc | cgttcaaaca cgtggctttg | 480 |
| tgcagcgtgg gtcggcgtcg | cggtacgttg ccgtgtacg | ggcgcgatcc cgagtgggtc | 540 |
| acacaacggt ttccagacct | cacggcggcc gaccgtgacg | ggctacgtgc acagtggcag | 600 |
| cgctgcggca gcactgctgt | cgacgcgtcg ggcgatccct | ttcgctcaga cagctacggc | 660 |
| ctgttgggca acagcgtgga | cgcgctctac atccgtgagc | gactgcccaa gctgcgctac | 720 |
| gacaagcaac tagtcggcgt | gacggagcgc gagtcgtacg | tcaaggcgag cgtttcgcct | 780 |
| gaggcggcgt gcgatattaa | agcggcgtcc gccgagcgtt | cgggcgacag ccgcagtcag | 840 |
| gccgccacgc cggcggctgg | ggcgcgcgtt ccctcttcgt | ccccgtcgcc tccagtcgaa | 900 |
| ccgccatctc ctgtccagcc | gcctgcgctt ccagcgtcgc | cgtccgttct tcccgcggaa | 960 |
| tcaccgccgt cgctttctcc | ctcggagccg gcagaggcgg | cgtccatgtc gcaccctctg | 1020 |
| agtgctgcgg ttcccgccgc | tacgctcct ccaggtgcta | ccgtggcagg tgcgtcgccg | 1080 |
| gctgtgccgt ctctagcgtg | gcctcacgac ggagtttatt | acccaaaga cgcttttttc | 1140 |
| tcgctacttg gggccagtcg | ctcggcagcg cccgtcatgt | atcccggtgc cgtagcggct | 1200 |
| cctcttctg cttcgccagc | accgttgcct ttgccgtctt | atcccgcgcc ctacggcgcc | 1260 |
| cccgtcgtgg gttacgacca | gttggcgaca cgtcactttg | cggaatacgt ggatccccat | 1320 |

-continued

```
tatcccgggt ggggtcggcg ttacgagccc gcgccgcctt tgcattcggc ttgtcccgtg    1380
ccgccgccac catcaccagc ctattaccgt cggcgcgatt ctccgggcgg tatggatgaa    1440
ccaccgtccg gatgggagcg ttacgacggt ggtcaccgtg gtcagtcgca gaagcagcac    1500
cgtcacgggg gcagcggtgg acacaacaaa cgccgtaagg aagctgcggc ggcgtcgtcg    1560
tcgtcctcgg acgaagactt gagtttcccc ggcgaggccg agcacggccg ggcgcgaaag    1620
cgtctaaaaa gtcacgtcaa tagcgacggt ggaagtggcg ggcacgcggg ttccaatcag    1680
cagcagcaac aacgttacga tgaactgcgg gatgccattc acgagctgaa acgcgatctg    1740
tttgccgcgc ggcagagttc tacgttactt cggcggctc tccccgctgc ggcctcttcc     1800
tccccaacta ctactaccgt gtgtactccc accggcgagc tgacgagtgg cggaggagaa    1860
acacccacgg cacttctatc cggaggtgcc aaggtagctg agcgcgctca ggccggcgtg    1920
gtgaacgcca gttgccgcct cgctaccgcg tcgggttctg aggcggcaac ggccgggccc    1980
tcgacggcag gttcttcttc ctgcccggct agtgtcgtgt tagccgccgc tgctgcccaa    2040
gccgccgcag cttcccagag cccgcccaaa gacatggtag atctgaatcg gcggattttt    2100
gtggctgcgc tcaataagct cgagtaa                                        2127
```

<210> SEQ ID NO 76
<211> LENGTH: 2127
<212> TYPE: DNA
<213> ORGANISM: Human cytomegalovirus

<400> SEQUENCE: 76

```
atgacgatgg acgagcagca gtcgcaggct gtggcgccgg tctacgtggg cggctttctc      60
gcccgctacg accagtctcc ggacgaggcc gaattgctgt tgccgcggga cgtagtggag     120
cactggttgc acgcgcaggg ccagggacag ccttcgttgt cggtcgcgct cccgctcaat     180
atcaaccacg acgacacggc cgttgtagga cacgttgcgg cgatgcagag cgtccgcgac     240 ggtcttttttt gcctgggctg cgtcacttcg cccaggtttc tggagattgt acgccgcgct    300
tcggaaaagt ccgagctggt ttcgcgcggg ccgtcagtc cgctgcagcc ggacaaggtg      360
gtggagtttc tcagcggcag ttacgccggc ctctcgctct ccagccggcg ctgcgacgac     420
gtggaggccg cgacgtcgct ttcgggctcg gaaaccacgc cgttcaaaca cgtggctttg     480
tgcagcgtgg gtcggcgtcg cggtacgttg gccgtgtacg ggcgcgatcc cgagtgggtc     540
actcagcggt ttccagacct cacggcggcc gaccgcgacg ggctacgtgc acagtggcag     600
cgctgcggca gcactgctgt cgacgcgtcg ggcgatccct ttcgctcaga cagctacggc     660
ctgttgggca acagcgtgga cgcgctctac atccgtgagc gactgcccaa gctgcgctac     720
gacaagcaac tagtcggcgt gacggagcgc gagtcgtacg tcaaggcgag cgtttcgcct     780
gaggcggcgt gcgatattaa agcggcgccc gccgagcgtt cggcgacag ccgcagtcgg      840 gccgccacgc cggcggctgg ggcgcgcgtt ccctcttcat ccccgtcacc tccagtcgaa     900
ccgccatctc ctgttcagtc gcctgcgctt ccagtgtcgc cgtccgttct ccccgcggaa     960
tcaccgccgt cgctttctcc ctcggagtcg gcagaggcgg cgtccatgtc gcaccctctg    1020
agtgctgcgg ttaccgccgc tacggctcct ccaggtgcta ccgtggcagg tgcgtcgccg    1080
gctgtgccgt ctctagcgtg gcctcacgac ggagtttatt tacccaaaga cgcttttttc    1140
tcgctacttg gggccagtcg ctcggcagcg ccgtcatgt atcccggcgc cgtagcggcc     1200
cctccttctg cttcgccagc accgctgcct ttgccgtctt atcccgcgtc ctacggcgcc    1260
```

```
cccgtcgtgg gttacgacca gttggcggca cgtcactttg cggactacgt ggatccccat    1320
tatcccgggt ggggtcggcg ttacgagccc acgccgcctt tgcattcgtc ttatcccgtg    1380
ccgccgccac catcaccggc ctattaccgt cggcgcgact ctccgggcgg tatggatgaa    1440
ccaccgtccg gatgggagcg ttacgacggt ggtcaccgtg gtcagtcgca gaagcagcac    1500
cgtcacgggg gcagcggcgg acacaacaaa cgccgtaagg aagccgcggc ggcgtcgtcg    1560
tcgtcctcgg acgaagactt gagtttcccc ggcgaggccg agcacggccg ggcgcgaaag    1620
cgtctaaaaa gtcacgtcaa tagcgacggt ggaagtggcg ggcacgcggg ttccaatcag    1680
cagcagcaac aacgttacga tgaactgcgg gatgccattc acgagctgaa acgcgatctg    1740
tttgccgcgc ggcagagttc tacgttactt tcggcggctc tccccgctgc ggcctcttcc    1800
tccccaacta ctactaccgt gtgtactccc accggcgagc tgacgagcgg cggaggagaa    1860
acaccgacgg cacttctatc cggaggtgcc aaggtagctg agcgcgctca ggccggcgtg    1920
gtgaacgcca gttgccgcct cgctaccgcg tcgggttctg aggcggcaac ggccgggccc    1980
tcgatggcag gttcttcttc ctgcccggct agtgtcgtgt tagccgccgc tgctgctcaa    2040
gccgccgcag cttcccagag cccgcccaaa gacatggtag atctgaatcg gcggattttt    2100
gtggctgcgc tcaataagct cgagtaa                                        2127
```